US011168129B2

(12) United States Patent
Kobie et al.

(10) Patent No.: US 11,168,129 B2
(45) Date of Patent: Nov. 9, 2021

(54) BROADLY NEUTRALIZING ANTI-INFLUENZA HUMAN MONOCLONAL ANTIBODY AND USES THEREOF

(71) Applicant: University of Rochester, Rochester, NY (US)

(72) Inventors: James J. Kobie, Rochester, NY (US); Michael Piepenbrink, Rochester, NY (US); Michael Keefer, Rochester, NY (US); Luis Martinez-Sobrido, Rochester, NY (US); Aitor Nogales, Rochester, NY (US)

(73) Assignee: University of Rochester, Rochester, NY (US)

( * ) Notice: Subject to any disclaimer, the term of this patent is extended or adjusted under 35 U.S.C. 154(b) by 32 days.

(21) Appl. No.: 16/611,399

(22) PCT Filed: May 10, 2018

(86) PCT No.: PCT/US2018/032063
§ 371 (c)(1),
(2) Date: Nov. 6, 2019

(87) PCT Pub. No.: WO2018/213097
PCT Pub. Date: Nov. 22, 2018

(65) Prior Publication Data
US 2020/0140526 A1    May 7, 2020

Related U.S. Application Data

(60) Provisional application No. 62/506,256, filed on May 15, 2017.

(51) Int. Cl.
A61K 39/42        (2006.01)
C07K 16/10        (2006.01)
A61P 31/16        (2006.01)
A61K 39/00        (2006.01)

(52) U.S. Cl.
CPC .......... *C07K 16/1018* (2013.01); *A61P 31/16* (2018.01); *A61K 2039/505* (2013.01); *A61K 2039/545* (2013.01); *C07K 2317/33* (2013.01); *C07K 2317/76* (2013.01); *C07K 2317/92* (2013.01)

(58) Field of Classification Search
None
See application file for complete search history.

(56) References Cited

FOREIGN PATENT DOCUMENTS

| WO | 2015020913 A2 | 2/2015 |
| WO | 2015028478 A1 | 3/2015 |
| WO | 2016205347 A1 | 12/2016 |

OTHER PUBLICATIONS

Rudikoff et al., "Single amino acid substitution altering antigen-binding specificity," Proc Natl Acad Sci USA 79:1979-1983 (Year: 1982).*
Goel et al., "Plasticity within the Antigen-Combining Site May Manifest as Molecular Mimicry in the Humoral Immune Response," J. Immunol. 173: 7358-7367 (Year: 2004).*

(Continued)

*Primary Examiner* — M Franco G Salvoza
(74) *Attorney, Agent, or Firm* — Fox Rothschild LLP

(57) ABSTRACT

The present invention relates to broadly neutralizing anti-influenza monoclonal antibodies or antigen-binding fragments thereof. The present invention further relates to therapeutic uses of the isolated antibody or the antigen-binding fragment thereof.

8 Claims, 13 Drawing Sheets
Specification includes a Sequence Listing.

(56) References Cited

OTHER PUBLICATIONS

Lloyd et al., "Modelling the human immune response: performance of a 1011 human antibody repertoire against a broad panel of therapeutically relevant antigens," Protein Engineering, Design & Selection, vol. 22, No. 3: 159-168 (Year: 2009).*

Edwards et al., "The Remarkable Flexibility of The Human Antibody Repertoire; Isolation of Over One Thousand Different Antibodies to a Single Protein, BLys," J. Mol. Biol. 334: 103-118 (Year: 2003).*

Sparrow et al., Passive immunization for influenza through antibody therapies, a review of the pipeline, challenges and potential applications, Elsevier, Vaccine (2016); 34(45):5442-5448.

Whittle et al., "Broadly neutralizing human antibody that recognizes the receptor-binding pocket of influenza virus hemagglutinin," PNAS (2011); 108(34):14216-14221.

Krause et al., "A Broadly Neutralizing Human Monoclonal Antibody That Recognizes a Conserved, Novel Epitope on the Globular Head of the Influenza H1N1 Virus Hemagglutinin," Journal of Virology (2011); 85(20):10905-10908.

Wang et al., "Generation and characterization of new monoclonal antibodies against swine origin 2009 influenza A (H1N1) virus and evaluation of efficacy in a mouse model," Elseveir, Developmental and Comparative Immunology (2017); 67(27):8-17.

Lee et al., "Structural Characterization of Viral Epitopes Recognized by Braodly Cross-Reactive Antibodies," Current Topics in Microbiology and Immunology (2015); 386:323-341.

Marjuki et al., "Human Monoclonal Antiboy 81.39a Effectively Neutralizes Emerging INfluenza A Viruses of Group 1 and 2 Hemagglutinins," Journal of Virology (2016); 90(23):abstract only.

Nogales et al., "A Highly Potent and Broadly Neutralizing H1 Influenza-Specific Human Monoclonal Antibody," Scientific Reports (2018); 8(1):4374.

* cited by examiner

```
B-cell_derived_constant_region    GCTGGCTGCTCGGTGCTGGTGTACAGGTCCCCGGAGGCATCCTGGCTGGGTGGGAAGTTCTGG
IgA1_constant_region              GCTGGCTGCTCGTGGTGCTGGTGTACAGGTCCCCGGAGGCATCCTGGCTGGGTGGGAAGTTTCTGG
                                  ****************************************************************

B-cell_derived_constant_region    CGGTCACGCCCCTGTCCCGCTTTCGCTCCAGGTCACACTGAGTGGCTCCTGGGGGAAGAAGC
KPF1_heavy_native_constant_region CGGTCACGCCCCTGTCCCGCTTTCGCTCCAGGTCACACTGAGTGGCTCCTGGGGGAAGAAGC
IgA1_constant_region              CGGTCACGCCCCTGTCCCGCTTTCGCTCCAGGTCACACTGAGTGGCTCCTGGGGGAAGAAGC
                                  ****************************************************************

KPF1_heavy_native_constant_region CCTGGACCAGGCAGGCGATGACCACCACGTTCCCATCTGCTGGCTGCTGCTGCAGAGGCTCAGCG
IgA1_constant_region              CCTGGACCAGGCAGGCGATGACCACCACGTTCCCATCTGGCTGCTGGCTGCTGCAGAGGCTCAGCG
B-cell_derived_constant_region    ****************************************************************

KPF1_heavy_native_constant_region GGAAGACCTTGGGGCTGGTCGGGGATG
IgA1_constant_region              GGAAGACCTTGGGGCTGGTCGGGGATG
                                  ***************************
```

FIG. 1C

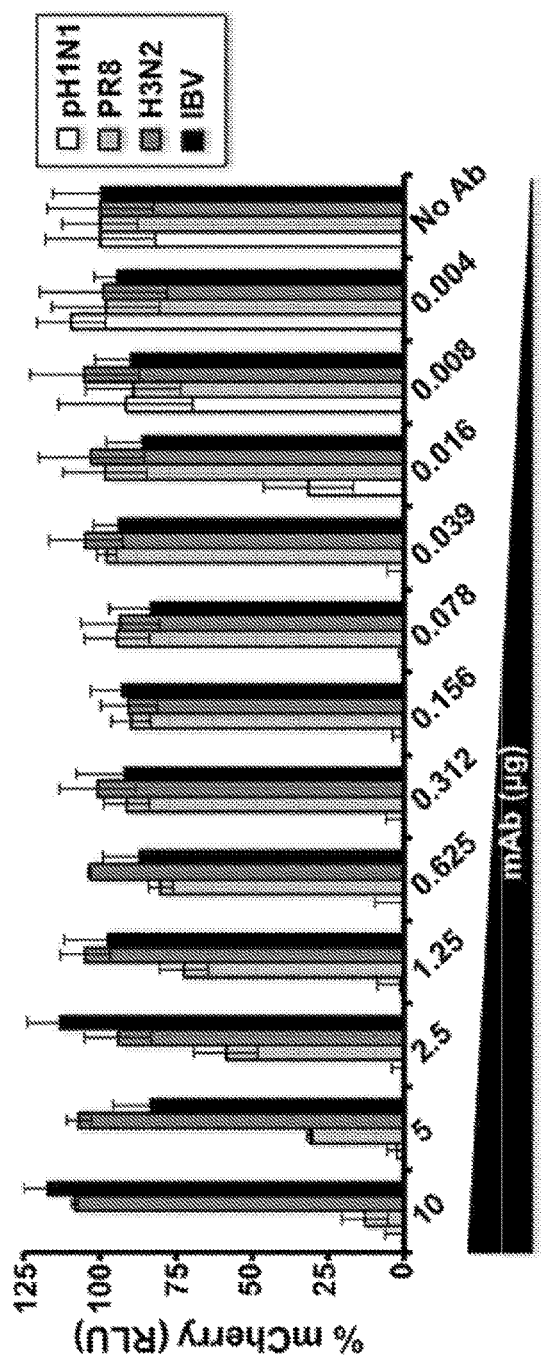
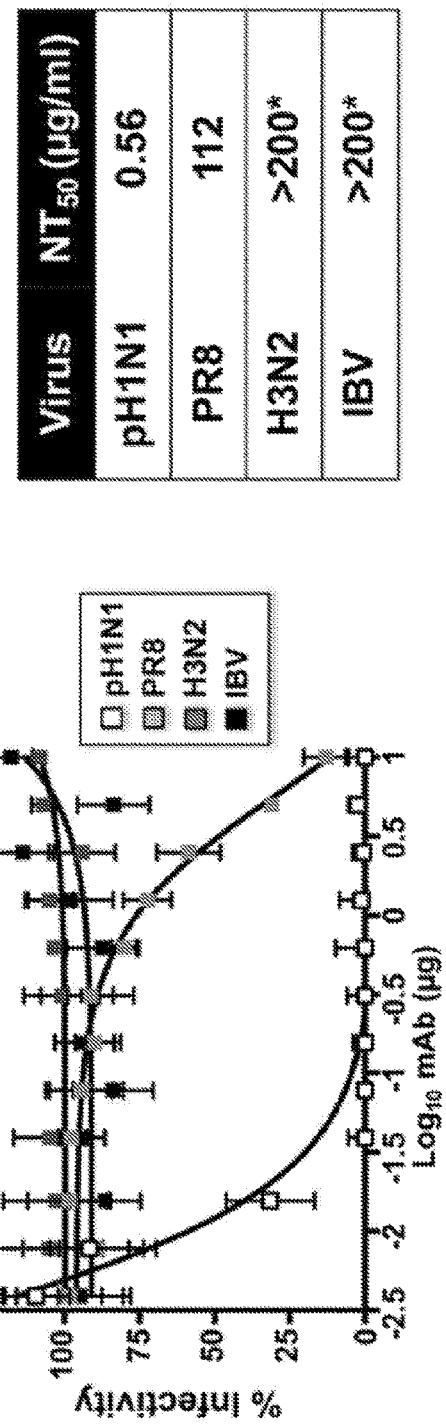
FIG. 4A
FIG. 4B
FIG. 4C

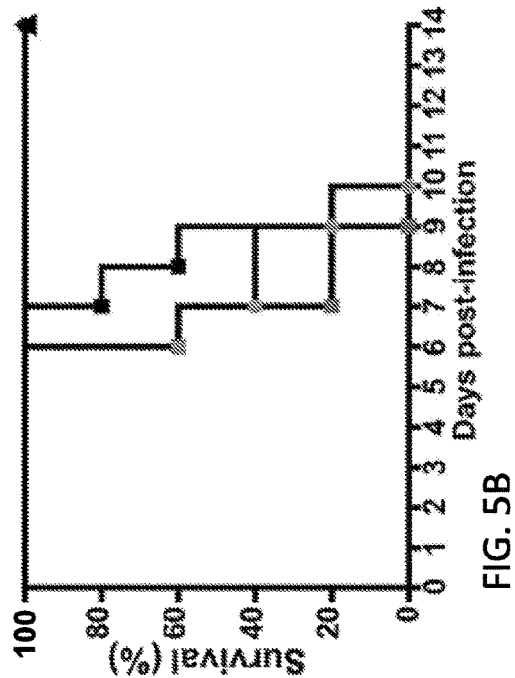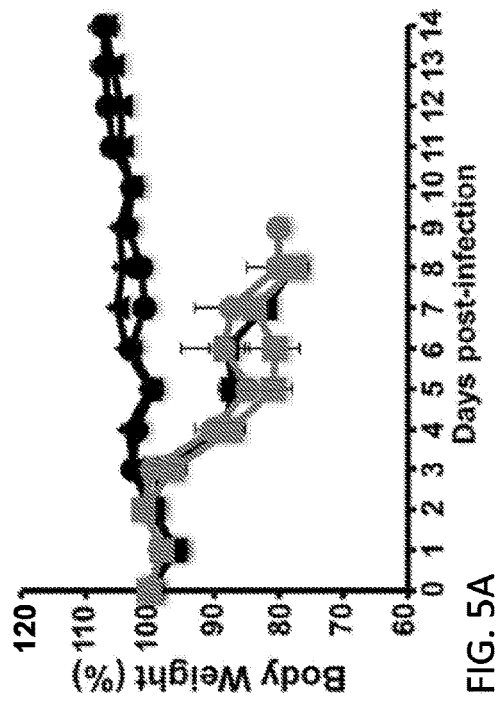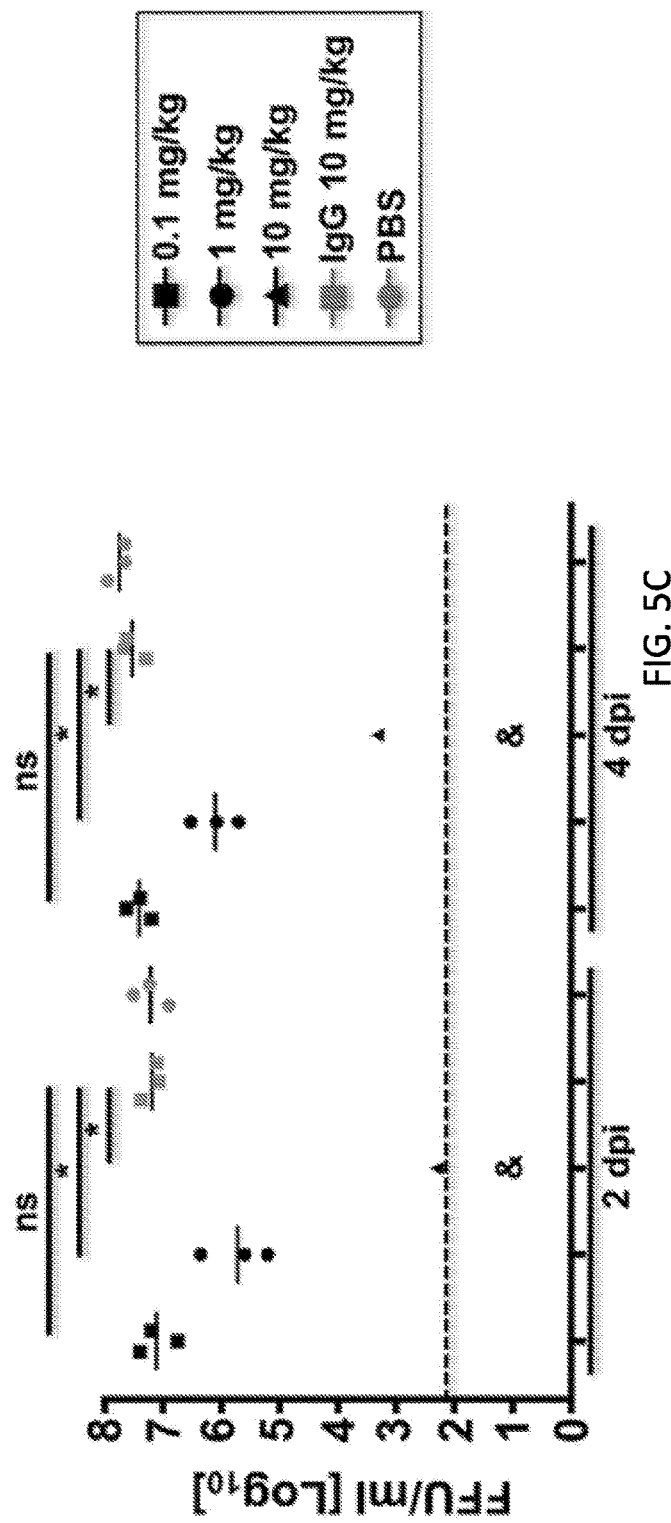
FIG. 5A
FIG. 5B
FIG. 5C

| Virus | HA | NA | NT (μg/ml) | HAI (μg/ml) |
|---|---|---|---|---|
| MARM 1 | E129K | - | >200 | >200 |
| MARM 2 | E129K | - | >200 | >200 |
| MARM 3 | E129K K180N | - | >200 | >200 |
| WT | - | - | 0.39 | 0.39 |

| Virus | HA | NA | HAI (µg/ml) |
|---|---|---|---|
| MARM 1 | E129K | - | > 200 |
| MARM 2 | E129K | - | > 200 |
| MARM 3 | E129K | - | > 200 |
| WT | - | - | 0.78 |

FIG. 7E

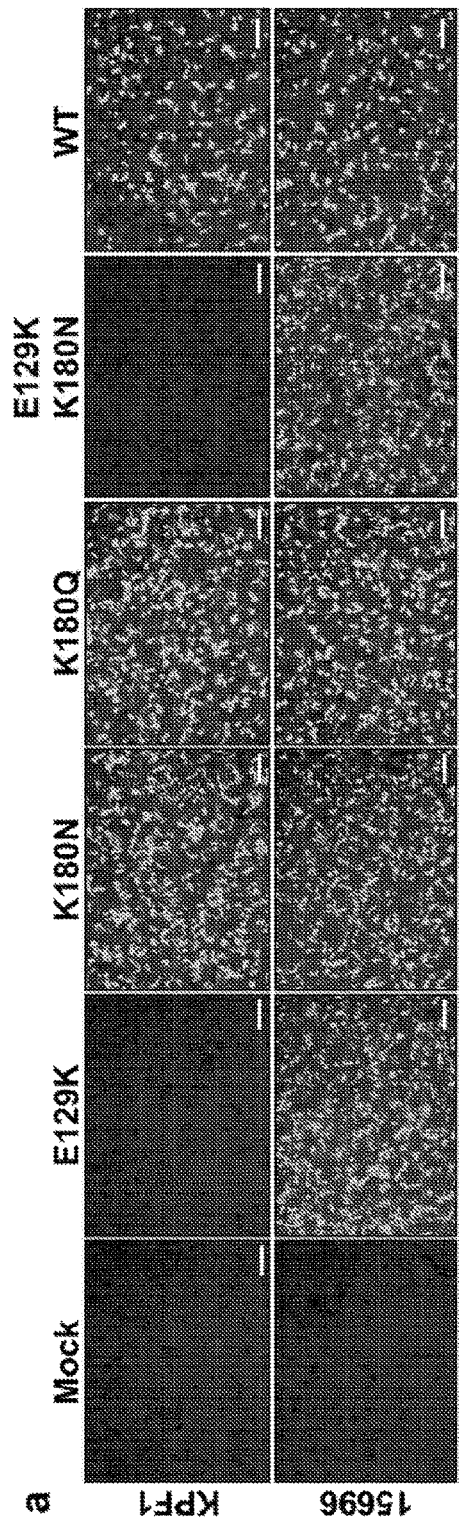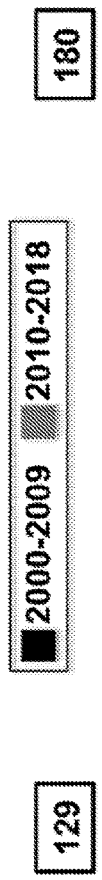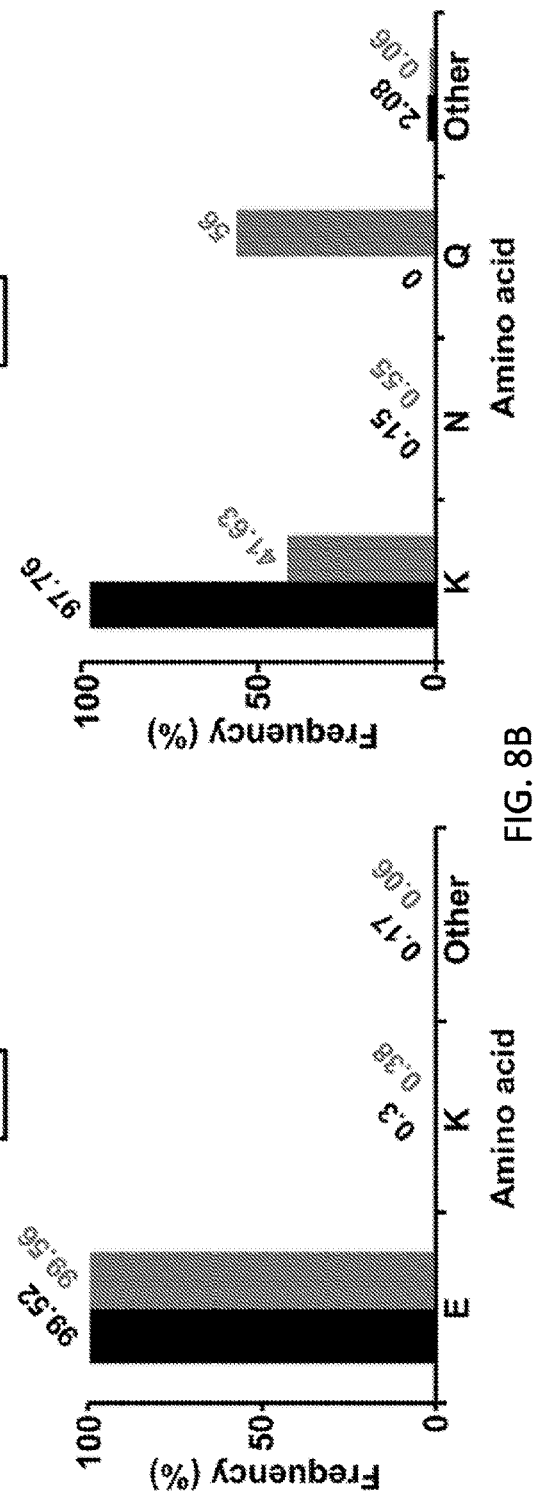
FIG. 8A
FIG. 8B

BROADLY NEUTRALIZING ANTI-INFLUENZA HUMAN MONOCLONAL ANTIBODY AND USES THEREOF

CROSS REFERENCE TO RELATED APPLICATIONS

This application is the U.S. National Phase of International Patent Application No. PCT/US2018/032063, filed May 10, 2018, claims priority to U.S. Provisional Application No. 62/506,256 filed May 15, 2017, the disclosures of which are incorporated herein by reference.

GOVERNMENT INTERESTS

This invention was made with Government Support under AI116285 awarded by the National Institutes of Health. The Government has certain rights in the invention.

FIELD OF THE INVENTION

This invention relates to broadly neutralizing anti-influenza monoclonal antibodies (mAbs) or antigen-binding fragments thereof. The present invention further relates to the therapeutic uses of the antibody or the antigen-binding fragment.

BACKGROUND OF THE INVENTION

Influenza, commonly known as "the flu", is an infectious disease caused by influenza virus. There are four types of influenza viruses: A, B, C and D. Human influenza A and B viruses cause seasonal epidemics of the disease. The first and most important step in preventing flu is to get an annual flu vaccination. Although a licensed influenza vaccine has been available for over seventy years, influenza infections still remain a major public health concern. Annually, in the United States influenza leads to 15,000 deaths and 300,000 hospitalizations, with ~3 to 5 million severe cases and 200,000 to 500,000 deaths per year globally (Girard M P, et al. 2005. Vaccine 23:5708-5724; Nogales A, et al. 2016. Int J Mol Sci 18; Dushoff J, et al. 2006. Am J Epidemiol 163:181-187; Doshi P. 2008. Am J Public Health 98:939-945; and Thompson W W, et al. 2009. Am J Public Health 99 Suppl 2:S225-230). In addition, the financial burden in the US averages more than 80 billion dollars annually, because hospital costs or missed school or work days (Molinari N A, et al. 2007. Vaccine 25:5086-5096; Gasparini R, et al. 2012. Hum Vaccin Immunother 8:21-28; and Keech M, et al. 2008. Pharmacoeconomics 26:911-924). A key vulnerability is the need for annual selection of seasonal influenza vaccine composition to adequately match strains expected to be most prominent during the upcoming season. If the seasonal vaccine does not match the circulating strain the vaccine may be ineffective. Due to the propensity of influenza for antigenic drift and shift, and its tendency to elicit predominantly strain specific antibodies, humanity remains susceptible to waves of new strains with pandemic potential for which limited or no immunity may exist, as was the case in 1918 when the "Spanish Flu" killed ~30-50 million people (Taubenberger J K, et al. 2006. Emerg Infect Dis 12:15-22).

Influenza A virus (IAV) has 18 HA subtypes, which are further classified in two phylogenetic groups: group 1 (H1, H2, H5, H6, H8, H9, H11, H12, H13, H16, H17 and H18 subtypes) and group 2 (H3, H4, H7, H10, H14 and H15 subtypes). Seasonal vaccinations include influenza type A H1, H3, and type B viruses. Recent pandemics, including the latest 2009 novel H1N1 pandemic (Smith G J, et al. 2009. Nature 459:1122-1125 and Kilbourne ED. 2006. Emerg Infect Dis 12:9-14), which in less than 1 year infected more than 600,000 individuals worldwide causing nearly 16,000 deaths in over 200 countries (Centers for Disease C, Prevention. 2009. Update: infections with a swine-origin influenza A (H1N1) virus—United States and other countries, Apr. 28, 2009. MMWR Morb Mortal Wkly Rep 58:431-433). There is a need for new vaccine strategies and therapeutics that confer broad protection against diverse influenza strains.

SUMMARY OF INVENTION

This invention addresses the need by providing broadly neutralizing anti-influenza monoclonal antibodies or antigen-binding fragments thereof.

In one aspect, the invention provides an isolated antibody or antigen-binding fragment thereof that specifically binds to a hemagglutinin (HA) of influenza A virus (IAV) H1 subtype, comprising: (i) a heavy chain variable region that comprises HCDR1, HCDR2, and HCDR3 comprising the amino acid sequences of SEQ ID NOs: 3-5, respectively, and (ii) a light chain variable region that comprises LCDR1, LCDR2 and LCDR3 comprising the amino acid sequences of SEQ ID NOs: 6-8, respectively. In the isolated antibody or the antigen-binding fragment described above, the heavy chain variable region can include the amino acid sequence of SEQ ID NO: 1. The light chain variable region can include the amino acid sequence of SEQ ID NO: 2.

The invention also provides an isolated antibody or antigen-binding fragment thereof that specifically binds to an HA of IAV H1 subtype. When bound to the HA, the antibody binds to a conformational epitope dependent on (or containing) the E and K amino acid residues corresponding to E129 and K180 of the HA of pH1N1 (SEQ ID NO: 13). Further provided is an isolated antibody or the antigen-binding fragment thereof that competes for binding to an HA of IAV H1 subtype in a cross-blocking assay with the antibody or the antigen-binding fragment described above.

The above-described antibody or antigen-binding fragment can include a variant Fc constant region. The isolated antibody or the antigen-binding fragment can be a chimeric antibody, a humanized antibody, or a human antibody. The antibody or fragment can be conjugated to a therapeutic agent, a polymer, a detectable label, or an enzyme. Examples of the polymer include polyethylene glycol (PEG). Examples of the therapeutic agent include a cytotoxic agent.

In a second aspect, the invention provides an isolated nucleic acid encoding one or more of the CDRs, the heavy or light chain variable region, or antigen binding portion, of any one of above-described antibodies or antigen-binding fragments. The nucleic acid can be used to express a polypeptide having one or both sets of the HCDRs or LCDRS, a chain of the antibody or antigen-binding fragment, or the antibody or fragment described above. For this purpose, one can operatively link the nucleic acid to suitable regulatory sequences to generate an expression vector. Accordingly, within the scope of this invention are a cultured host cell comprising the vector and a method for producing a polypeptide, an antibody, or antigen binding portion thereof. The method includes: obtaining a cultured host cell comprising a vector comprising a nucleic acid sequence encoding one or more of the above mentioned CDRs, polypeptide, a heavy chain variable region or a light chain variable region of the antibody or antigen binding portion thereof as described above; culturing the cell in a medium under conditions permitting expression of a polypeptide encoded by the vector and assembling of an antibody or fragment thereof, and purifying the antibody or fragment from the cultured cell or the medium of the cell.

The antibody or fragment described above can be used in a method of neutralizing IAV or a method of treating, preventing or controlling an IAV infection. The method includes administering to a subject in need thereof a therapeutically effective amount of the antibody or fragment. Accordingly, the invention also provides a pharmaceutical composition comprising (i) the antibody or an antigen-binding fragment thereof, and (ii) a pharmaceutically acceptable carrier.

The details of one or more embodiments of the invention are set forth in the description below. Other features, objectives, and advantages of the invention will be apparent from the description and from the claims.

BRIEF DESCRIPTION OF THE DRAWINGS

FIGS. 1A, 1B, and 1C are a set of diagrams showing isolation and molecular characterization of KPF1 human monoclonal antibody (hmAb). (FIG. 1A) Gating strategy to isolate peripheral blood plasmablasts (CD19+IgD-CD38+CD27++) 7 days after immunization. (FIG. 1B) Alignment of KPF1 VH and Vk (SEQ ID NOs: 1 and 9) with presumed germline amino acid sequences (SEQ ID NOs: 10 and 11). (FIG. 1C) Alignment of nucleic acids encoding a constant region of an antibody from an expanded B cell lineage (SEQ ID NO: 22) used to make KPF1 and an IgA1 constant region (SEQ ID NO: 23).

(FIG. 2C) Purified KPF1 was captured on a Protein G chip with the pH1N1 HA at decreasing concentrations passed over each channel. The data points are shown in black and the fit to a 1:1 binding model are shown in red. The results of one representative experiments of two are presented.

FIGS. 4A, 4B, and 4C are diagrams and a table showing potent in vitro neutralizing activity of KPF1 hmAb. Virus neutralization was measured using a fluorescent-based microneutralization assay (Nogales A, et al. 2016. Virus Res 213:69-81; and Nogales A, et al. 2015. Virology 476:206-216). MDCK cells were infected with mCherry-expressing A/California/04/2009 (pH1N1) and A/Puerto Rico/08/1934 (PR8) H1N1, A/Wyoming/3/2003 (H3N2), or B/Brisbane/60/2008 (IBV) viruses, which were pre-incubated with two-fold serial dilutions of KPF1 hmAb. At 24 h p.i., virus neutralization was evaluated and quantified using a fluorescence microplate reader (FIG. 4A), and the percentage of infectivity calculated using sigmoidal dose response curves (FIG. 4B). Mock-infected cells and viruses in the absence of Ab (No Ab) were used as internal controls. Percent of neutralization was normalized to infection in the absence of Ab. Data show means±SD of the results determined for triplicates. (FIG. 4C) $NT_{50}$ of KPF1 hmAb by fluorescent-based assay. *, Highest amount of mAb without detectable neutralizing effect.

FIGS. 5A, 5B, 5C and 5D are diagrams showing that KPF1 hmAb restricts pH1N1 replication in vivo. Female C57BL/6 mice (N=11) were treated i.p. with 0.1, 1 or 10 mg/kg of KPF1 hmAb, or with 10 mg/kg of an isotype control (IgG), or PBS 24 h before infection. Mice were then challenged with $10 \times MLD_{50}$ of pH1N1 and monitored daily for 2 weeks for body weight loss (FIG. 5A) and survival (FIG. 5B). Mice that lost 25% of their body weight were sacrificed. Data represent the means±SD (N=5). To evaluate viral replication in the lungs (FIG. 5C), mice were sacrificed at 2 (N=3) and 4 (N=3) days p.i. and whole lungs were used to quantify viral titers by immunofocus assay (FFU/ml). *Indicates $p<0.05$ using one-way ANOVA and Dunnett's test for multiple comparison correction. Ns, no statistically significant differences. (d) Evaluation of KPF1 for its prophylactic activity against multiple H1 influenza strains. Female C57BL/6 mice (N=6) received 10 mg/kg of KPF1 or IgG isotype control (IC) 24 h before viral infection. Mice were then challenged with 10×MLD50 of PR8 H1N1 (circles), TX H1N1 (squares), or NC H1N1 (triangles) and viral replication in lungs at 2 (N=3) and 4 (N=3) days p.i. (black and grey symbols, respectively) was evaluated as indicated above. For (C) and (D), symbols represent data from individual mice. Bars, geometric mean lung virus titers; dotted line, limit of detection (200 FFU/ml). & indicates virus was not detected or was detected only in 1 of 3 mice.

FIGS. 7A, 7B, 7C, 7D and 7E are tables, a set of photographs, and diagrams showing generation and characterization of MARMs. (FIG. 7A) Amino acid mutations in the HAs and NAs of WT or mAb-resistant mutants (MARMs 1, 2 and 3) after 5 rounds of selection in the presence (MARMs) or absence (WT) of hmAb KPF1. The mutations effects on reactivity with the hmAb KPF1 were also evaluated in a microneutralization assay ($NT_{50}$) and HAI. (FIG. 7B) Characterization of MARMs by immunofluorescence. MDCK cells were mock infected (Mock) or infected (MOI 0.01) with pH1N1 WT or the MARMs (1, 2 and 3). At 36 h p.i., cells were fixed and protein expression was evaluated by IFA using the hmAb KPF1, or the mouse mAbs 29E3 (anti-HA) and HB-65 (anti-NP). DAPI was used for nuclear staining. Merge from representative images (10× magnification) are included. Scale bar, 50 nm. (FIG. 7C) Multicycle growth kinetics of pH1N1 WT and MARMs in MDCK cells. Virus titers in tissue culture supernatants of MDCK cells infected (MOI, 0.001) with pH1N1 WT or MARMs viruses were analyzed at the indicated h p.i by immunofocus assay (FFU/ml) using the anti-NP mouse mAb HB-65. Data represent the means±SDs of the results determined for triplicate wells. * indicates $p<0.05$ (WT versus MARM 3) using a Student's t test. (FIG. 7D) Tridimensional protein structure for the globular head of HA of pH1N1. The image was created using the software program PyMol and the published structure for the HA of pH1N1 (3LZG, Xu R, et al. 2010. Science 328:357-360). Positions of amino acid substitutions in the MARMs (E129 and K180) are colored in yellow. The residues at each antigenic site are colored as red for the Sa site, orange for the Sb site, green for the Ca site, and magenta for the Cb site. The receptor binding site (RBS) location in the structure is indicated. (FIG. 7E) Generation of MARMs for TX H1N1. Amino acid changes in the HA and NA of TX H1N1 WT or MARMs (1, 2 and 3) after 5 rounds of selection in the presence (MARMs) or absence (WT) of hmAb KPF1. The effect of E129K mutation on reactivity with KPF1 was also evaluated in a HAI assay, using WT TX H1N1 as an internal control.

FIGS. 8A and 8B are a set of photographs and diagrams showing relevance of amino acids 129 and 180 for the binding of KPF1 hmAb. (8A) Binding of KPF1 hmAb to WT and mutant HA proteins. HEK293T cells were transiently transfected with the pCAGGS plasmids expressing WT or amino acid substitutions E129K, K180N, K180Q or E129K/K180N mutant HAs. Mock transfected cells were used as internal control. At 24 h post-transfection, cells were fixed and protein expression was evaluated by IFA using the hmAb KPF1, or a goat pH1N1 anti-HA polyclonal antibody as a control. DAPI was used for nuclear staining. Merge from representative images (10× magnification) are included. Scale bar, 50 nm. (8B) Frequency of amino acid changes found in IAV H1N1 HA over time. Publicly available sequences of IAV H1N1 HA protein (Influenza Research Database) isolated between 2000-2009 (n=8,586; black) or 2010-2018 (n=8,417; grey) were analyzed and plotted according to the percentage of sequences containing the indicated amino acids at positions 129 (right) or 180 (left).

DETAILED DESCRIPTION OF THE INVENTION

Figure 1A:
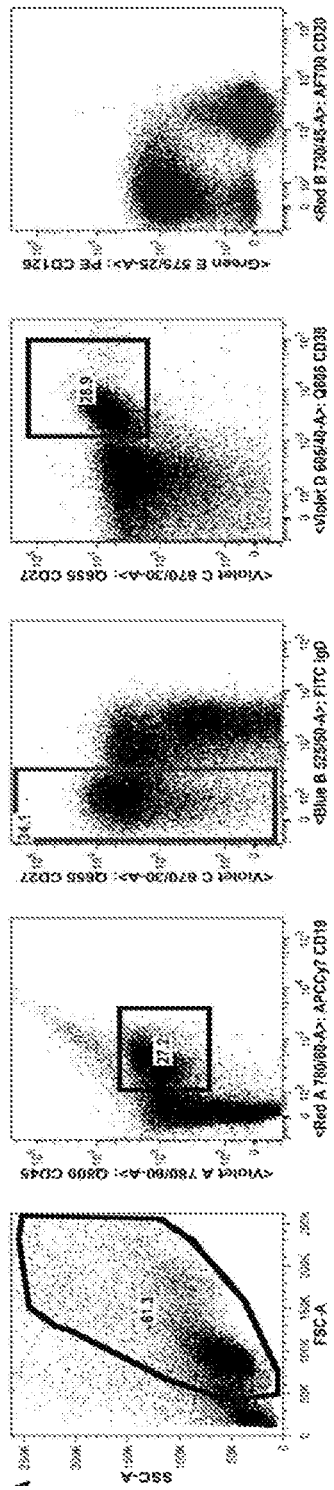

This invention is based, at least in part, on unexpected broadly neutralizing anti-influenza activities of certain monoclonal antibodies or antigen-binding fragments thereof. These antibodies and antigen-binding fragments constitute a novel therapeutic strategy in protection from influenza infections.

Antibodies

The invention disclosed herein involves broadly neutralizing anti-influenza monoclonal antibodies or antigen-binding fragments thereof. These antibodies refer to a class of neutralizing antibodies that neutralize multiple influenza virus strains. The antibodies are able to protect prophylactically and therapeutically a subject (e.g., a mouse as shown in the examples below) against a lethal challenge with an influenza virus, such as A/California/04/2009 H1N1 (pH1N1). Each of the antibodies binds to a conserved epitope region of the HA globular head near the receptor binding site (RBS) different than that previously described to other cross-reactive H1 mAbs. More specifically, these antibodies recognize a highly conserved, novel discontinuous (or conformational) epitope in the HA1 globular head of H1 influenza strains that dependent on residues within the Sa antigenic site (K180) and near the Ca antigenic site (E129), encompassing a region near the RBS.

As disclosed herein, in an effort to identify HA epitopes that if targeted may confer universally protective humoral immunity as well as generate human monoclonal antibodies (hmAbs) that may have broad spectrum activity, the inventors examined plasmablasts from a subject that was immunized with the 2014-2015 seasonal inactivated influenza vaccine. It was unexpected that, using combined deep immunoglobulin repertoire sequencing and single-cell immunoglobulin cloning, hmAbs (such as a KPF1 antibody as described in details below) with broad and potent neutralizing activity against H1 influenza viruses were obtained. The neutralization titer 50 (NT50) of the antibody can be as low as less than 10.0, 5.0, 1.0, 0.5, 0.10, 0.05, 0.04, 0.03, or 0.02 µg/ml. Most of the binding (~50-70%) to HA can be maintained even in 8M Urea indicating high avidity.

As disclosed herein, an antibody of this invention can recognize a large number of H1 isolates, including one, two, three, four, or five of A/California/07/2009 H1N1, A/New Caledonia/20/1999 H1N1, A/Texas/36/1991 H1N1, A/South Carolina/01/1918 H1N1, and A/Puerto Rico/08/1934 H1N1. For example, KPF1 recognized 83% of all H1 isolates tested, including 1918 H1. In some embodiment, the antibody does not recognize A/USSR/1977 H1N1 at 1 µg/ml, od has no reactivity against H3 or B HAs.

It was unexpected that in vivo, the antibody of this invention (e.g., KPF1) can prophylactically result in a high percentage (e.g., 50%, 60%, 70%, 80%, 90%, 95% or 100%) survival of mice from lethal A/California/07/2009 H1N1 challenge in the manner tested as shown in the examples below. Also unexpected, when given as late as 72 h after lethal challenge, an antibody of this invention (e.g., KPF1) can result in a high percentage (e.g., 40%, 50%, 60%, 70%, or 80%) survival. The antibody of this invention (e.g., KPF1) recognizes an epitope in the HA globular head that is dependent on residues within the Sa antigenic site and near the receptor binding site.

As a number of recent mAbs that have broader reactivity against multiple influenza virus strains are HA stalk-specific, it was unexpected that antibodies of this invention, which recognize an epitope in the HA globular head, can neutralize multiple influenza virus strains. As disclosed herein, an antibody of this invention (such as KPF1) has more potent neutralizing anti-influenza activities.

Listed below are amino acid sequences of the heavy chain (HC) variable regions and light chain (LC) variable regions of one exemplary antibody, the KPF1 antibody mentioned above, where the heavy chain CDR1-3 (HCDR1, HCDR2, and HCDR3) and light chain CDR1-3(LCDR1, LCDR2, and LCDR3) are in bold.

| Name | Sequence | SEQ ID NO: |
|---|---|---|
| heavy chain variable region | EVQLLESGGGLVQPGGSLRISCAASGSTFGDFA MSWVRQSPGRGLEWVSVTSAGGDRTYYADSVKG RFTISRDNSKNTLYLQMNSLRGEDTAMYYCARL DSSGFHYGRPGRNWGQGTLVTVSS | 1 |
| kappa light chain variable region | DIQMTHSPPSLSASVGDRITITCQASQDISYYL IWYQQKPGKAPKPLIYDASNLEAGVPSRFSASG SGTDFTLTISSLQPEDLATYYCQQYKSLPYTFG QGTKLEIK | 2 |
| HCDR1 | GSTFGDFA | 3 |
| HCDR2 | TSAGGDRT | 4 |
| HCDR3 | ARLDSSGFHYGRPGRN | 5 |
| LCDR1 | QDISYY | 6 |
| LCDR2 | DAS | 7 |
| LCDR3 | QQYKSLPYT | 8 |
| kappa | DIQMTHSPPSLSASVGDRITITCQASQDISYYL | 9 |

| Name | Sequence | SEQ ID NO: |
|---|---|---|
| light chain variable region | IWYQQKPGKAPKPLIYDASNLEAGVPSRFSASG SGTDFTLTISSLQPEDLATYYCQQYKSLPYT | 5 |
| heavy chain germline | EVQLLESGGGLVQPGGSLRLSCAASGFTFSSYA MSWVRQAPGKGLEWVSAISGSGGSTYYADSVKG RFTISRDNSKNTLYLQMNSLRAEDTAVYYCARL DSSGYYYGRPGRNWGQGTLVTVSS | 10 |
| kappa light chain germline | DIQMTQSPSSLSASVGDRVTITCQASQDISNYL NWYQQKPGKAPKLLIYDASNLETGVPSRFSGSG SGTDFTFTISSLQPEDIATYYCQQYDNLPYT | 11 |

As mentioned above, a key vulnerability in protection from influenza infection is the need for annual selection of vaccine composition to adequately match expected strains for the upcoming season. The propensity of influenza for antigenic drift and shift, and its tendency to elicit predominantly strain specific antibodies leaves humanity susceptible to waves of new viral strains with pandemic potential for which limited or no immunity may exist.

Shown below are the nucleotide and amino acid sequences of the hemagglutinin (HA) proteins of some examples of these influenza isolates, including the 2014-2015 Fluzone vaccine. A/California/07/2009 X-179A (H1N1), A/Texas/50/2012 X-223A (H3N2), B/Massachusetts/02/2012 (B Yamagata lineage), and B/Brisbane/60/2008 (Victoria lineage).

```
A/California/7/2009 H1N1
Nucleotide sequence (SEQ ID NO: 12):
atgaaggcaa tactagtagt tctgctatat acatttgcaa ccgcaaatgc agacacatta tgtataggtt atcatgcgaa caattcaaca gacactgtag acacagtact agaaaagaat gtaacagtaa cacactctgt taaccttcta gaagacaagc ataacgggaa actatgcaaa ctaagagggg tagccccatt gcatttgggt aaatgtaaca ttgctggctg gatcctggga aatccagagt gtgaatcact ctccacagca agctcatggt cctacattgt ggaaacacct agttcagaca atggaacgtg ttacccagga gatttcatcg attatgagga gctaagagag caattgagct cagtgtcatc atttgaaagg tttgagatat tccccaagac aagttcatgg cccaatcatg actcgaacaa aggtgtaacg gcagcatgtc ctcatgctgg agcaaaaagc ttctacaaaa atttaatatg gctagttaaa aaggaaatt catcccaaa gctcagcaaa tcctacatta atgataaagg gaaagaagtc ctcgtgctat ggggcattca ccatccatct actagtgctg accaacaaag tctctatcag aatgcagatg catatgtttt tgtggggtca tcaagataca gcaagaagtt caagccggaa atagcaataa gacccaaagt gagggatcaa gaagggagaa tgaactatta ctggacacta gtagagccgg gagacaaaat aacattcgaa gcaactggaa atctagtggt accgagatat gcattcgcaa tggaaagaaa tgctggatct ggtattatca tttcagatac accagtccac gattgcaata acttgtca aacacccaag ggtgctataa acaccagcct cccatttcag aatatacatc cgatcacaat tggaaaatgt ccaaaatatg taaaaagcac aaaattgaga ctggccacag gattgaggaa tatcccgtct attcaatcta gaggcctatt tggggccatt gccggtttca ttgaagggg gtggacaggg atggtagatg gatggtacgg ttatcaccat caaaatgagc aggggtcagg atatgcagcc gacctgaaga gcacacagaa tgccattgac gagattacta acaaagtaaa ttctgttatt gaaaagatga atacagtt cacagcagta ggtaaagagt caaccaccct ggaaaaaaga atagagaatt taaataaaaa agttgatgat ggtttcctgg acatttggac ttacaatgcc gaactgttgg ttctattgga aaatgaaaga actttggact accacgattc aaatgtgaag aacttatatg aaaaggtaag aagccagcta aaaacaatg ccaaggaaat tggaaacggc tgctttgaat tttaccacaa atgcgataac acgtgcatgg aaagtgtcaa aatgggact tatgactacc caaaatactc agaggaagca aaattaaaca gagaagaaat agatgggta aagctggaat caacaaggat ttaccagatt ttggcgatct attcaactgt cgccagttca
```

-continued ttggtactgg tagtctccct gggggcaatc agtttctgga tgtgctctaa tgggtctcta cagtgtagaa tatgtattta a Protein sequence (SEQ ID NO: 13):
MKAILVVLLYTFATANADTLCIGYHANNSTDTVDTVLEKNVTVTHSVNLLEDKHNGKLCKLRGVAPLHLGKCNIA

GWILGNPECESLSTASSWSYIVETPSSDNGTCYPGDFIDYEELREQLSSVSSFERFEIFPKTSSWPNHDSNKGVT

AACPHAGAKSFYKNLIWLVKKGNSYPKLSKSYINDKGKEVLVLWGIHHPSTSADQQSLYQNADAYVFVGSSRYSK

KFKPEIAIRPKVRDQEGRMNYYWTLVEPGDKITFEATGNLVVPRYAFAMERNAGSGIIISDTPVHDCNTTCQTPK

GAINTSLPFQNIHPITIGKCPKYVKSTKLRLATGLRNIPSIQSRGLFGAIAGFIEGGWTGMVDGWYGYHHQNEQG

SGYAADLKSTQNAIDEITNKVNSVIEKMNTQFTAVGKEFNHLEKRIENLNKKVDDGFLDIWTYNAELLVLLENER

TLDYHDSNVKNLYEKVRSQLKNNAKEIGNGCFEFYHKCDNTCMESVKNGTYDYPKYSEEAKLNREEIDGVKLEST

RIYQILAIYSTVASSLVLVVSLGAISFWMCSNGSLQCRICI (Underlined and bold: E129 and K180)

A/Texas/50/2012 (H3N2)
Nucleotide sequence (SEQ ID NO: 14):
atgaagacta tcattgcttt gagctacatt ctatgtctgg ttttcgctca aaaacttcct ggaaatgaca atagcacggc aacgctgtgc cttgggcacc atgcagtacc aaacggaacg atagtgaaaa caatcacgaa tgaccgaatt gaagttacta atgctactga actggttcag aattcctcaa taggtgaaat atgcgacagt cctcatcaga tccttgatgg agaaaactgc acactaatag atgctctatt gggagaccct cagtgtgatg gcttccaaaa taagaaatgg gaccttttg ttgaacgaag caaagcctac agcaactgtt acccttatga tgtgccggat tatgcctccc ttaggtcact agttgcctca tccggcacac tggagtttaa caatgaaagc ttcaattgga atggagtcac tcaaaacgga acaagttctg cttgcataag agatctaat aatagtttct ttagtagatt aaattggttg acccacttaa acttcaaata cccagcattg aacgtgacta tgccaaacaa tgaacaattt gacaaattgt acatttgggg ggttcaccac ccggttacgg acaaggacca atcttcctg tatgctcaac catcaggaag aatcacagta tctaccaaaa gaagccaaca agctgtaatc ccgaatatcg gatttagacc cagaataagg aataaccta gcagaataag catctattgg acaatagtaa aaccgggaga cattactttg attaacagca cagggaatct aattgctcct aggggttact tcaaaatacg aagtgggaaa agctcaataa tgagatcaga tgcacccatt ggcaaatgca gtctgaatg catcactcca aatggaagca ttcccaatga caaaccattc caaaatgtaa acaggatcac atacggggcc tgtcccagat atgttaagca agcactctg aaattggcaa caggaatgcg aatgtacca gagaaacaaa ctagaggcat atttggcgca atagcgggtt tcatagaaaa tggttgggag ggaatggtgg atggttggta cggtttcagg catcaaaatt ctgagggaag aggacaagca gcagatctca aaagcactca agcagcaatc gatcaaatca tgggaagct gaatcgattg atcgggaaaa ccaacgagaa attccatcag attgaaaaag aattctcaga gtagaaggg agaattcagg accttgagaa atatgttgag gacactaaaa tagatctctg gtcatacaac gcggagcttc ttgttgccct ggagaaccaa catacaattg atctaactga ctcagaaatg aacaaactgt ttgaaaaaac aaagaagcaa ctgagggaaa atgctgagga tatgggcaat ggttgtttca aaatatacca caaatgtgac aatgcctgca taggatcaat cagaaatgga acttatgacc acgatgtata cagagatgaa gcattaaaca accggttcca gatcaaggga gttgagctga agtcagggta caaagattgg atcctatgga tttcctttgc catatcatgt tttttgcttt gtgttgcttt gttggggttc atcatgtggg cctgccaaaa gggcaacatt

```
aggtgcaaca tttgcatttg a
```

Protein sequence (SEQ ID NO: 15):
MKTIIALSYILCLVFAQKLPGNDNSTATLCLGHHAVPNGTIVKTITNDRIEVTNATELVQNSSIGEICDSPHQIL
DGENCTLIDALLGDPQCDGFQNKKWDLFVERSKAYSNCYPYDVPDYASLRSLVASSGTLEFNNESFNWNGVTQNG
TSSACIRRSNNSFFSRLNWLTHLNFKYPALNVTMPNNEQFDKLYIWGVHHPVTDKDQIFLYAQPSGRITVSTKRS
QQAVIPNIGFRPRIRNNPSRISIYWTIVKPGDILLINSTGNLIAPRGYFKIRSGKSSIMRSDAPIGKCKSECITP
NGSIPNDKPFQNVNRITYGACPRYVKQSTLKLATGMRNVPEKQTRGIFGAIAGFIENGWEGMVDGWYGFRHQNSE
GRGQAADLKSTQAAIDQINGKLNRLIGKTNEKFHQIEKEFSEVEGRIQDLEKYVEDTKIDLWSYNAELLVALENQ
HTIDLTDSEMNKLFEKTKKQLRENAEDMGNGCFKIYHKCDNACIGSIRNGTYDHDVYRDEALNNRFQIKGVELKS
GYKDWILWISFAISCFLLCVALLGFIMWACQKGNIRCNICI B/Massachusetts/02/2012 (B Yamagata lineage)
Nucleotide sequence (SEQ ID NO: 16):
```
atgaaggcaa taattgtact actaatggta gtaacatcca atgcagatcg aatctgcact
gggataacat cttcaaactc acctcatgtg gtcaaaacag ctactcaagg ggaggtcaat
gtgactggtg tgataccact aacaacaaca ccaacaaaat cttattttgc aaatctcaaa
ggaacaaaga ccagagggaa actatgccca gactgtctca actgtacaga tctggatgtg
gccctgggca ggccaatgtg tgtgggaact acaccttctg cgaaagcttc aatacttcac
gaagtcagac ctgttacatc cggtgcttc cctataatgc acgacagaac aaaaatcagg
caactagcca atcttctcag aggatatgaa aatatcaggt tatcaaccca aaacgttatc
gatgcagaaa aggcaccagg aggaccctac agacttggaa cctcaggatc ttgccctaac
gctaccagta aaagcggatt tttcgcaaca atggcttggg ctgtcccaaa ggacaacaac
aaaaatgcaa cgaacccatt aacagtagaa gtaccataca tttgtgcaga aggggaagac
caaattactg tttgggggtt ccattcagat gacaaaaccc aaatgaagaa cctctatgga
gactcaaatc ctcaaaagtt cacctcatct gctaatggag taaccacaca ttatgtttct
cagattggcg gcttcccaga tcaaacagaa gacggaggac taccacaaag cggcagaatt
gtcgttgatt acatgatgca aaaacctggg aaaacaggaa caattgtcta tcaaagaggt
gttttgttgc ctcaaaaggt gtggtgcgcg agtggcagga gcaaagtaat aaaagggtcc
ttgcctttaa ttggtgaagc agattgcctt catgaaaaat acggtggatt aaacaaaagc
aagccttact acacaggaga acatgcaaaa gccataggaa attgcccaat gggtgaaaa
acacctttga gcttgccaa tggaaccaaa tatagacctc ctgcaaaact attaaaggaa
aggggtttct tcggagctat tgctggtttc ctagaaggag gatgggaagg aatgattgca
ggttggcacg gatacacatc tcacggagca catggagtgg cagttgctgc agaccttaag
agcacacaag aagctataaa caagataaca aaaaatctca actctttgag tgagctagaa
gtaaagaatc ttcaaaggct aagtggtgcc atgatgaac tccacaacga aatactcgag
ctggatgaga agtggatga cctcagagct gacactataa gttcacaaat agaacttgca
gtcttgcttt ccaacgaagg aataataaac agtgaagacg agcatctatt ggcacttgag
agaaaactaa agaaaatgct gggtccctct gctgtagaca taggaaatgg atgcttcgaa
accaaacaca atgcaaccca gacctgctta gacaggatag ctgctggcac ctttaatgca
ggagagtttt ctctccccac ttttgattca ttgaacatta tgctgcatc tttaaatgat
gatggattgg ataaccatac tatactgctc tattactcaa ctgctgcttc tagtttggct
gtaacattga tgctagctat ttttattgtt tatatggtct ccagagacaa cgtttcatgc
tccatctgtc tataa
```

-continued

Protein sequence (SEQ ID NO: 17):
MKAIIVLLMVVTSNADRICTGITSSNSPHVVKTATQGEVNVTGVIPLTTTPTKSYFANLKGTKTRGKLCPDCLNC

TDLDVALGRPMCVGTTPSAKASILHEVRPVTSGCFPIMHDRTKIRQLANLLRGYENIRLSTQNVIDAEKAPGGPY

RLGTSGSCPNATSKSGFFATMAWAVPKDNNKNATNPLTVEVPYICAEGEDQITVWGFHSDDKTQMKNLYGDSNPQ

KFTSSANGVTTHYVSQIGGFPDQTEDGGLPQSGRIVVDYMMQKPGKTGTIVYQRGVLLPQKVWCASGRSKVIKGS

LPLIGEADCLHEKYGGLNKSKPYYTGEHAKAIGNCPIWVKTPLKLANGTKYRPPAKLLKERGFFGAIAGFLEGGW

EGMIAGWHGYTSHGAHGVAVAADLKSTQEAINKITKNLNSLSELEVKNLQRLSGAMDELHNEILELDEKVDDLRA

DTISSQIELAVLLSNEGIINSEDEHLLALERKLKKMLGPSAVDIGNGCFETKHKCNQTCLDRIAAGTFNAGEFSL

PTFDSLNITAASLNDDGLDNHTILLYYSTAASSLAVTLMLAIFIVYMVSRDNVSCSICL

B/Brisbane/60/2008 (Victoria lineage)
Nucleotide sequence (SEQ ID NO: 18):
```
    atgaagg caataattgt actactcatg gtagtaacat ccaatgcaga tcgaatctgc actgggataa catcgtcaaa ctcaccacat gtcgtcaaaa ctgctactca aggggaggtc aatgtgactg gtgtaatacc actgacaaca cacccacca aatctcattt tgcaaatctc aaaggaacag aaaccagggg gaaactatgc ccaaaatgcc tcaactgcac agatctggac gtagccttgg gcagaccaaa atgcacgggg aaaataccct cggcaagagt ttcaatactc catgaagtca gacctgttac atctgggtgc tttcctataa tgcacgacag aacaaaaatt agacagctgc ctaaccttct ccgaggatac gaacatatca ggttatcaac ccataacgtt atcaatgcag aaaatgcacc aggaggaccc tacaaaattg gaacctcagg gtcttgccct aacattacca atggaaacgg attttttcgca acaatggctt gggccgtccc aaaaaacgac aaaaacaaaa cagcaacaaa tccattaaca atagaagtac catacatttg tacagaagga gaagaccaaa ttaccgtttg ggggttccac tctgacaacg agacccaaat ggcaaagctc tatggggact caaagcccca gaagttcacc tcatctgcca acggagtgac cacacattac gtttcacaga ttggtggctt cccaaatcaa acagaagacg gaggactacc acaaagtggt agaattgttg ttgattacat ggtgcaaaaa tctgggaaaa caggaacaat tacctatcaa agggtatttt tattgcctca aaaggtgtgg tgcgcaagtg gcaggagcaa ggtaataaaa ggatccttgc ctttaattgg agaagcagat tgcctccacg aaaaatacgg tggattaaac aaaagcaagc cttactacac aggggaacat gcaaaggcca taggaaattg cccaatatgg gtgaaaacac ccttgaagct ggccaatgga accaaatata gacctcctgc aaaactatta aaggaaaggg gtttcttcgg agctattgct ggtttcttag aaggaggatg ggaaggaatg attgcaggtt ggcacggata cacatcccat ggggcacatg gagtagcggt ggcagcagac cttaagagca ctcaagaggc cataaacaag ataacaaaaa atctcaactc tttgagtgag ctggaagtaa agaatcttca agactaagc ggtgccatgg atgaactcca caacgaaata ctagaactag atgagaaagt ggatgatctc agagctgata caataagctc acaaatagaa ctcgcagtcc tgcttttccaa tgaaggaata ataaacagtg aagatgaaca tctcttggcg cttgaaagaa agctgaagaa aatgctgggc ccctctgctg tagagatagg gaatggatgc tttgaaacca aacacaagtg caaccagacc tgtctcgaca gaatagctgc tggtaccttt gatgcaggag aatttctctc ccccacctt gattcactga atattactgc tgcatcttta aatgacgatg gattggataa tcatactata ctgctttact actcaactgc tgcctccagt
```
Protein sequence (SEQ ID NO: 19):
MKAIIVLLMVVTSNADRICTGITSSNSPHVVKTATQGEVNVTGVIPLTTTPTKSHFANLKGTETRGKLCPKCLNC

TDLDVALGRPKCTGKIPSARVSILHEVRPVTSGCFPIMHDRTKIRQLPNLLRGYEHIRLSTHNVINAENAPGGPY

-continued

KIGTSGSCPNITNGNGFFATMAWAVPKNDKNKTATNPLTIEVPYICTEGEDQITVWGFHSDNETQMAKLYGDSKP

QKFTSSANGVTTHYVSQIGGFPNQTEDGGLPQSGRIVVDYMVQKSGKTGTITYQRGILLPQKVWCASGRSKVIKG

SLPLIGEADCLHEKYGGLNKSKPYYTGEHAKAIGNCPIWVKTPLKLANGTKYRPPAKLLKERGFFGAIAGFLEGG

WEGMIAGWHGYTSHGAHGVAVAADLKSTQEAINKITKNLNSLSELEVKNLQRLSGAMDELHNEILELDEKVDDLR

ADTISSQIELAVLLSNEGIINSEDEHLLALERKLKKMLGPSAVEIGNGCFETKHKCNQTCLDRIAAGTFDAGEFS

LPTFDSLNITAASLNDDGLDNHTILLYYSTAASS

Shown below are the nucleotide and the amino acid sequence of the pH1N1 HA.

Nucleotide sequence (SEQ ID NO: 20):
AGCAAAAGCAGGGGAAAATAAAAGCAACAAAAATGAAGGCAATACTAGTAGTTCTGCTATATACATTTGCAACC

GCAAATGCAGACACATTATGTATAGGTTATCATGCGAACAATTCAACAGACACTGTAGACACAGTACTAGAAAA

GAATGTAACAGTAACACACTCTGTTAACCTTCTAGAAGACAAGCATAACGGGAAACTATGCAAACTAAGAGGGG

TAGCCCCATTGCATTTGGGTAAATGTAACATTGCTGGCTGGATCCTGGGAAATCCAGAGTGTGAATCACTCTCC

ACAGCAAGCTCATGGTCCTACATTGTGGAAACACCTAGTTCAGACAATGGAACGTGTTACCCAGGAGATTTCAT

CGATTATGAGGAGCTAAGAGAGCAATTGAGCTCAGTGTCATCATTTGAAAGGTTTGAGATATTCCCCAATACAA

GTTCATGGCCCAATCATGACTCGAACAAAGGTGTAACGGCAGCATGTCCTCATGCTGGAGCAAAAAGCTTCTAC

AAAAATTTAATATGGCTAGTTAAAAAAGGAAATTCATACCCAAAGCTCAGCAAATCCTACATTAATGATAAAGG

GAAAGAAGTCCTCGTGCTATGGGGCATTCACCATCCACCTACTAGTGCTGACCAACAAAGTCTCTATCAGAATG

CAGATACATATGTTTTTGTGGGGTCATCAAGATACAGCAAGAAGTTCAAGCCGGAAATAGCAATAAGACCCAAA

GTGAGGGGTCAAGAAGGGAGAATGAACTATTACTGGACACTAGTAGAGCCGGGAGACAAAATAACATTCGAAGC

AACTGGAAATCTAGTGGTACCGAGATATGCATTCGCAATGGAAAGAAATGCTGGATCTGGTATTATCATTTCAG

ATACACCAGTCCACGATTGCAATACAACTTGTCAAACACCCAAGGGTGCTATAAACACCAGCCTCCCATTTCAG

AATATACATCCGATCACAATTGGAAAATGTCCAAAATATGTAAAAAGCACAAAATTGAGACTGGCCACAGGATT

GAGGAATATCCCGTCTATTCAATCTAGAGGCCTATTTGGGGCCATTGCCGGTTTCATTGAAGGGGGGTGGACAG

GGATGGTAGATGGATGGTACGGTTATCACCATCAAAATGAGCAGGGGTCAGGATATGCAGCCGACCTGAAGAGC

ACACAGAATGCCATTGACGAGATTACTAACAAAGTAAATTCTGTTATTGAAAAGATGAATACACAGTTCACAGC

AGTAGGTAAAGAGTTCAACCACCTGGAAAAAAGAATAGAGAATTTAAATAAAAAAGTTGATGATGGTTTCCTGG

ACATTTGGACTTACAATGCCGAACTGTTGGTTCTATTGGAAAATGAAAGAACTTTGGACTACCACGATTCAAAT

GTGAAGAACTTATATGAAAAGGTAAGAAGCCAGCTAAAAAACAATGCCAAGGAAATTGGAAACGGCTGCTTTGA

ATTTTACCACAAATGCGATAACACGTGCATGGAAAGTGTCAAAAATGGGACTTATGACTACCCAAAATACTCAG

AGGAAGCAAAATTAAACAGAGAAGAAATAGATGGGGTAAAGCTGGAATCAACAAGGATTTACCAGATTTTGGCG

ATCTATTCAACTGTCGCCAGTTCATTGGTACTGGTAGTCTCCCTGGGGGCAATCAGTTTCTGGATGTGCTCTAA

TGGGTCTCTACAGTGTAGAATATGTATTTAACATTAGGATTTCAGAAGCATGAGAAAAACACCCTTGTTTCTAC

T

ORF underlined.
ATG and Stop codons indicated in bold.

Amino acid sequence (SEQ ID NO: 21):
MKAILVVLLYTFATANADTLCIGYHANNSTDTVDTVLEKNVTVTHSVNLLEDKHNGKLCKLRGVAPLHLGKCNI

AGWILGNPECESLSTASSWSYIVETPSSDNGTCYPGDFIDYEELREQLSSVSSFERFEIFPNTSSWPNHDSNKG

VTAACPHAGAKSFYKNLIWLVKKGNSYPKLSKSYINDKGKEVLVLWGIHHPPTSADQQSLYQNADTYVFVGSSR

-continued

```
YSKKFKPEIAIRPKVRGQEGRMNYYWTLVEPGDKITFEATGNLVVPRYAFAMERNAGSGIIISDTPVHDCNTTC

QTPKGAINTSLPFQNIHPITIGKCPKYVKSTKLRLATGLRNIPSIQSRGLFGAIAGFIEGGWTGMVDGWYGYHH

QNEQGSGYAADLKSTQNAIDEITNKVNSVIEKMNTQFTAVGKEFNHLEKRIENLNKKVDDGFLDIWTYNAELLV

LLENERTLDYHDSNVKNLYEKVRSQLKNNAKEIGNGCFEFYHKCDNTCMESVKNGTYDYPKYSEEAKLNREEID

GVKLESTRIYQILAIYSTVASSLVLVVSLGAISFWMCSNGSLQCRICI
```

Antibodies disclosed herein (e.g., hmAb KPF1) have broad activity against H1 influenza isolates and potent prophylactic and therapeutic activity in vivo, which is mediated by recognition of conserved residues in the H1 hemagglutinin globular head. Each of the antibodies is highly specific to influenza H1 HA and recognizes all H1 isolates tested with the exception of A/USSR/1977, likely due to the unique HA structure of this pandemic isolate (Kilbourne ED. 2006. Emerg Infect Dis 12:9-14; and Rozo M, et al. 2015. MBio 6). The high potency of the antibody, such as KPF1, is demonstrated in vitro by its neutralizing and HAI activities below 1.0 μg/ml (FIG. 4), its ability to maintain HA binding in the presence of urea, and its high avidity and affinity (FIG. 2). Few hmAbs have been reported that have similar in vitro neutralizing activity of H1 influenza below 1 μg/ml (Sparrow E, et al. 2016. Vaccine 34:5442-5448; Whittle J R, et al. 2011. Proc Natl Acad Sci USA 108:14216-14221; Krause J C, et al. 2011. J Virol 85:10905-10908; Ren H, et al. 2016. Curr Opin Immunol 42:83-90; Lee P S, et al. 2012. Proc Natl Acad Sci USA 109:17040-17045; Yoshida R, et al. 2009. PLoS Pathog 5:e1000350; Ekiert D C, et al. 2012. Nature 489:526-532; and Yu X, et al. 2008. Nature 455:532-536), highlighting the unique potency of the antibody of this invention, such as KPF1.

The potent activity of the antibody of this invention, such as KPF1, extends to its ability to protect and treat H1 infection in vivo (FIGS. 5 and 6). For example, the challenge dose of 10×MLD$_{50}$ pH1N1 used in the study shown below exceeded by 2 to 5 fold that which has been used by others (Heaton N S, et al. 2013. J Virol 87:8272-8281; Wang S F, et al. 2016. Dev Comp Immunol doi:10.1016/j.dci.2016.10.010; Marjuki H, et al. 2016. J Virol 90:10446-10458; Song A, et al. 2014. Antiviral Res 111:60-68; DiLillo D J, et al. 2014. Nat Med 20:143-151; and Wrammert J, et al. 2011. J Exp Med 208:181-193) to evaluate the in vivo activity of mAbs against H1 influenza. With this high dose challenge of pH1N1, 1 mg/kg of an antibody of this invention, such as KPF1, completely protected from infection in a prophylactic model (FIG. 5), and treatment with 10 mg/kg administered as late as 72 h p.i. significantly enhanced survival (FIG. 6). Remarkably, KPF1 was able to protect against the lethal challenge of multiple H1 influenza virus strains (FIG. 5). The true potential of the antibody for treatment of influenza H1 infections may be underestimated as the dose of KPF1 or delay in treatment have not yet been further evaluated. Together these results suggest the in vitro and in vivo activity of the antibody of this invention, such as KPF1, against H1 influenza is not bested to date by other mAbs.

The antibody of this invention, such as KPF1, recognizes a highly conserved novel epitope (FIG. 8) in the HA1 globular head of H1 influenza strains that dependent on the E129 residue near the Ca and Cb antigenic sites (FIG. 7). The hmAb 2D1, which recognizes both 1918 and pH1N1 HA1 but has limited activity against most influenza H1 strains, recognizes an epitope centered on Sa which includes K180 (Xu R, et al. 2010. Science 328:357-360), and selected for escape mutants at this residue (Krause J C, et al. 2010. J Virol 84:3127-3130). 2D1 was not reported to interact with E129, suggesting the precise epitopes recognized by the antibody of this invention, such as KPF1, are distinct than those of 2D1. The mouse mAb GC0587, which was generated from pH1N1 immunized mice is H1-specific and recognizes an epitope that contains both E129 and K180 residues (Cho K J, et al. 2014. PLoS One 9:e89803). However, its lack of reactivity against 1918 H1 (Cho K J, et al. 2014. PLoS One 9:e89803) in contrast to the antibody of this invention, such as KPF1, suggesting incomplete congruence in the epitopes recognized by both mAbs. Although viral neutralization is thought to be the major protective function of H1 specific Ab, the ability of H1 specific Abs to substantially contribute to Fc-mediated mechanisms of viral clearance such as Ab-dependent cell-mediated cytotoxicity (ADCC) and complement-dependent cytotoxicity (CDC) remains possible (DiLillo D J, et al. 2014. Nat Med 20:143-151; Chai N, et al. 2017. Nat Commun 8:14234; and Srivastava V, et al. 2013. J Virol 87:5831-5840). Interestingly the E129 residue is located within an ADCC epitope that has been previously described (Srivastava V, et al. 2013. J Virol 87:5831-5840), suggesting evaluating the Fc-mediated activities of the antibody of this invention are warranted. Overall, these results suggest that the epitope recognized by the antibody of this invention is broadly conserved in H1 strains, and recognition of this epitope can mediate neutralizing and HAI, and potentially ADCC activity. Further resolution of the epitope and assessment of its potential as an immunogen to induce broad protection from H1 influenza is pursued.

The in vitro and in vivo activity profile of the antibody of this invention, such as KPF1, as well as the E129 amino acid conservation, suggests it has therapeutic value for the treatment and prevention of H1 influenza infections. Although several hmAbs targeting HA stem epitopes have been identified that have broadly neutralizing activity against multiple influenza types and subtypes, their potency is commonly less than hmAbs targeting the HA globular head, and their clinical efficacy has yet to be determined. Historically, influenza viruses causing pandemics have been subtype specific (e.g. H1N1, H2N2 or H3N2) and, therefore, having more potent globular head broadly neutralizing antibodies rather than less specific and less potent neutralizing stalk reactive antibodies represents a better approach for pandemic preparedness. Accordingly, a cocktail of multiple high affinity type-specific hmAbs (including the antibody of this invention, such as KPF1), collectively conferring universal breadth and protection through recognition of several epitopes may ultimately be an effective clinical therapeutic for influenza infection.

Fragment

In certain embodiments, an antibody provided herein is an antibody fragment. Antibody fragments include, but are not limited to, Fab, Fab', Fab'-SH, F(ab)$_2$, Fv, and scFv fragments, and other fragments described below, e.g., diabodies. triabodies tetrabodies, and single-domain antibodies. For a review of certain antibody fragments, see Hudson et al., Nat. Med. 9:129-134 (2003). For a review of scFv fragments, see, e.g., Pluckthun, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab)$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516).

Antibody fragments can be made by various techniques, including but not limited to proteolytic digestion of an intact antibody as well as production by recombinant host cells (e.g., *E. coli* or phage), as described herein.

Chimeric and Humanized Antibodies

In certain embodiments, an antibody provided herein is a chimeric antibody. Certain chimeric antibodies are described, e.g., in U.S. Pat. No. 4,816,567; and Morrison et al., Proc. Natl. Acad. Sci. USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing specificity determining region (SDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

Human Antibodies

In certain embodiments, an antibody provided herein is a human antibody. Human antibodies can be produced using various techniques known in the art or using techniques described herein. Human antibodies are described generally in van Dijk and van de Winkel, Curr. Opin. Pharmacol. 5: 368-74 (2001) and Lonberg, Curr. Opin. Immunol. 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENOMOUSE technology; U.S. Pat. No. 5,770,429 describing HUMAB technology; U.S. Pat. No. 7,041,870 describing K-M MOUSE technology, and U.S. Patent Application Publication No. US 2007/0061900, describing VELOCIMOUSE technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).) Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in Methods in Molecular Biology 178: 1-37 (O'Brien et al., ed., Human Press, Totowa, N.J., 2001) and further described, e.g., in the McCafferty et al., Nature 348:552-554; Clackson et al., Nature 352: 624-628 (1991); Marks et al., J. Mol. Biol. 222: 581-597 (1992); Marks and Bradbury, in Methods in Molecular Biology 248:161-175 (Lo, ed., Human Press, Totowa, N.J., 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., Ann. Rev. Immunol., 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., EMBO J, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, J. Mol. Biol., 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360. Antibodies or antibody fragments isolated from human antibody libraries are considered human antibodies or human antibody fragments herein.

Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

Substitution, Insertion, and Deletion Variants

In certain embodiments, antibody variants having one or more amino acid substitutions are provided. Sites of interest for substitutional mutagenesis include the HVRs and FRs. Conservative substitutions are defined herein. Amino acid substitutions may be introduced into an antibody of interest and the products screened for a desired activity, e.g., retained/improved antigen binding, decreased immunogenicity, or improved ADCC or CDC.

Accordingly, an antibody of the invention can comprise one or more conservative modifications of the CDRs, heavy chain variable region, or light variable regions described herein, e.g., SEQ ID NOs: 1-8. A conservative modification or functional equivalent of a peptide, polypeptide, or protein disclosed in this invention refers to a polypeptide derivative of the peptide, polypeptide, or protein, e.g., a protein having one or more point mutations, insertions, deletions, truncations, a fusion protein, or a combination thereof. It retains substantially the activity to of the parent peptide, polypeptide, or protein (such as those disclosed in this invention). In general, a conservative modification or functional equivalent is at least 60% (e.g., any number between 60% and 100%, inclusive, e.g., 60%, 70%, 75%, 80%, 85%, 90%, 95%, 96%, 97%, 98%, and 99%) identical to a parent (e.g., one of SEQ ID NOs: 1-8). Accordingly, within scope of this invention are heavy chain variable region or light variable regions having one or more point mutations, insertions, deletions, truncations, a fusion protein, or a combination thereof, as well as antibodies having the variant regions.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package, using either a BLOSSUM 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can further be used as a "query sequence" to perform a search against public databases to, for example, identify related sequences. Such searches can be performed using the XBLAST program (version 2.0) of Altschul, et al. (1990) J. Mol. Biol. 215:403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used.

As used herein, the term "conservative modifications" refers to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include:

amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

Non-conservative substitutions will entail exchanging a member of one of these classes for another class.

An exemplary substitutional variant is an affinity matured antibody, which may be conveniently generated, e.g., using phage display-based affinity maturation techniques such as those described in e.g., Hoogenboom et al., in Methods in Molecular Biology 178:1-37 (O'Brien et al., ed., Human Press, Totowa, N.J., (2001). Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Glycosylation of the constant region on N297 may be prevented by mutating the N297 residue to another residue, e.g., N297A, and/or by mutating an adjacent amino acid, e.g., 298 to thereby reduce glycosylation on N297.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies described herein to thereby produce an antibody with altered glycosylation. For example, EP 1,176,195 by Hanai et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Led 3 cells, with reduced ability to attach fucose to Asn(297)-linked carbohydrates, also resulting in hypofucosylation of antibodies expressed in that host cell (see also Shields, R. L. et al. (2002) J. Biol. Chem. 277:26733-26740). PCT Publication WO 99/54342 by Umana et al. describes cell lines engineered to express glycoprotein-modifying glycosyl transferases (e.g., beta(1, 4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) Nat. Biotech. 17: 176-180).

Fc Region Variants

The variable regions of the antibody described herein can be linked (e.g., covalently linked or fused) to an Fc, e.g., an IgG1, IgG2, IgG3 or IgG4 Fc, which may be of any allotype or isoallotype, e.g., for IgG1: G1m, G1m1(a), G1m2(x), G1m3(f), G1m17(z); for IgG2: G2m, G2m23(n); for IgG3: G3m, G3m21(g1), G3m28(g5), G3m1 1(b0), G3m5(b1), G3m13(b3), G3m14(b4), G3m10(b5), G3m15(s), G3m16 (t), G3m6(c3), G3m24(c5), G3m26(u), G3m27(v); and for K: Km, Km1, Km2, Km3 (see, e.g., Jefferies et al. (2009) mAbs 1: 1). In certain embodiments, the antibodies variable regions described herein are linked to an Fc that binds to one or more activating Fc receptors (FcγI FcγIIa or FcγIIIa), and thereby stimulate ADCC and may cause T cell depletion. In certain embodiments, the antibody variable regions described herein are linked to an Fc that causes depletion.

In certain embodiments, the antibody variable regions described herein may be linked to an Fc comprising one or more modification, typically to alter one or more functional properties of the antibody, such as serum half-life, complement fixation, Fc receptor binding, and/or antigen-dependent cellular cytotoxicity. Furthermore, an antibody described herein may be chemically modified (e.g., one or more chemical moieties can be attached to the antibody) or be modified to alter its glycosylation, to alter one or more functional properties of the antibody. The numbering of residues in the Fc region is that of the EU index of Kabat.

The Fc region encompasses domains derived from the constant region of an immunoglobulin, preferably a human immunoglobulin, including a fragment, analog, variant, mutant or derivative of the constant region. Suitable immunoglobulins include IgG 1, IgG2, IgG3, IgG4, and other classes such as IgA, IgD, IgE and IgM, The constant region of an immunoglobulin is defined as a naturally-occurring or synthetically-produced polypeptide homologous to the immunoglobulin C-terminal region, and can include a CH I domain, a hinge, a CH2 domain, a CH3 domain, or a CH4 domain, separately or in combination. In some embodiments, an antibody of this invention has an Fc region other than that of a wild type IgA1. The antibody can have an Fc region from that of IgG (e.g., IgG1, IgG2, IgG3, and IgG4) or other classes such as IgA2, IgD, IgE and IgM. The Fc can be a mutant form of IgA1.

The constant region of an immunoglobulin is responsible for many important antibody functions including Fc receptor (FcR) binding and complement fixation. There are five major classes of heavy chain constant region, classified as IgA, IgG, IgD, IgE, IgM, each with characteristic effector functions designated by isotype. For example, IgG is separated into four subclasses known as IgG1, IgG2, IgG3, and IgG4, Ig molecules interact with multiple classes of cellular receptors. For example IgG molecules interact with three classes of Fcγ receptors (FcγR) specific for the IgG class of antibody, namely FcγRI, FcγRII, and FcγRIIL. The important sequences for the binding of IgG to the FcγR receptors have been reported to be located in the CH2 and CH3 domains. The serum half-life of an antibody is influenced by the ability of that antibody to bind to an Fc receptor (FcR).

In certain embodiments, the Fc region is a variant Fc region, e.g., an Fc sequence that has been modified (e.g., by amino acid substitution, deletion and/or insertion) relative to a parent Fc sequence (e.g., an unmodified Fc polypeptide that is subsequently modified to generate a variant), to provide desirable structural features and/or biological activity. For example, one may make modifications in the Fc region in order to generate an Fc variant that (a) has increased or decreased antibody-dependent cell-mediated cytotoxicity (ADCC), (b) increased or decreased complement mediated cytotoxicity (CDC), (c) has increased or decreased affinity for C1q and/or (d) has increased or decreased affinity for a Fc receptor relative to the parent Fc. Such Fc region variants will generally comprise at least one amino acid modification in the Fc region. Combining amino acid modifications is thought to be particularly desirable. For example, the variant Fc region may include two, three, four, five, etc. substitutions therein, e.g. of the specific Fc region positions identified herein.

A variant Fc region may also comprise a sequence alteration wherein amino acids involved in disulfide bond formation are removed or replaced with other amino acids. Such removal may avoid reaction with other cysteine-containing proteins present in the host cell used to produce the antibodies described herein. Even when cysteine residues are removed, single chain Fc domains can still form a dimeric Fc domain that is held together non-covalently. In other embodiments, the Fc region may be modified to make it more compatible with a selected host cell. For example, one may remove the PA sequence near the N-terminus of a typical native Fc region, which may be recognized by a digestive enzyme in E. coli such as proline iminopeptidase. In other embodiments, one or more glycosylation sites within the Fc domain may be removed. Residues that are typically glycosylated (e.g., asparagine) may confer cytolytic response. Such residues may be deleted or substituted with unglycosylated residues (e.g., alanine). In other embodiments, sites involved in interaction with complement, such as the C1q binding site, may be removed from the Fc region. For example, one may delete or substitute the EKK sequence of human IgG1. In certain embodiments, sites that affect binding to Fc receptors may be removed, preferably sites other than salvage receptor binding sites. In other embodiments, an Fc region may be modified to remove an ADCC site. ADCC sites are known in the art; see, for example, Molec. Immunol. 29 (5): 633-9 (1992) with regard to ADCC sites in IgG1. Specific examples of variant Fc domains are disclosed for example, in WO 97/34631 and WO 96/32478.

In one embodiment, the hinge region of Fc is modified such that the number of cysteine residues in the hinge region is altered, e.g., increased or decreased. This approach is described further in U.S. Pat. No. 5,677,425 by Bodmer et al. The number of cysteine residues in the hinge region of Fc is altered to, for example, facilitate assembly of the light and heavy chains or to increase or decrease the stability of the antibody. In one embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the CI component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et al.

In yet another example, the Fc region may be modified to increase antibody dependent cellular cytotoxicity (ADCC) and/or to increase the affinity for an Fcγ receptor by modifying one or more amino acids at the following positions: 234, 235, 236, 238, 239, 240, 241, 243, 244, 245, 247, 248, 249, 252, 254, 255, 256, 258, 262, 263, 264, 265, 267, 268, 269, 270, 272, 276, 278, 280, 283, 285, 286, 289, 290, 292, 293, 294, 295, 296, 298, 299, 301, 303, 305, 307, 309, 312, 313, 315, 320, 322, 324, 325, 326, 327, 329, 330, 331, 332, 333, 334, 335, 337, 338, 340, 360, 373, 376, 378, 382, 388, 389, 398, 414, 416, 419, 430, 433, 434, 435, 436, 437, 438 or 439. Exemplary substitutions include 236A, 239D, 239E, 268D, 267E, 268E, 268F, 324T, 332D, and 332E. Exemplary variants include 239D/332E, 236A/332E, 236A/239D/332E, 268F/324T, 267E/268F, 267E/324T, and 267E/268F7324T. Other modifications for enhancing FcγR and complement interactions include but are not limited to substitutions 298A, 333A, 334A, 326A, 247I, 339D, 339Q, 280H, 290S, 298D, 298V, 243L, 292P, 300L, 396L, 305I, and 396L. These and other modifications are reviewed in Strohl, 2009, Current Opinion in Biotechnology 20:685-691.

Fc modifications that increase binding to an Fcγ receptor include amino acid modifications at any one or more of amino acid positions 238, 239, 248, 249, 252, 254, 255, 256, 258, 265, 267, 268, 269, 270, 272, 279, 280, 283, 285, 298, 289, 290, 292, 293, 294, 295, 296, 298, 301, 303, 305, 307, 312, 315, 324, 327, 329, 330, 335, 337, 3338, 340, 360, 373, 376, 379, 382, 388, 389, 398, 414, 416, 419, 430, 434, 435, 437, 438 or 439 of the Fc region, wherein the numbering of the residues in the Fc region is that of the EU index as in abat (WO00/42072).

Other Fc modifications that can be made to Fcs are those for reducing or ablating binding to FcγR and/or complement proteins, thereby reducing or ablating Fc-mediated effector functions such as ADCC, ADCP, and CDC. Exemplary modifications include but are not limited substitutions, insertions, and deletions at positions 234, 235, 236, 237, 267, 269, 325, and 328, wherein numbering is according to the EU index. Exemplary substitutions include but are not limited to 234G, 235G, 236R, 237K, 267R, 269R, 325L, and 328R, wherein numbering is according to the EU index. An Fc variant may comprise 236R/328R. Other modifications for reducing FcγR and complement interactions include substitutions 297A, 234A, 235A, 237A, 318A, 228P, 236E, 268Q, 309L, 330S, 331S, 220S, 226S, 229S, 238S, 233P, and 234V, as well as removal of the glycosylation at position 297 by mutational or enzymatic means or by production in organisms such as bacteria that do not glycosylate proteins. These and other modifications are reviewed in Strohl, 2009, Current Opinion in Biotechnology 20:685-691.

Optionally, the Fc region may comprise a non-naturally occurring amino acid residue at additional and/or alternative positions known to one skilled in the art (see, e.g., U.S. Pat. Nos. 5,624,821; 6,277,375; 6,737,056; 6,194,551; 7,317,091; 8,101,720; WO00/42072; WO01/58957; WO02/06919; WO04/016750; WO04/029207; WO04/035752; WO04/074455; WO04/099249; WO04/063351; WO05/070963; WO05/040217, WO05/092925 and WO06/020114).

Fc variants that enhance affinity for an inhibitory receptor FcγRIIb may also be used. Such variants may provide an Fc fusion protein with immune-modulatory activities related to FcγRIIb cells, including for example B cells and monocytes. In one embodiment, the Fc variants provide selectively enhanced affinity to FcγRIIb relative to one or more activating receptors. Modifications for altering binding to FcγRIIb include one or more modifications at a position selected from the group consisting of 234, 235, 236, 237, 239, 266, 267, 268, 325, 326, 327, 328, and 332, according to the EU index. Exemplary substitutions for enhancing FcγRllb affinity include but are not limited to 234D, 234E, 234F, 234W, 235D, 235F, 235R, 235Y, 236D, 236N, 237D, 237N, 239D, 239E, 266M, 267D, 267E, 268D, 268E, 327D, 327E, 328F, 328W, 328Y, and 332E. Exemplary substitutions include 235Y, 236D, 239D, 266M, 267E, 268D, 268E, 328F, 328W, and 328Y. Other Fc variants for enhancing binding to FcγRllb include 235Y/267E, 236D/267E, 239D/268D, 239D/267E, 267E/268D, 267E/268E, and 267E/328F.

The affinities and binding properties of an Fc region for its ligand may be determined by a variety of in vitro assay methods (biochemical or immunological based assays) known in the art including but not limited to, equilibrium methods (e.g., enzyme-linked immune-absorbent assay (ELISA), or radioimmunoassay (RIA)), or kinetics (e.g., BIACORE analysis), and other methods such as indirect binding assays, competitive inhibition assays, fluorescence resonance energy transfer (FRET), gel electrophoresis and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental immunology, 4th Ed., Lippincott-Raven, Philadelphia (1999), which focuses on antibody-immunogen interactions.

In certain embodiments, the antibody is modified to increase its biological half-life. Various approaches are possible. For example, this may be done by increasing the binding affinity of the Fc region for FcRn. For example, one or more of following residues can be mutated: 252, 254, 256, 433, 435, 436, as described in U.S. Pat. No. 6,277,375. Specific exemplary substitutions include one or more of the following: T252L, T254S, and/or T256F. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. Other exemplary variants that increase binding to FcRn and/or improve pharmacokinetic properties include substitutions at positions 259, 308, 428, and 434, including for example 259I, 308F, 428L, 428M, 434S, 434H. 434F, 434Y, and 434M. Other variants that increase Fc binding to FcRn include: 250E, 250Q, 428L, 428F, 250Q/428L (Hinton et al. 2004, J. Biol. Chem. 279(8): 6213-6216, Hinton et al. 2006 Journal of Immunology 176:346-356), 256A, 272A, 286A, 305A, 307A, 307Q, 31 1A, 312A, 376A, 378Q, 380A, 382A, 434A (Shields et al, Journal of Biological Chemistry, 2001, 276 (9):6591-6604), 252F, 252T, 252Y, 252W, 254T, 256S, 256R, 256Q, 256E, 256D, 256T, 309P, 311S, 433R, 433S, 4331, 433P, 433Q, 434H, 434F, 434Y, 252Y/254T/256E, 433K/434F/436H, 308T/309P/311S (Dall Acqua et al. Journal of Immunology, 2002, 169:5171-5180, Dall'Acqua et al., 2006, Journal of Biological Chemistry 281:23514-23524). Other modifications for modulating FcRn binding are described in Yeung et al., 2010, J Immunol, 182:7663-7671. In certain embodiments, hybrid IgG isotypes with particular biological characteristics may be used. For example, an IgG1/IgG3 hybrid variant may be constructed by substituting IgG1 positions in the CH2 and/or CH3 region with the amino acids from IgG3 at positions where the two isotypes differ. Thus a hybrid variant IgG antibody may be constructed that comprises one or more substitutions, e.g., 274Q, 276K, 300F, 339T, 356E, 358M, 384S, 392N, 397M, 4221, 435R, and 436F. In other embodiments described herein, an IgG1/IgG2 hybrid variant may be constructed by substituting IgG2 positions in the CH2 and/or CH3 region with amino acids from IgG1 at positions where the two isotypes differ. Thus a hybrid variant IgG antibody may be constructed chat comprises one or more substitutions, e.g., one or more of the following amino acid substitutions: 233E, 234L, 235L, 236G (referring to an insertion of a glycine at position 236), and 321 h.

Moreover, the binding sites on human IgG1 for FcγRI, FcγRII, FcγRIII and FcRn have been mapped and variants with improved binding have been described (see Shields, R. L. et al. (2001) J. Biol. Chem. 276:6591-6604). Specific mutations at positions 256, 290, 298, 333, 334 and 339 were shown to improve binding to FcγRIII Additionally, the following combination mutants were shown to improve FcγRIII binding: T256A/S298A, S298A/E333A, S298A/K224A and S298A/E333A/K334A, which has been shown to exhibit enhanced FcγRIIIa binding and ADCC activity (Shields et al., 2001). Other IgG1 variants with strongly enhanced binding to FcγRIIIa have been identified, including variants with S239D/I332E and S239D/I332E/A330L mutations which showed the greatest increase in affinity for FcγRIIIa, a decrease in FcγRIIb binding, and strong cytotoxic activity in cynomolgus monkeys (Lazar et al., 2006). Introduction of the triple mutations into antibodies such as alemtuzumab (CD52-specific), trastuzumab (HER2/neu-specific), rituximab (CD20-specific), and cetuximab (EGFR-specific) translated into greatly enhanced ADCC activity in vitro, and the S239D/I332E variant showed an enhanced capacity to deplete B cells in monkeys (Lazar et al., 2006). In addition, IgG1 mutants containing L235V, F243L, R292P, Y300L and P396L mutations which exhibited enhanced binding to FcγRIIIa and concomitantly enhanced ADCC activity in transgenic mice expressing human FcγRIIIa in models of B cell malignancies and breast cancer have been identified (Stavenhagen et al., 2007; Nordstrom et al., 2011). Other Fc mutants that may be used include: S298A/E333A/L334A, S239D/I332E, S239D/I332E/A330L, L235V/F243L/R292P/Y300L/P396L, and M428L/N434S.

In certain embodiments, an Fc is chosen that has reduced binding to FcγRs. An exemplary Fc, e.g., IgG1 Fc, with reduced FcγR binding comprises the following three amino acid substitutions: L234A, L235E and G237A.

In certain embodiments, an Fc is chosen that has reduced complement fixation. An exemplary Fc, e.g., IgG1 Fc, with reduced complement fixation has the following two amino acid substitutions: A330S and P331S.

In certain embodiments, an Fc is chosen that has essentially no effector function, i.e., it has reduced binding to FcγRs and reduced complement fixation. An exemplary Fc, e.g., IgG1 Fc, that is effectorless comprises the following five mutations: L234A, L235E, G237A, A330S and P331S.

When using an IgG4 constant domain, it is usually preferable to include the substitution S228P, which mimics the hinge sequence in IgG1 and thereby stabilizes IgG4 molecules.

Antibody Derivatives

An antibody provided herein may be further modified to contain additional nonproteinaceous moieties that are known in the art and readily available. The moieties suitable for derivatization of the antibody include but are not limited to water soluble polymers.

Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., Proc. Natl. Acad. Sci. USA 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Another modification of the antibodies described herein is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (CI-CIO) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies described herein. See for example, EP 0 154 316 by Nishimura et al. and EP0401384 by Ishikawa et al.

The present invention also encompasses a human monoclonal antibody described herein conjugated to a therapeutic agent, a polymer, a detectable label or enzyme. In one embodiment, the therapeutic agent is a cytotoxic agent. In one embodiment, the polymer is polyethylene glycol (PEG).

Methods of Productions

Antibodies may be produced using recombinant methods and compositions, e.g., as described in U.S. Pat. No. 4,816,567. In one embodiment, isolated nucleic acid encoding an anti-hemagglutinin antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-hemagglutinin antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-hemagglutinin antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B.K.C. Lo, ed., Humana Press, Totowa, N.J., 2003), pp. 245-254, describing expression of antibody fragments in E. coli.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, Nat. Biotech. 22:1409-1414 (2004), and Li et al., Nat. Biotech. 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TM cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR⁻ CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B.K.C. Lo, ed., Humana Press, Totowa, N.J.), pp. 255-268 (2003). Compositions and Formulations The antibodies of this invention represent an excellent way for the development of antiviral therapies either alone or in antibody cocktails with additional anti-IAV antibodies for the treatment of human influenza infections in humans.

In another aspect, the present invention provides a pharmaceutical composition comprising the antibodies of the present invention described herein formulated together with a pharmaceutically acceptable carrier. The composition may optionally contain one or more additional pharmaceutically active ingredients, such as another antibody or a therapeutic agent. The pharmaceutical compositions of the invention also can be administered in a combination therapy with, for example, another immune-stimulatory agent, an antiviral agent, or a vaccine, etc. In certain embodiments, a composition comprises an anti-HA antibody of this invention at a concentration of at least 1 mg/ml, 5 mg/ml, 10 mg/ml, 50 mg/ml, 100 mg/ml, 150 mg/ml, 200 mg/ml, 1-300 mg/ml, or 100-300 mg/ml.

The pharmaceutical composition can comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., Remington: The Science and Practice of Pharmacy, 20th Ed. (Lippincott Williams & Wilkins 2003), the disclosure of which is incorporated herein by reference.

Preferably, a pharmaceutical composition is suitable for intravenous, intramuscular, subcutaneous, parenteral, spinal or epidermal administration (e.g., by injection or infusion). Depending on the route of administration, the active compound can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, an antibody of the present invention described herein can be administered via a non-parenteral route, such as a topical, epidermal or mucosal route of administration, e.g., intranasally, orally, vaginally, rectally, sublingually or topically.

The pharmaceutical composition of the invention can be in the form of pharmaceutically acceptable salts. A "pharmaceutically acceptable salt" refers to a salt that retains the desired biological activity of the parent compound and does not impart any undesired toxicological effects. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

The pharmaceutical composition of the present invention can be in the form of sterile aqueous solutions or dispersions. It can also be formulated in a microemulsion, liposome, or other ordered structure suitable to high drug concentration.

An antibody of the present invention described herein can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01% to about 99% of active ingredient, preferably from about 0.1% to about 70%, most preferably from about 1% to about 30% of active ingredient in combination with a pharmaceutically acceptable carrier.

Dosage regimens can be adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. Alternatively, antibody can be administered as a sustained release formulation, in which case less frequent administration is required. For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-HA antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks. In some methods, dosage is adjusted to achieve a plasma antibody concentration of about 1-1000 μg/ml and in some methods about 25-300 μg/ml. A "therapeutically effective dosage" of an anti-HA antibody of the invention preferably results in a decrease in severity of disease symptoms, an increase in frequency and duration of disease symptom-free periods, or a prevention of impairment or disability due to the disease affliction. For example, for the treatment of IAV infection in a subject, a "therapeutically effective dosage" preferably inhibits IAV virus replication or uptake by host cells by at least about 20%, more preferably by at least about 40%, even more preferably by at least about 60%, and still more preferably by at least about 80% relative to untreated subjects. A therapeutically effective amount of a therapeutic compound can neutralize IAV virus, or otherwise ameliorate symptoms in a subject, which is typically a human or can be another mammal. The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., Sustained and Controlled Release Drug Delivery Systems, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparati (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the human monoclonal antibodies of the invention described herein can be formulated to ensure proper distribution in vivo. For example, to ensure that the therapeutic compounds of the invention cross the blood-brain barrier, they can be formulated in liposomes, which may additionally comprise targeting moieties to enhance selective transport to specific cells or organs. See, e.g. U.S. Pat. Nos. 4,522,811; 5,374,548; 5,416,016; and 5,399,331; V.V. Ranade (1989)/. Clin. Pharmacol. 29:685; Umezawa et al, (1988) Biochem. Biophys. Res. Commun. 153:1038; Bloeman et al. (1995) FEBS Lett. 357:140; M. Owais et al. (1995) Antimicrob. Agents Chemother. 39:180; Briscoe et al. (1995) Am./. Physiol. 1233:134; Schreier et al. (1994)/. Biol. Chem. 269:9090; Keinanen and Laukkanen (1994) FEBS Lett. 346:123; and Killion and Fidler (1994) Immunomethods 4:273.

Uses and Methods

The current anti-viral treatments (e.g. oseltamivir/Tamiflu, amantadine/rimantadine) for influenza are sub-optimal with increasing incidence of resistance and a limited therapeutic window (must start <48 hours after symptom onset) (Beigel J, et al. 2008. Antiviral Res 78:91-102; Garcia-Sastre A. 2006. Emerg Infect Dis 12:44-47; and Marathe B M, et al. 2016. Sci Rep 6:26742). Monoclonal antibodies continue to be a growing class of drugs in-part due to their high degree of specificity, limited off-target effects, and superb safety profile. The antibodies, compositions and formulations described herein can be used to neutralize influenza virus and thereby treating influenza infections.

Accordingly, in one aspect, the anti-HA antibodies described herein can be used to neutralize IAV virus. The neutralizing of the IAV virus can be done via (i) inhibiting IAV virus binding to a target cell; (ii) inhibiting IAV virus uptake by a target cell; (iii) inhibiting IAV virus replication; and (iv) inhibiting IAV virus particles release from infected cells. One skilled in the art possesses the ability to perform any assay to assess neutralization of IAV virus. Notably, the neutralizing properties of antibodies may be assessed by a variety of tests, which all may assess the consequences of (i) inhibition of IAV virus binding to a target cell; (ii) inhibition of IAV virus uptake by a target cell; (iii) inhibition of IAV virus replication; and (iv) inhibition of IAV virus particles release from infected cells. In other words, implementing different tests may lead to the observation of the same consequence, i.e. the loss of infectivity of the IAV virus. Thus, in one embodiment, the present invention provides a method of neutralizing IAV virus in a subject comprising administering to the subject a therapeutically effect amount of the antibody of the present invention described herein.

Another aspect of the present invention provides a method of treating an IAV-related disease. Such method includes therapeutic (following IAV infection) and prophylactic (prior to IAV exposure, infection or pathology). For example, therapeutic and prophylactic methods of treating an individual for an IAV infection include treatment of an individual having or at risk of having an IAV infection or pathology, treating an individual with an IAV infection, and methods of protecting an individual from an IAV infection, to decrease or reduce the probability of an IAV infection in an individual, to decrease or reduce susceptibility of an individual to an IAV infection, or to inhibit or prevent an IAV infection in an individual, and to decrease, reduce, inhibit or suppress transmission of an IAV from an infected individual to an uninfected individual. Such methods include administering an antibody of the present invention or a composition comprising the antibody disclosed herein to therapeutically or prophylactically treat (vaccinate or immunize) an individual having or at risk of having an IAV infection or pathology. Accordingly, methods can treat the IAV infection or pathology, or provide the individual with protection from infection (e.g., prophylactic protection).

In one embodiment, a method of treating an IAV-related disease comprises administering to an individual in need thereof an anti-HA antibody or therapeutic composition disclosed herein in an amount sufficient to reduce one or more physiological conditions or symptom associated with an IAV infection or pathology, thereby treating the IAV-related disease.

In one embodiment, an anti-HA antibody or therapeutic composition disclosed herein is used to treat an IAV-related disease. Use of an anti-HA antibody or therapeutic composition disclosed herein treats an IAV-related disease by reducing one or more physiological conditions or symptom associated with an IAV infection or pathology. In aspects of this embodiment, administration of an anti-HA or therapeutic composition disclosed herein is in an amount sufficient to reduce one or more physiological conditions or symptom associated with an IAV infection or pathology, thereby treating the IAV-based disease. In other aspects of this embodiment, administration of an anti-HA antibody or therapeutic composition disclosed herein is in an amount sufficient to increase, induce, enhance, augment, promote or stimulate IAV clearance or removal; or decrease, reduce, inhibit, suppress, prevent, control, or limit transmission of IAV to another individual.

One or more physiological conditions or symptom associated with an IAV infection or pathology will respond to a method of treatment disclosed herein. The symptoms of IAV infection or pathology vary, depending on the phase of infection.

In another aspect of the present invention, the anti-HA antibody described herein can be used in various detection methods, for use in, e.g., monitoring the progression of an IAV infection; monitoring patient response to treatment for such an infection, etc. The present disclosure provides methods of detecting an HA polypeptide in a biological sample obtained from an individual. The methods generally involve: a) contacting the biological sample with a subject anti-HA antibody; and b) detecting binding, if any, of the antibody to an epitope present in the sample. In some instances, the antibody comprises a detectable label. The level of HA polypeptide detected in the biological sample can provide an indication of the stage, degree, or severity of an IAV infection. The level of HA polypeptide detected in the biological sample can provide an indication of the individual's response to treatment for an IAV infection.

The antibodies described herein can be used together with one or more of other anti-influenza virus antibodies to neutralize influenza virus and thereby treating influenza infections.

To that end, a few other human mAbs have the ability to neutralize diverse influenza strains. These all target the HA protein expressed on the surface of the virion and include, for instance hmAbs such as 1F1 (Tsibane T, et al. 2012. PLoS Pathog 8:e1003067) and CH65 (Whittle J R, et al. 2011. Proc Natl Acad Sci USA 108:14216-14221), which bind multiple H1 isolates; hmAbs such as F10 (Sui J, et al Hwang et al. 2009. Nat Struct Mol Biol 16:265-273) and CR6261 (Ekiert D C, et al. 2009. Science 324:246-251), which recognize all group 1 viruses; hmAbs 3114 (Fu Y, et al. 2016. Nat Commun 7:12780), F16/MEDI8852 (Corti D, et al. 2011. Science 333:850-856; and Kallewaard N L, et al. 2016. Cell 166:596-608), and VS140 (Tharakaraman K, et al. 2015. Proc Natl Acad Sci USA 112:10890-10895), which each recognize both group 1 (e.g. H1, H2, H5) and group 2 (e.g. H3, H7) viruses; or hmAb CR9114 (Dreyfus C, et al. 2012. Science 337:1343-1348), which recognizes both type A and type B viruses. Several of these hmAbs are currently in clinical trials and additionally their characterization has led to the identification of conserved epitopes in influenza HA that might be valuable as targets for the development of universal influenza vaccines and/or therapeutics. mAbs with the greatest breadth consistently target the HA stem region, while those targeting the globular head of HA frequently are confined to only subtype-specific breadth (Laursen N S, et al. 2013. Antiviral Res 98:476-483; Neu K E, et al. 2016. Curr Opin Immunol 42:48-55; and Margine I, et al. 2013. J Virol 87:10435-10446). Although the HA stalk-specific mAbs have broader reactivity, their potency is substantially limited. Thus, cocktails of broadly reactive and highly potent HA globular head-specific antibodies of this invention have greater clinical feasibility.

Definitions

The term "antibody" as referred to herein includes whole antibodies and any antigen binding fragment or single chains thereof. Whole antibodies are glycoproteins comprising at least two heavy (H) chains and two light (L) chains interconnected by disulfide bonds. Each heavy chain is comprised of a heavy chain variable region (abbreviated herein as $V_H$) and a heavy chain constant region. The heavy chain constant region is comprised of three domains, $C_H1$, $C_H2$ and $C_H3$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The heavy chain variable region CDRs and FRs are HFR1, HCDR1, HFR2, HCDR2, HFR3, HCDR3, HFR4. The light chain variable region CDRs and FRs are LFR1, LCDR1, LFR2, LCDR2, LFR3, LCDR3, LFR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

The term "antigen-binding fragment or portion" of an antibody (or simply "antibody fragment or portion"), as used herein, refers to one or more fragments of an antibody that retain the ability to specifically bind to an antigen (e.g., an HA of influenza A virus). It has been shown that the antigen-binding function of an antibody can be performed by fragments of a full-length antibody. Examples of binding fragments encompassed within the term "antigen-binding fragment or portion" of an antibody include (i) a Fab fragment, a monovalent fragment consisting of the $V_L$, $V_H$, $C_L$ and $C_H 1$ domains; (ii) a F(ab')2 fragment, a bivalent fragment comprising two Fab fragments linked by a disulfide bridge at the hinge region; (iii) a Fab' fragment, which is essentially an Fab with part of the hinge region (see, FUNDAMENTAL IMMUNOLOGY (Paul ed., 3$^{rd}$ ed. 1993)); (iv) a Fd fragment consisting of the $V_H$ and $C_H 1$ domains; (v) a Fv fragment consisting of the $V_L$ and $V_H$ domains of a single arm of an antibody, (vi) a dAb fragment (Ward et al., (1989) Nature 341:544-546), which consists of a $V_H$ domain; (vii) an isolated complementarity determining region (CDR); and (viii) a nanobody, a heavy chain variable region containing a single variable domain and two constant domains. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding fragment or portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds to an HA of influenza A virus is substantially free of antibodies that specifically bind antigens other than the HA). An isolated antibody can be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody" is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention can include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity, which have variable regions in which both the framework and CDR regions are derived from human germline immunoglobulin sequences. In one embodiment, the human monoclonal antibodies can be produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The term "isotype" refers to the antibody class (e.g., IgM or IgG1) that is encoded by the heavy chain constant region genes. The phrases "an antibody recognizing an antigen" and "an antibody specific for an antigen" are used interchangeably herein with the term "an antibody which binds specifically to an antigen."

The term "human antibody derivatives" refers to any modified form of the human antibody, e.g., a conjugate of the antibody and another agent or antibody. The term "humanized antibody" is intended to refer to antibodies in which CDR sequences derived from the germline of another mammalian species, such as a mouse, have been grafted onto human framework sequences. Additional framework region modifications can be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody. The term can also refer to an antibody in which its variable region sequence or CDR(s) is derived from one source (e.g., an IgA1 antibody) and the constant region sequence or Fc is derived from a different source (e.g., a different antibody, such as an IgG, IgA2, IgD, IgE or IgM antibody).

As used herein, the term "affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (KD). Affinity can be measured by common methods known in the art, including those described herein.

As used herein, an antibody that "specifically binds to an HA of influenza A virus" refers to an antibody that binds to an HA of influenza A virus but does not substantially bind to non-influenza A virus HA. Similarly, an antibody that "specifically binds to an HA of influenza A virus H1 subtype" refers to an antibody that binds to an HA of influenza A virus H1 subtype but does not substantially bind to other subtype of influenza A virus HA.

Preferably, the antibody binds to the HA with "high affinity", namely with a $K_D$ of $1 \times 10^{-7}$ M or less, more preferably $5 \times 10^{-8}$ M or less, more preferably $3 \times 10^{-8}$ M or less, more preferably $1 \times 10^{-8}$ M or less, more preferably $5 \times 10^{-9}$ M or less or even more preferably $1 \times 10^{-9}$ M or less. The term "does not substantially bind" to a protein or cells, as used herein, means does not bind or does not bind with a high affinity to the protein or cells, i.e. binds to the protein or cells with a $K_D$ of $1 \times 10^{-6}$ M or more, more preferably $1 \times 10^{-5}$ M or more, more preferably $1 \times 10^{-4}$ M or more, more preferably $1 \times 10^{-3}$ M or more, even more preferably $1 \times 10^{-2}$ M or more.

The term "$K_{assoc}$" or "$K_a$", as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$," as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a BIACORE® system.

The term "epitope" as used herein refers to an antigenic determinant that interacts with a specific antigen binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics. An epitope typically includes at least 3, 4, 5, 6, 7, 8, 9, 10, 11, 12, 13, 14 or 15 amino acids in a unique spatial conformation. Methods for determining what epitopes are bound by a given antibody (i.e., epitope mapping) are well known in the art and include, for example, immunoblotting and immune-precipitation assays, wherein overlapping or contiguous peptides from an HA protein are tested for reactivity with a given antibody. Methods of determining spatial conformation of epitopes include techniques in the art and those described herein, for example, x-ray crystallography and 2-dimensional nuclear magnetic resonance (see, e.g., Epitope Mapping Protocols in Methods in Molecular Biology, Vol. 66, G. E. Morris, Ed. (1996)).

The term "epitope mapping" refers to the process of identification of the molecular determinants for antibody-antigen recognition.

The term "binds to an epitope" or "recognizes an epitope" with reference to an antibody or antibody fragment refers to continuous or discontinuous segments of amino acids within an antigen. Those of skill in the art understand that the terms do not necessarily mean that the antibody or antibody fragment is in direct contact with every amino acid within an epitope sequence.

The term "binds to the same epitope" with reference to two or more antibodies means that the antibodies bind to the same, overlapping or encompassing continuous or discontinuous segments of amino acids. Those of skill in the art understand that the phrase "binds to the same epitope" does not necessarily mean that the antibodies bind to or contact exactly the same amino acids. The precise amino acids which the antibodies contact can differ. For example, a first antibody can bind to a segment of amino acids that is completely encompassed by the segment of amino acids bound by a second antibody. In another example, a first antibody binds one or more segments of amino acids that significantly overlap the one or more segments bound by the second antibody. For the purposes herein, such antibodies are considered to "bind to the same epitope."

Antibodies that "compete with another antibody for binding to a target" refer to antibodies that inhibit (partially or completely) the binding of the other antibody to the target. Whether two antibodies compete with each other for binding to a target, i.e., whether and to what extent one antibody inhibits the binding of the other antibody to a target, may be determined using known competition experiments. In certain embodiments, an antibody competes with, and inhibits binding of another antibody to a target by at least 10%, 20%, 30%, 40%, 50%, 60%, 70%, 80%, 90% or 100%. The level of inhibition or competition may be different depending on which antibody is the "blocking antibody" (i.e., the cold antibody that is incubated first with the target). Competition assays can be conducted as described, for example, in Ed Harlow and David Lane, Cold Spring Harb Protoc; 2006; doi: 10.1101/pdb.prot4277 or in Chapter 11 of "Using Antibodies" by Ed Harlow and David Lane, Cold Spring Harbor Laboratory Press, Cold Spring Harbor, N.Y., USA 1999. Competing antibodies bind to the same epitope, an overlapping epitope or to adjacent epitopes (e.g., as evidenced by steric hindrance). Other competitive binding assays include: solid phase direct or indirect radioimmunoassay (RIA), solid phase direct or indirect enzyme immunoassay (EIA), sandwich competition assay (see Stahli et al., Methods in Enzymology 9:242 (1983)); solid phase direct biotin-avidin EIA (see Kirkland et al., J. Immunol. 137:3614 (1986)); solid phase direct labeled assay, solid phase direct labeled sandwich assay (see Harlow and Lane, Antibodies: A Laboratory Manual, Cold Spring Harbor Press (1988)); solid phase direct label RIA using 1-125 label (see Morel et al., Mol. Immunol. 25(1):7 (1988)); solid phase direct biotin-avidin EIA (Cheung et al., Virology 176:546 (1990)); and direct labeled RIA. (Moldenhauer et al., Scand. J. Immunol. 32:77 (1990)).

As used herein, the term "immune response" refers to a biological response within a vertebrate against foreign agents, which response protects the organism against these agents and diseases caused by them. An immune response is mediated by the action of a cell of the immune system (for example, a T lymphocyte, B lymphocyte, natural killer (NK) cell, macrophage, eosinophil, mast cell, dendritic cell or neutrophil) and soluble macromolecules produced by any of these cells or the liver (including antibodies, cytokines, and complement) that results in selective targeting, binding to, damage to, destruction of, and/or elimination from the vertebrate's body of invading pathogens, cells or tissues infected with pathogens, cancerous or other abnormal cells, or, in cases of autoimmunity or pathological inflammation, normal human cells or tissues. An immune reaction includes, e.g., activation or inhibition of a T cell, e.g., an effector T cell or a Th cell, such as a CD4+ or CD8+ T cell, or the inhibition of a Treg cell.

The term "detectable label" as used herein refers to a molecule capable of detection, including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, avidin, streptavidin or haptens), intercalating dyes and the like. The term "fluorescer" refers to a substance or a portion thereof which is capable of exhibiting fluorescence in the detectable range.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "therapeutically effective amount" of a compound of the present invention refers to an amount of the compound of the present invention that will elicit the biological or medical response of a subject, or ameliorate symptoms, slow or delay disease progression, or prevent a disease, etc. In one embodiment, the term refers to the amount that inhibits or reduces microbial colonization or infection. In one embodiment, the term refers to the amount that inhibits or reduces infection, or prevent or destroying the formation of bacterial biofilms. When applied to an individual active ingredient, administered alone, the term refers to that ingredient alone. When applied to a combination, the term refers to combined amounts of the active ingredients that result in the therapeutic effect, whether administered in combination, serially or simultaneously.

As used herein, the term "pharmaceutically acceptable carrier or excipient" refers to a carrier medium or an excipient which does not interfere with the effectiveness of the biological activity of the active ingredient(s) of the composition and which is not excessively toxic to the host at the concentrations at which it is administered. In the context of the present invention, a pharmaceutically acceptable carrier or excipient is preferably suitable for topical formulation. The term includes, but is not limited to, a solvent, a stabilizer, a solubilizer, a tonicity enhancing agent, a structure-forming agent, a suspending agent, a dispersing agent, a chelating agent, an emulsifying agent, an anti-foaming agent, an ointment base, an emollient, a skin protecting agent, a gel-forming agent, a thickening agent, a pH adjusting agent, a preservative, a penetration enhancer, a complexing agent, a lubricant, a demulcent, a viscosity enhancer, a bioadhesive polymer, or a combination thereof. The use of such agents for the formulation of pharmaceutically active substances is well known in the art (see, for example, "Remington's Pharmaceutical Sciences", E. W. Martin, 18$^{th}$ Ed., 1990, Mack Publishing Co.: Easton, Pa., which is incorporated herein by reference in its entirety).

As used herein, the term "treating" or "treatment" of any disease or disorder refers in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "a," "an," "the" and similar terms used in the context of the present invention (especially in the context of the claims) are to be construed to cover both the singular and plural unless otherwise indicated herein or clearly contradicted by the context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

The term "about" refers to within 10%, preferably within 5%, and more preferably within 1% of a given value or range. Alternatively, the term "about" refers to within an acceptable standard error of the mean, when considered by one of ordinary skill in the art.

EXAMPLES

Example 1 Material and Methods

This example describes material and methods used in Examples 2-5 bellow

Cells and Viruses

Canine Madin-Darby canine kidney (MDCK; ATCC CCL-34) and human embryonic kidney (HEK293T; ATCC CRL-11268) cells were grown at 37° C. with 5% $CO_2$ in Dulbecco's modified Eagle's medium (DMEM; Mediatech, Inc.), 10% fetal bovine serum (FBS), and 1% PSG (penicillin, 100 units/ml; streptomycin 100 µg/ml; L-glutamine, 2 mM) (Nogales A, et al. 2014. J Virol 88:10525-10540). The following influenza A and B viruses were propagated in MDCK cells: A/California/04/2009 (pH1N1) wild-type (WT) and mCherry-expressing viruses (Nogales A, et al. 2015. Virus Res 213:69-81; and Nogales A, et al. 2014. Virology 476C:206-216); A/Puerto Rico/08/1934 H1N1 (PR8 H1N1) WT and mCherry-expressing viruses (Nogales A, et al. 2014. Virology 476C:206-216), A/Texas/36/91 H1N1 (TX H1N1), A/New Caledonia/20/99 H1N1 (NC H1N1), A/Wyoming/3/2003 H3N2 (H3N2) WT and mCherry-expressing viruses; and B/Brisbane/60/2008 (IBV) WT and mCherry-expressing viruses (Nogales A, et al. 2015. Virus Res 213:69-81). For infections, virus stocks were diluted in phosphate buffered saline (PBS), 0.3% bovine albumin (BA) and 1% PS (PBS/BA/PS). After viral infections, cells were maintained in post-infection (p.i.) medium, containing DMEM with 0.3% BA, 1% PSG, and 1 µg/ml TPCK-treated trypsin (Sigma) (Martinez-Sobrido L, et al. 2010. J Vis Exp doi:10.3791/2057). The virus titers of the stocks were determined by standard plaque assay (plaque forming units, PFU/ml) in MDCK cells as previously described (Nogales A, et al. 2014. J Virol 88:10525-10540).

Monoclonal Antibody Generation

Peripheral blood was obtained from a healthy subject prior to, seven days, and one month after receiving the 2014-2015 seasonal inactivated quadrivalent influenza vaccine (A/California/07/2009 (H1N1) pdm09-like virus, A/Texas/50/2012 (H3N2)-like virus, B/Massachusetts/2/2012-like virus, B/Brisbane/60/2008-like virus) as standard-of-care at the University of Rochester Medical Center. The subject provided signed written informed consent. All procedures and methods were approved by the Research Subjects Review Board at the University of Rochester Medical Center and all experiments were performed in accordance with relevant guidelines and regulations. PBMC and plasma was isolated using CPT tubes (Becton Dickinson, Franklin Lakes, N.J., USA). Fresh PBMC from seven days after immunization were stained for flow cytometry as previously described with anti-CD45-Qdot800 (HI30, Invitrogen, Carlsbad, Calif.), anti-CD19-APC-Cy7 (SJ25C1, BD Biosciences, San Jose, Calif.), anti-CD20-ALEXAFLUO 700 (2H7, Biolegend, San Diego, Calif.), anti-CD3-PACIFIC-ORANGE (UCHT1, Invitrogen), anti-IgD-FITC (IA6-2, BD), anti-CD27-Qdot655 (CLB-27/1, Invitrogen), anti-CD4-Qdot705 (S3.5, Invitrogen), anti-CD38-Qdot605 (HIT2, Invitrogen), anti-CD126-PE (M5, BD), and Live/Dead fixable aqua dead cell stain (Invitrogen). Plasmablasts were single cell sorted with a FACSARIA (BD Biosciences) directly into 96-well PCR plates (Bio-Rad, Hercules, Calif.) containing 4 µL/well 0.5×PBS with 10 mM DTT (Invitrogen), and 8 U RIBOLOCK (ThermoFisher) RNAse inhibitor. Plates were sealed with MICROSEAL F FILM (Bio-Rad) and immediately frozen at −80° C. until used for RT-PCR. cDNA was synthesized and semi-nested RT-PCR for IgH, Igλ, and Igκ V gene transcripts was performed as previously described (Kobie J J, et al. 2015. Monoclon Antib Immunodiagn Immunother 34:65-72). Purified PCR products were sequenced at Genewiz Sequences and analyzed by IgBlast and IMGT/V-QUEST to identify germline V(D)J gene segments with highest identity and determine sequence properties. Expression vector cloning and transfection of human HEK293T cells (ATCC, Manassas, Va.) were performed as previously described (Kobie J J, et al. 2015. Monoclon Antib Immunodiagn Immunother 34:65-72; and Tiller T, et al. 2008. J Immunol Methods 329:112-124). IgG was purified from culture supernatant using MAGNA PROTEIN G beads (Promega, Madison, Wis.). 1069 D6 is a human IgG1 mAb that was used as an isotype control.

Deep-Sequencing Immunoglobulin Repertoire Analysis

Using the sample collected 7 days after the subject received the 2014-2015 seasonal inactivated influenza vaccine, RNA was isolated from $1 \times 10^7$ peripheral blood mononuclear cells (PBMC) using the RNEASY kit (Qiagen, Hilden, Germany), treated with DNase I (TURBO DNA-free Kit, Invitrogen, Vilnius, Lithuania) and used to synthesize cDNA with the QSCRIPT cDNA synthesis kit (QuantaBio, Beverly, Mass.). The resulting cDNA was used in subsequent PCR using PLATINUM Taq High Fidelity Polymerase (Invitrogen, Carlsbad, Calif.) and a touch-down PCR protocol starting with a 95° C. for 5 min of denaturing, then 2 cycles of 96° C. for 30 sec, 62° C. for 30 sec, and 68° C. for 1 min. The annealing temperature was dropped 2° C. for every other cycle until 55° C. which was used for the final 32 cycles. A final extension was performed at 68° C. for 10 min before holding at 12° C. Degenerate primers were designed based on Sheid et al. 2011, Science 333, 1633-1637 with supplemental primers for VH2, IgM (Richardson, C. et al., 2013, J Immunol 191, 4926-4939), IgG (Tiller, T. et al., 2008, J Immunol Methods 329, 112-124) and IgA (GAGGCTCAGCGGGAAGACCTTG, SEQ ID NO: 34). Forward and reverse primers also included a 12 nt index and the Illumina specific linker: forward: CAAGCAGAA-GACGGCATACGAGATGTG-ACTGGAGTTCA-GACGTGTGCTCTTCCGATCT, SEQ ID NO: 35; and reverse: AATGATACGGCGACCACCGAGATCTA-CACTCTTTCCCTACACGACGCTCTTCCGA TCT, SEQ ID NO: 36). Primers were synthesized and PAGE purified by Integrated DNA Technologies (Coralville, Iowa). Separate PCR reactions were completed for VH1/7, VH2, VH3, VH4, VH5, and VH6 using a final concentration of 0.05 mM of each forward primer and 0.25 mM of each reverse primer. Following PCR, products were resolved on a 1% agarose gel and bands corresponding to approximately 600 nt were excised. Bands were extracted using E.Z.N.A.™ Gel Extraction Kit (Omega Bio-Tek, Norcross, Ga.) and all 6 VH reactions composited. PCR products were submitted to the University of Rochester Genomics Research Center where QUBIT FLUOROMETRIC quantitation (ThermoFisher) and BIOANALYZER (Agilent Technologies, Santa Clara, Calif.) sizing, quantitation and quality control was performed prior to normalizing to 2 nM and flowcell hybridization and cluster generation for the MISEQ system (Illumina, Inc., San Diego, Calif.). Paired end reads (300×325 bp) were made.

Sequence analysis was performed using an in-house custom analysis pipeline described previously (Tipton C M, et al. 2015. Nat Immunol 16:755-765). All sequences were aligned with IMGT.org/HighVquest (Aouinti S, et al. 2016. Front Immunol 7:339). KPF1 lineage tree was generated by identifying the lineage (identical VH, JH, HCDR3 length, and >85% HCDR3 similarity) containing the corresponding mAb sequence. Sequences with unique nucleotide VDJ re-arrangements (singletons) were removed as a conservative approach to avoid including diversity that may be a consequence of sequencing error, and resulting sequences were analyzed using Phylip's protpars tool (version 3.695, Felsenstein, J. PHYLIP (Phylogeny Inference Package) version 3.6. Distributed by the author. Department of Genome Sciences, University of Washington, Seattle (2005)), turning on setting numbers 1, 4 and 5. The output file was then parsed using in-house custom scripts; collapsing any duplicate inferred sequences into an individual node and visualized using Cytoscape.

Binding Characterization

ELISA plates (NUNC MAXISORP, Thermo Fisher Scientific, Grand Island, N.Y.) were coated with recombinant HA proteins (Protein Sciences, Meriden, Conn.) or RSV fusion (F) Protein at 0.5m/mL, hMAbs were diluted in PBS, and binding detected with horseradish peroxidase (HRP)-conjugated anti-human IgG (Jackson ImmunoResearch, West Grove, Pa.). In select ELISAs increasing concentrations of urea was add to ELISA plate and incubated for 15 min at room temperature prior to detection with anti-IgG-HRP to evaluate avidity. The MPLEX-FLU assay immunoglobulin quantification method was performed as previously described (Wang J, et al. 2015. PLoS One 10:e0129858). Assays were performed in 96 well black-walled microtiter-plates (Millipore, Billerica, Mass.). Just prior to assay, the coupled beads were vortexed for 15 seconds and diluted to 50 beads of each bead region per µl and added at 25 µl beads per well. All plasma and hmAb dilutions and washes were performed using PBS (pH 7.2) containing 0.1% BSA (MP Biomedical, LLC, France) and 0.1% Brij-35 (Thermo Scientific, Waltham, Mass.). Twenty-five µl of diluted test plasma or hmAb were added to the 25 µl of beads in each well, in duplicate, and incubated at room temperature for 2 hours on a rotary shaker (500 rpm) in the dark. Wells were then washed twice with 150 µl of wash buffer and 50 µl 1:400 diluted PE conjugated anti-human IgG (γ chain specific) specific secondary Ab (SouthernBiotech, Birmingham, Ala.) was added and the plates incubated for 2 hours at room temperature on a rotary shaker (500 rpm) in the dark. After 3 additional washes, beads in each well were suspended with 100 µl LUMINEX driving solution (Luminex, Austin, Tex.) and analyzed on a MAGPIX multiplex reader (Luminex, Austin, Tex.), and results expressed as median fluorescence intensity (MFI).

Binding Affinity Studies Using Surface Plasmon Resonance.

The binding affinity of KPF1 to recombinant (r)HA of pH1N1 A/California/04/2009 (Protein Sciences Corp., Meriden, Conn.) was determined by SPR experiments performed with a BIACORE T200 optical biosensor (BIACORE, Uppsala, Sweden) at 25° C. KPF1 (50 nM) was flowed across flow cell 2 of a Series S SENSOR CHIP PROTEIN G (GE HealthCare, Uppsala, Sweden) using 60 sec contact time, 10 µl/min flow rate, and 30 sec for stabilization, capturing approximately 1800 resonance units (RU). Flow cell 1 was left blank (Protein G only) to serve as a reference. pH1N1 rHA was used to analyze binding with a 90 s contact time, 75 µl/m flow rate, and 700 sec dissociation time. Six different concentrations of the pH1N1 rHA in the range between 0.625-10 nM in two experiments were passed over each channel in a running buffer of PBS (pH 7.4) containing 0.05% Tween 20. After every binding event, the sensor surface was regenerated by repeated washes with 10 mM glycine (pH 1.5) at a flow rate of 30 µl/min. Each binding curve was analyzed after correcting for non-specific binding by subtraction of the signals obtained from the negative-control flow channel and buffer injections (Myszka, D. G. Improving biosensor analysis. J Mol Recognit 12, 279-284, (1999)). The kinetic parameters were obtained by local Rmax fitting due to the differing capture levels using the 1:1 Langmuir interaction model within the BIACORE T200 Evaluation Software 3.0 (GE Healthcare).

Virus Neutralization and Fluorescence-Based Microneutralization Assays

Virus neutralization assays were performed with WT and mCherry-expressing viruses as previously described (Nogales A, et al. 2015. Virus Res 213:69-81; and Nogales A, et al. 2014. Virology 476C:206-216). Briefly, KPF1 hmAb or IgG1 isotype control hmAb were serially 2-fold diluted in PBS using 96-well plates (starting concentration of 200 µg). One hundred PFUs of each virus were then added to the hmAb dilutions and incubated for 1 h at room temperature. MDCK cells (96-well plate format, 5×10$^4$ cells/well, triplicates) were then infected with the hmAb-virus mixture for 1 h at room temperature. After viral adsorption, cells were maintained in p.i. medium, with 1 µg/ml TPCK-treated trypsin (Martinez-Sobrido, L. & Garcia-Sastre, A. Generation of recombinant influenza virus from plasmid DNA. Journal of visualized experiments: JoVE, (2010)) and incubated at 33° C. For the fluorescence-based microneutralization assays, at 24-48 h p.i. cells were washed with PBS prior to red fluorescence quantification using a fluorescence plate reader (DTX-880, Becton Dickenson). Fluorescence values of mCherry virus-infected cells in the absence of hmAb were used to calculate 100% viral infection. Cells in the absence of viral infection were used to calculate the fluorescence background. Triplicate wells were used to calculate the mean and SD of neutralization. WT virus neutralization was determined by crystal violet staining at 48-72 h p.i. The neutralization titer 50 ($NT_{50}$) was determined by a sigmoidal dose response curve (GRAPHPAD PRISM, v7.0).

Evaluation of KPF1 for its Prophylactic and Therapeutic Protective Activities in Mice Five to seven-week-old female C57BL/6 mice were purchased from the National Cancer Institute (NCI) and maintained in the animal care facility at University of Rochester under specific pathogen-free conditions. All animal protocols were approved by the University of Rochester Committee of Animal Resources and complied with the recommendations in the Guide for the Care and Use of Laboratory Animals of the National Research Council (National Research Council (U.S.). Committee for the Update of the Guide for the Care and Use of Laboratory Animals., Institute for Laboratory Animal Research (U.S.), National Academies Press (U.S.). 2011. Guide for the care and use of laboratory animals, 8th ed. National Academies Press, Washington, D.C). For viral infection, mice were anesthetized intraperitoneally (i.p.) with 2,2,2-tribromoethanol (Avertin; 240 mg/kg of body weight) and inoculated intranasally (i.n.) with 10× the mouse lethal dose 50 ($MLD_{50}$) of pH1N1 in a final volume of 30 µl. After viral infection, animals were monitored daily for morbidity (body weight loss) and mortality (survival). Mice showing more that 25% loss of body weight were considered to have reached the experimental endpoint and were humanely euthanized. To determine the prophylactic efficacy of KP4F1, mice in groups of 11 were weighed and administered i.p. the hmAb at doses of 0.1, 1, and 10 mg/kg, or the irrelevant isotype control 1069 D6 hmAb at 10 mg/kg, or PBS. Twenty-four hours after dosing, mice were infected intranasally (i.n.) with the indicated virus and monitored for two weeks (N=5) (H1N1). Viral replication (pH1N1, PR8 H1N1, TX H1N1, and NC H1N1) was determined by measuring viral titers in the lungs of infected mice at days 2 and 4 p.i. To that end, three mice from each group were euthanized and lungs were collected and homogenized. Mice were euthanized by administration of a lethal dose of avertin and exsanguination. Virus titers were determined by immunofocus assay (fluorescent focus-forming units, FFU/ml) (Nogales A, et al. 2014. J Virol 88:10525-10540 and Nogales A, et al. 2016. J Virol 90:6291-6302) using the anti-NP mAb HB-65 (ATTC) and a FITC-conjugated anti-mouse secondary Ab (Dako). For the study of therapeutic efficacy, mice groups (N=5) at 6, 24 or 72 h p.i., were given i.p injections of 10 mg/kg of the KPF1 or isotype control IgG (at 6 h) or PBS (at 6 h). Geometric mean titers and data representation were performed using (GRAPHPAD PRISM, v7.0).

Selection of Monoclonal Antibody-Resistant Mutants (MAIMS)

All the MARMs were selected by incubating the pH1N1 or TX H1N1 influenza viruses under increasing concentrations of KPF1 hmAb. Briefly, MDCK cells were infected at low multiplicity of infection (MOI 0.01) with the pH1N1 in 24 well-plate. After 1 h of adsorption, p.i. medium containing the KPF1 hmAb was added to the wells. The plates were incubated at 33° C. for 2 to 3 days and observed daily for cytopathic effect (CPE). Once the infected cells exhibited more than 70% of CPE, tissue culture supernatants (TCS) were collected and used to infect fresh MDCK cells (MOI 0.01) as described above. The selection protocol was repeated for five rounds with increasing concentrations (10, 25, 50, 100 and 100 µg/ml) of the KPF1 hmAb. MARMs cultures were performed in triplicate, and cultures without hmAb were maintained in parallel to control for cell-specific mutations.

Plasmids

A polymerase I-driven pPolI plasmid containing the pH1N1 HA (Baker, S. F. et al. J Virol 87, 8591-8605, (2013)) was used as template to introduce, using site-directed mutagenesis, the amino acid changes E129K, K180N, K180Q, and E129K/K180N. Then, the BbsI and PmlI restriction sites were used to subclone the HA fragment containing the amino acid substitutions into a polymerase II-driven pCAGGS protein expression plasmids (Niwa, H., et al. Gene 108, 193-199 (1991).) using standard cloning techniques. Primers for the generation of the described mutants are available upon request. All plasmid constructs were verified by DNA sequencing (ACGT Inc.).

Immunofluorescence Assay (IFA)

For the characterization of the MARMs, confluent monolayers of MDCK cells were mock-infected or infected (MOI 0.01) with WT or the MARMs viruses. At 20 h p.i., cells were fixed with 4% PFA and permeabilized with 0.5% TRITON X-100 in PBS for 15 min at room temperature. Cells were then incubated with hmAb KPF1 or with the pH1N1 HA mouse mAb 29E3 (Manicassamy B, et al. 2010. PLoS Pathog 6:e1000745) or against NP (HB-65) for 1 hour at 37° C. After washing with 1×PBS, the cells were incubated with FITC-conjugated secondary anti-mouse Ab (Dako) and 4',6-diamidino-2-phenylindole (DAPI; Research Organics) for 1 hour at 37° C. Cells were visualized and photographed using a fluorescence microscope (OLYMPUS IX81) and camera (QIMAGING, RETIGA 2000R) with a ×10 objective. For the characterization of HA mutants, HEK293T cells were transiently transfected, using lipofectamine 2000, with 0.5 µg of the indicated pCAGGS plasmids and at 24 hours post-transfection, HA expression was analyzed by IFA as indicated above, using the hmAb KPF1 or a goat pH1N1 anti-HA polyclonal antibody as internal control (BEI Resources NR-15696).

Viral RT-PCR

Total RNA from infected MDCK cells was collected at 36 h p.i. and purified using TRIZOL reagent (Invitrogen) according to the manufacturer's specifications. cDNA synthesis for HA and NA mRNAs was performed using SuperScript® II Reverse Transcriptase (Invitrogen) and an oligo dT oligonucleotide (Invitrogen). Further, cDNAs were used as templates for PCR with primers specific for the viral HA and NA open reading frames (ORF). Then, the nucleotide sequences from MARMs and no-Ab control groups were determined (ACGT, Inc). Primer sequences for amplification of the pH1N1 HA and NA ORFs are available upon request.

Virus Growth Kinetics

Multicycle virus growth kinetics were performed in confluent monolayers of MDCK cells (12-well plate format, 5×10$^5$ cells/well, triplicates) infected (MOI 0.001) with the indicated viruses. Virus titers in TCS were determined by immunofocus assay (FFU/ml) (Nogales A, et al. 2014. J Virol 88:10525-10540 and Nogales A, et al. 2016. J Virol 90:6291-6302). Mean value and standard deviation (SD) were calculated using MICROSOFT EXCEL software.

HAI Assays

Hemagglutination inhibition (HAI) assays were used to determine the HA-neutralizing capability of KPF1. The assay was performed as describe previously (Nogales A, et al. 2014. J Virol 88:10525-10540 and Nogales A, et al. 2016. J Virol 90:6291-6302). Briefly, the KPF1hmAb was serially diluted (2-fold) in 96-well V-bottom plates and mixed 1:1 with 4 hemagglutinating units (HAU) of pH1N1 for 60 min at room temperature. The HAI titers were determined by adding 0.5% turkey red blood cells (RBCs) to the virus-hmAb mixtures for 30 min on ice. The HAI titer was defined as the minimum amount of hmAb that completely inhibited hemagglutination.

Example 2 Generation of KPF1 hmAb

Figure 1B:
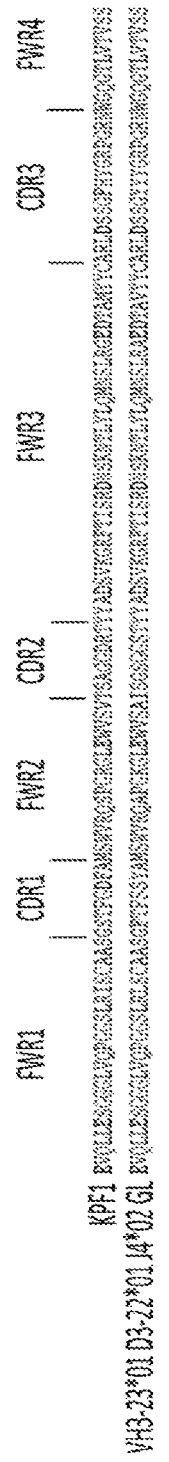

Peripheral blood plasmablasts (CD19+IgD-CD38+ CD27++) were single cell sorted from a healthy subject seven days after immunization with the 2014-2015 seasonal inactivated quadrivalent influenza vaccine. This subject had a robust plasmablast response comprising ~25% of the IgD-compartment that were predominantly CD20-CD126 (IL-6Rα)+ (FIG. 1A), consistent with an antigen-specific response (Gonzalez-Garcia I, et al. 2006. J Immunol 176: 4042-4050). The plasmablasts were subjected to single-cell RT-PCR and sequencing of the immunoglobulin variable regions and the dominant B cell lineage, comprising ~10% of the isolated plasmablasts was identified and is encoded by the immunoglobulin (Ig) heavy chain VH3-23 and kappa light chain Vk1-33 genes. Due to the dominance of this lineage among the plasmablasts, a representative member of the lineage was cloned as an IgG1 to generate the KPF1 fully hmAb. The heavy chain variable region (VH) contained 14% amino acid (8% NT) and kappa light chain variable region ($V_k$) 10% amino acids (5% NT) mutations from the germline, consistent with affinity maturation (FIG. 1B). Interestingly, this lineage included only IgA1. One constant region-encoding nucleic acid derived from the B cell lineage was aligned against a nucleic acid encoding a wild type IgA1 constant region (FIG. 1C). A representative member of the lineage was cloned as an IgG1 to generate the KPF1 fully hmAb.

The ability to isolate broadly reactive influenza mAbs indicates that the human B cell response is capable of generating such a valuable response, the challenge now lies in inducing these responses in sufficient frequency, magnitude, and durability to confer broad protection.

Example 3 In Vitro Activity of KPF1

Figures 2A, 2B:
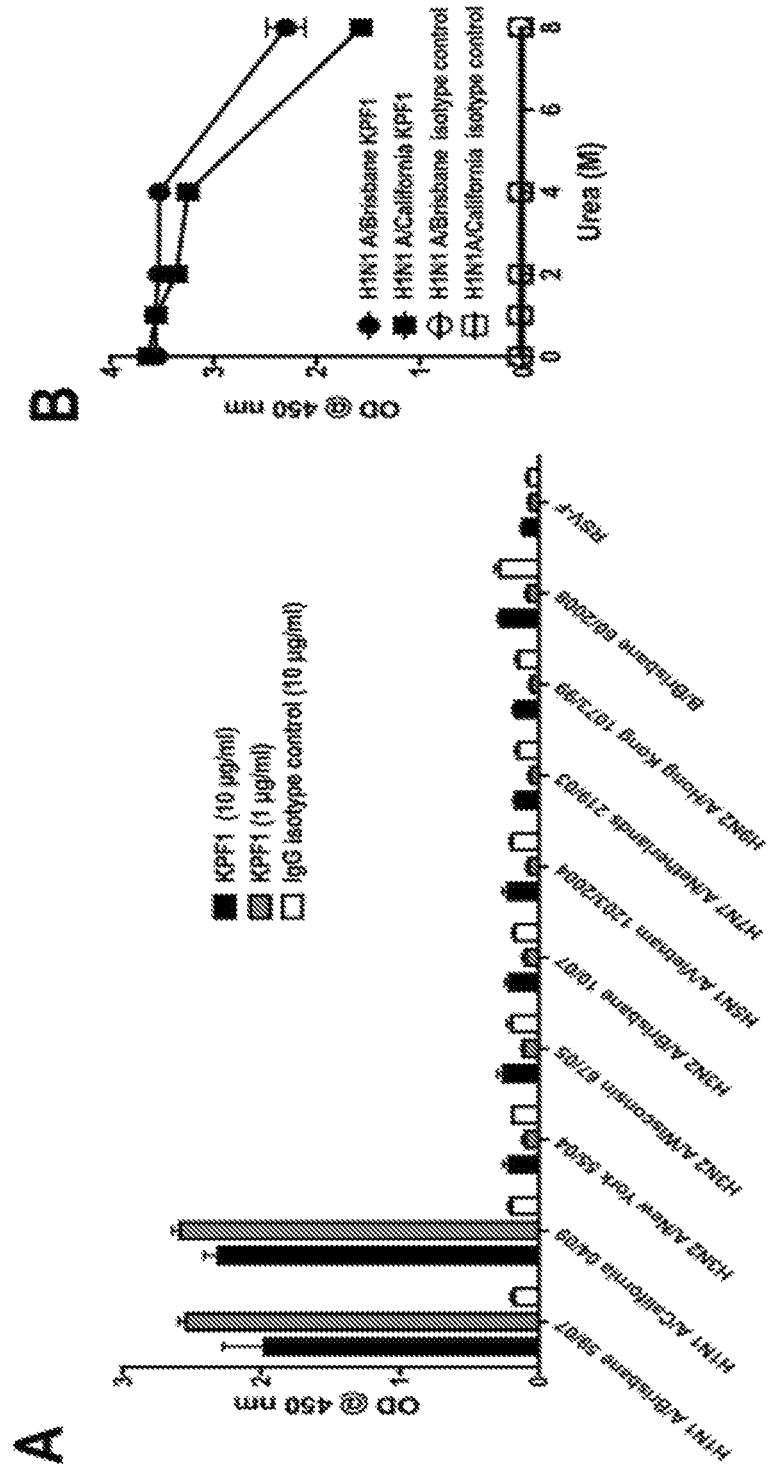
FIGS. 2A, 2B and 2C are diagrams showing that KPF1 hmAb is highly specific for H1 influenza. KPF1 hmAb and isotype control hmAb were tested by ELISA for binding to (FIG. 2A) diverse recombinant influenza H1, H3, H5, H7, H9 and IBV HAs and negative control protein (RSV-F) and (FIG. 2B) H1 HA proteins in increasing concentrations of urea. Symbols represent triplicate ±SEM.
Figure 2C:
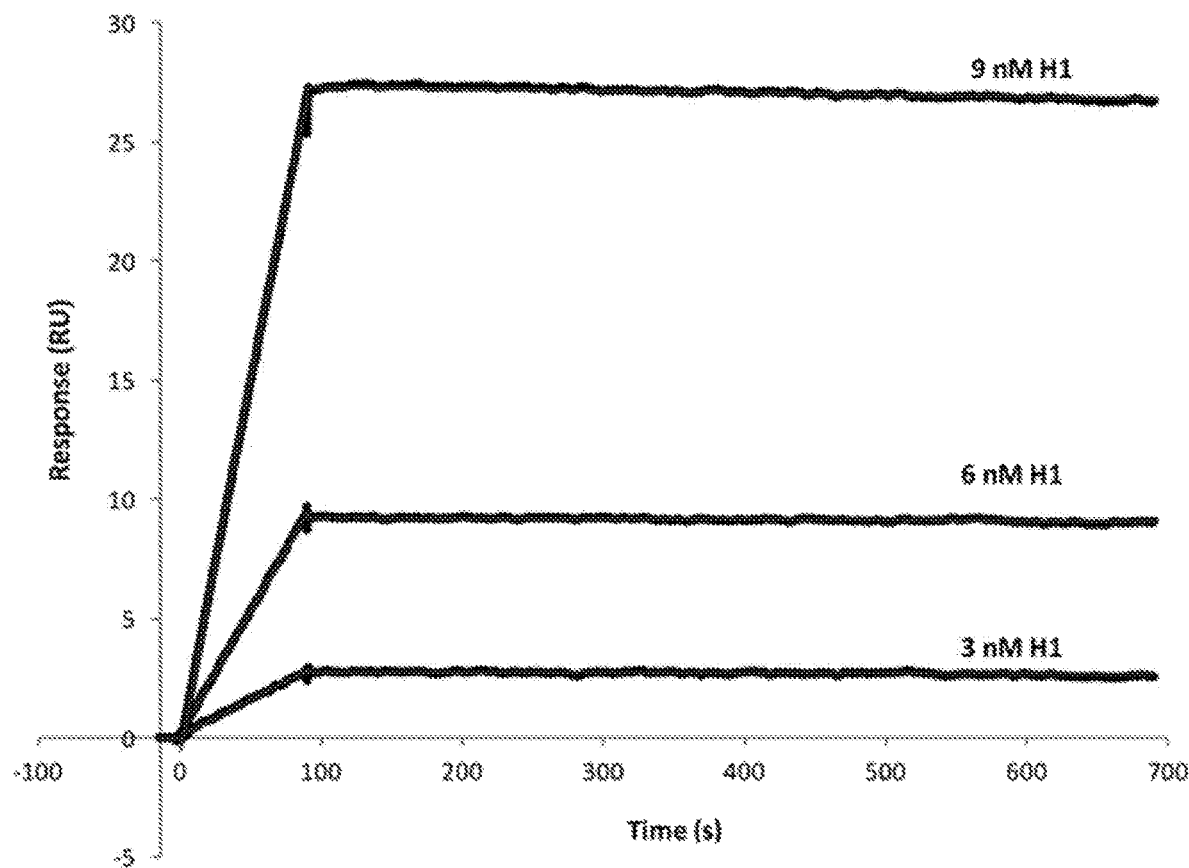
Figure 3:
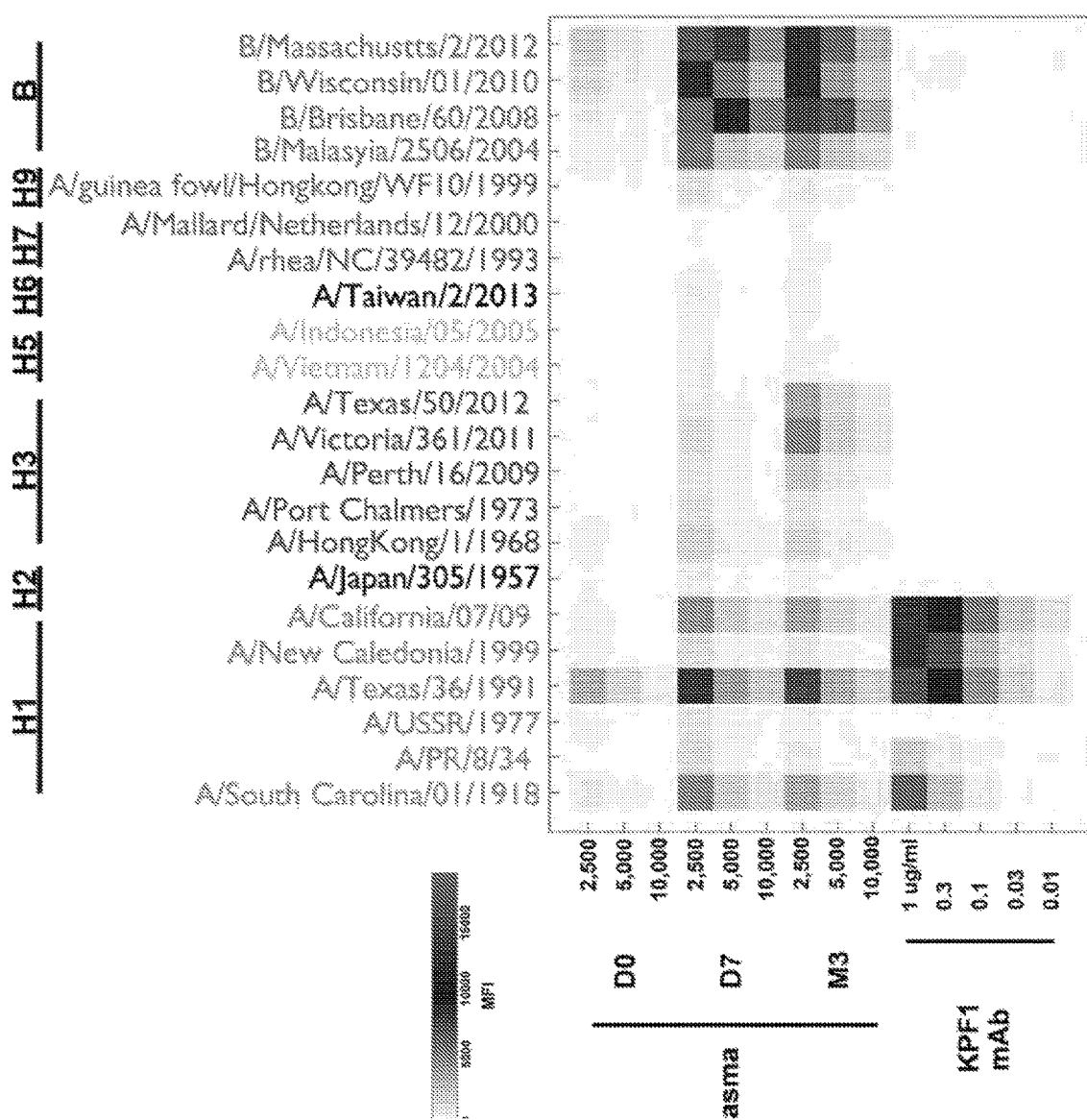
FIG. 3 is a diagram showing mPLEX-Flu binding profile. The patient's plasma from before (D0) and after 7 days (D7) and 3 months (M3) post immunization, and KPF1 hmAb were tested in decreasing concentration by multiplex assay for binding to diverse recombinant H1, H2, H3, H5, H6, H7, H9 and IBV HA proteins.

Initial characterization by ELISA revealed that KPF1 was highly specific for influenza H1 HAs, with no reactivity against influenza H3 or B HAs (FIG. 2A). Most of its binding (~50-70%) to HA was maintained even in 8M urea indicating high avidity (FIG. 2B). Surface plasmon resonance (SPR) determined KPF1 bound pH1N1 HA with very high affinity, the equilibrium dissociation constant (KD) of binding was 178 pM (FIG. 2c). The comprehensive binding profile of KPF1 against 23 HAs was determined by the fluorescent-bead based MPLEX-FLU assay that had been previously described (Wang J, et al. 2015. PLoS One 10:e0129858). KPF1 bound only to H1 HAs, including A/South Carolina/01/1918 H1N1 with a trend of greater reactivity to more recent H1N1 strains (FIG. 3). KPF1 bound 5/6 H1 HAs, failing to recognize A/USSR/1977 H1N1 at 1 µg/ml. The H1 reactivity profile for KPF1 mirrored the subject's plasma Ab response, including its strong reactivity against TX H1N1, which dominated the subject's pre-vaccination (D0) plasma response.

In addition, using a fluorescent-based (Nogales A, et al. 2016. Virus Res 213:69-81; and Nogales A, et al. 2015. Virology 476:206-216) or a traditional microneutralization assay (FIG. 4 and Table 1, respectively), KPF1 was able to neutralize broad range of H1 viruses, including potent neutralization of pH1N1 ($NT_{50}$=0.56 µg/ml FIG. 4; 1.46

μg/ml Table 1), NC H1N1 (NT50=4.56 μg/ml Table 1), and TX H1N1 (NT50=1.26 μg/ml Table 1), while neutralization of PR8 H1N1 was less efficient (NT$_{50}$=112 μg/ml FIG. 4C; 145.6 μg/ml Table 1). Neutralization of influenza A H3 or B strains was not detected even at the highest concentration of KPF1 tested (200 μg/ml) (FIGS. 4A-4C, and Table 1). KPF1 also exhibited hemagglutination inhibition (HAI) activity against pH1N1 (Table 1 and FIG. 7A). Overall KPF1 is specific to influenza A H1, and recognizes and functionally inhibits a wide range of H1 influenza virus isolates in vitro.

TABLE 1

Microneutralization and HAI assay.

| Virus[a] | NT$_{50}$ (μg/ml) [b] | HAI (μg/ml)[c] |
|---|---|---|
| pH1N1 | 1.46 | 0.78 |
| TX H1N1 | 1.26 | 0.78 |
| NC H1N1 | 4.56 | 3.12 |
| PR8 H1N1 | 145.6 | 50 |
| H3N2 | >200* | ND |
| IBV | >200* | ND |

[a]Viruses used in this assay: A/California/04/09 H1N1 (pH1N1), A/Texas/36/91 H1N1 (TX H1N1), A/New Caledonia/20/99 H1N1 (NC H1N1), A/Wyoming/3/03 H3N2 (H3N2), A/Puerto Rico/08/34 H1N1 (PR8 H1N1), or B/Brisbane/60/08 (IBV).
[b] MDCK cells were infected (100 PFU) with the indicated viruses, which were pre-incubated with 2-fold serial dilutions (starting concentration of 200 μg/ml) of the hmAb KPF1. At 48-72 h p.i., cells were stained with crystal violet and the NT50 was determined using sigmoidal dose response curves. Mock-infected cells and viruses in the absence of hmAbs were used as internal controls.
*Highest amount of hmAb without detectable neutralizing effect.
[c]HAI assays were performed using 2-fold serial dilutions (starting concentration of 200 μg/ml) of KPF1 and 4 hemagglutinating units (HAU) of the indicated viruses. HAI titers were determined by adding 0.5% turkey RBCs to the virus-hmAb mixtures and defined as the minimum amount of hmAb that completely inhibited hemagglutination.

Example 4 In Vivo Activity of KPF1

To evaluate the protective activity of KPF1, C57BL/6 mice received increasing doses of KPF1 prior to a lethal intranasal challenge dose (10×MLD$_{50}$) of pH1N1 (FIG. 5). All mice treated with PBS or IgG isotype control hmAb had severe weight loss and succumb to infection within 10 days p.i. (FIGS. 5A and 5B). However, all mice treated with 10 mg/kg or 1 mg/kg of KPF1 maintained body weight and survived infection (FIGS. 5A and 5B). Treatment with 0.1 mg/kg of KPF1 had minimal impact and non-significant differences on weight loss and survival (FIGS. 5A and 5B). Consistent with increased survival, mice treated with 1 mg/kg or 10 mg/kg had significant reductions in viral titers in their lungs at two and four days p.i., including the absence of detectable virus in 2 of 3 mice treated with 10 mg/kg, suggestive of sterilizing immunity in these mice (FIG. 5C).

Figure 5D:
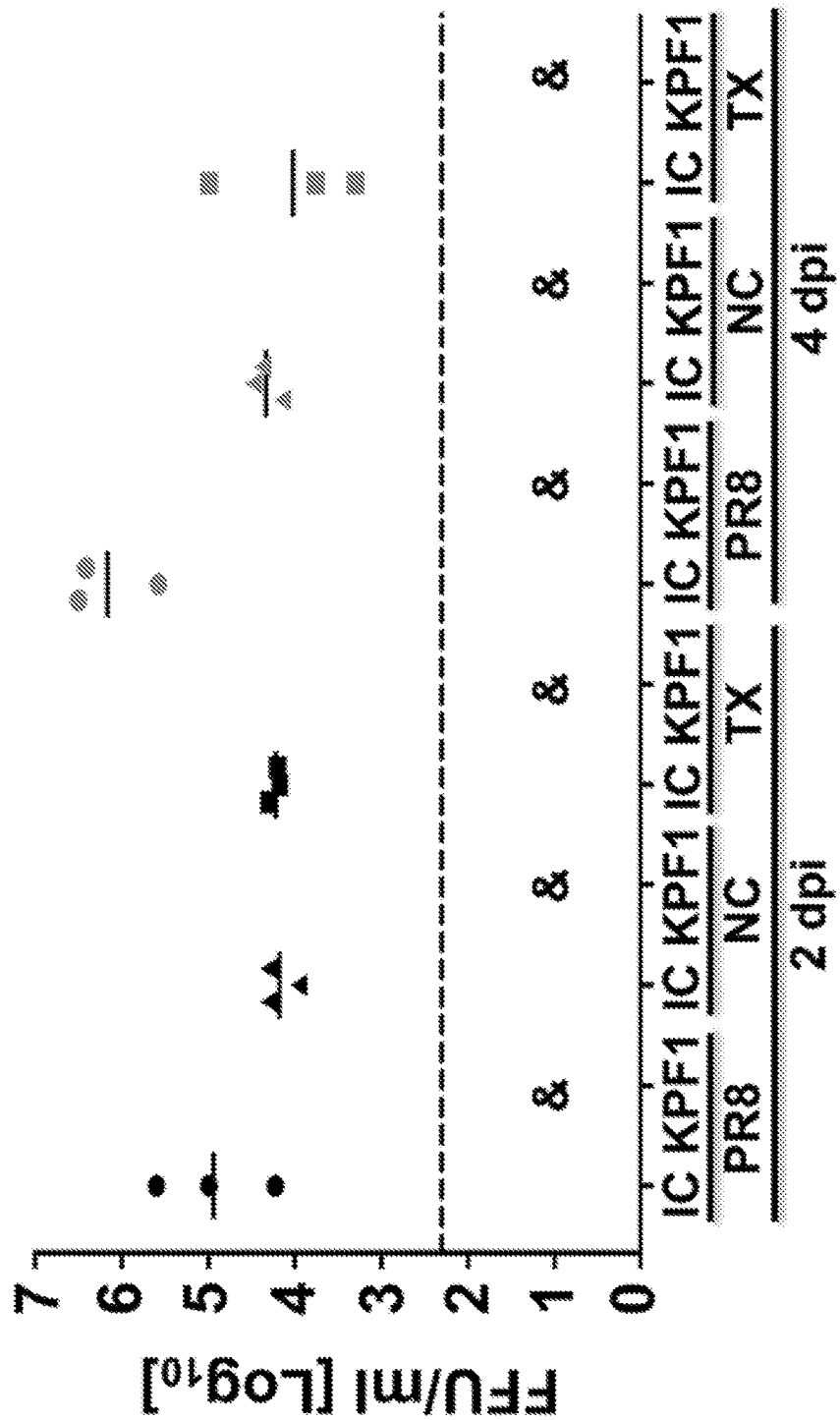

Given that KPF1 was able to neutralize other H1 influenza viruses in vitro using a microneutralization or HAI assay (FIG. 4 and Table 1), we assessed the in vivo protective activity of KPF1 against additional H1 influenza strains. For that, mice were treated with 10 mg/kg of IgG isotype control or with KPF1 and then challenged with a lethal dose (10×MLD50) of PR8, TX, or NC H1N1 influenza viruses (Pica, N. et al. J Virol 85, 12825-12829, (2011); and Nogales, A. et al. J Virol 88, 10525-10540, (2014)) and viral replication in lungs was analyzed (FIG. 5d). Correlating with the in vitro activity, mice that received the KPF1 hmAb were protected against the different viral challenges, with undetectable virus in mice treated with 10 mg/kg of KPF1 (FIG. 5d).

Figures 6A, 6B:
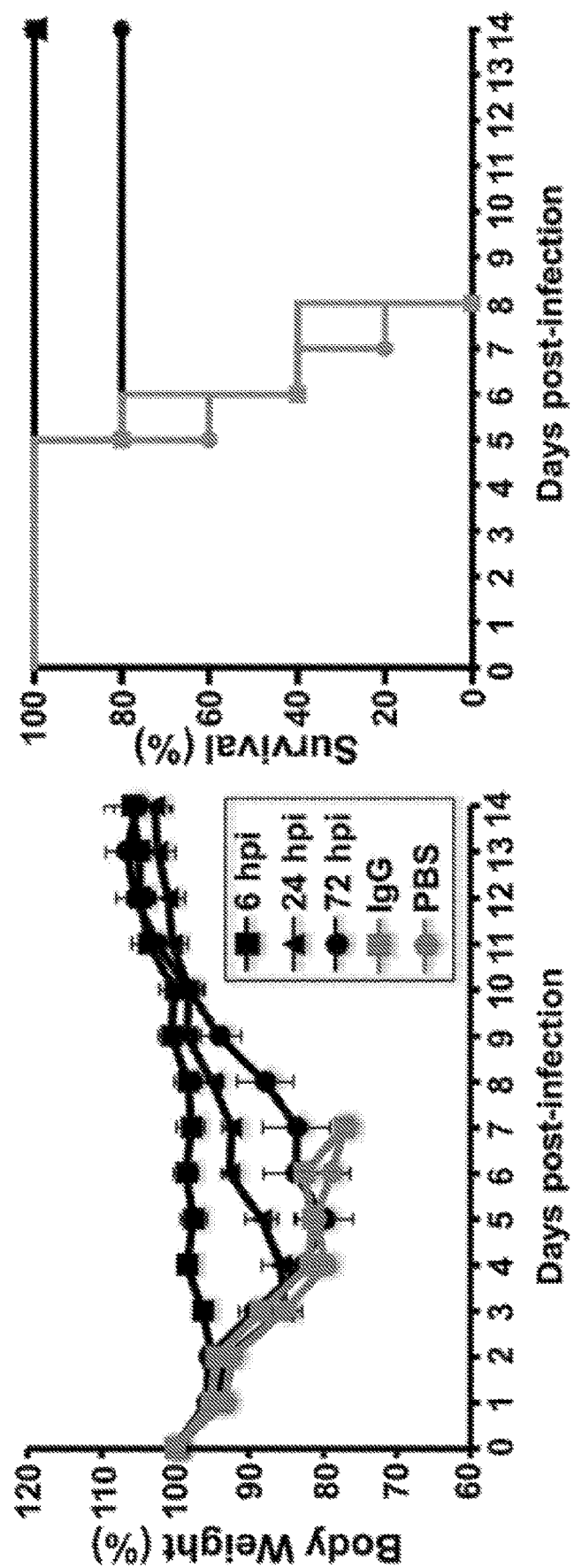
FIGS. 6A and 6B are diagrams showing therapeutic activity of KPF1 in infected mice. Female C57BL/6 mice were infected with $10 \times MLD_{50}$ of pH1N1 and then treated i.p. with 10 mg/kg of KPF1 hmAb at 6, 24 or 72 h p.i., or an Isotype control hmAb (IgG; at 6 h p.i.) or PBS (at 6 h p.i.). Then, mice were monitored daily for 2 weeks for body weight loss (FIG. 6A) and survival (FIG. 6B). Mice that lost 25% of their body weight were sacrificed. Data represent the means±SD (N=5).

Next the therapeutic activity KPF1 was assessed (FIG. 6). To that end mice were challenged with a lethal dose (10× MLD$_{50}$) of pH1N1 and then treated 6 h, 24 h, or 72 h p.i. with 10 mg/kg KPF1. All mice treated with PBS or IgG isotype control hmAb had severe weight loss and succumbed to infection within 8 days p.i. (FIGS. 6A and 6B). Early treatment (6 h p.i.) completely prevented weight loss and mortality, and delayed treatment at 24 h p.i. resulted in only transient weight loss with all mice surviving the infection. Treatment with KPF1 as late as 72 h p.i. conferred 80% survival, with the surviving mice only having transient weight loss (FIGS. 6A and 6B). Overall these results demonstrate that KPF1 has potent prophylactic and therapeutic activity against pH1N1 in vivo.

Example 5 Generation of In Vitro Escape Mutants Against KPF1

Figure 7D:
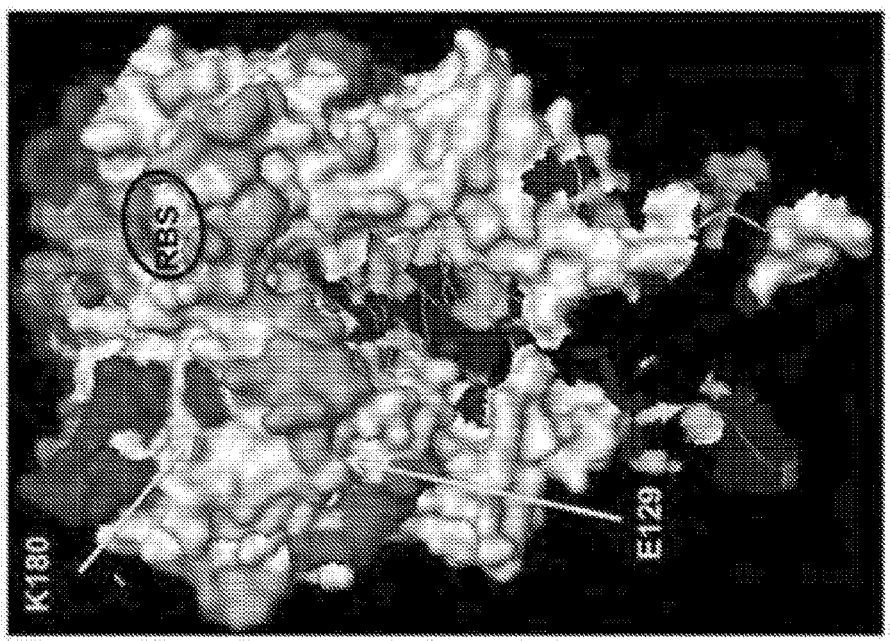
Figure 7C:
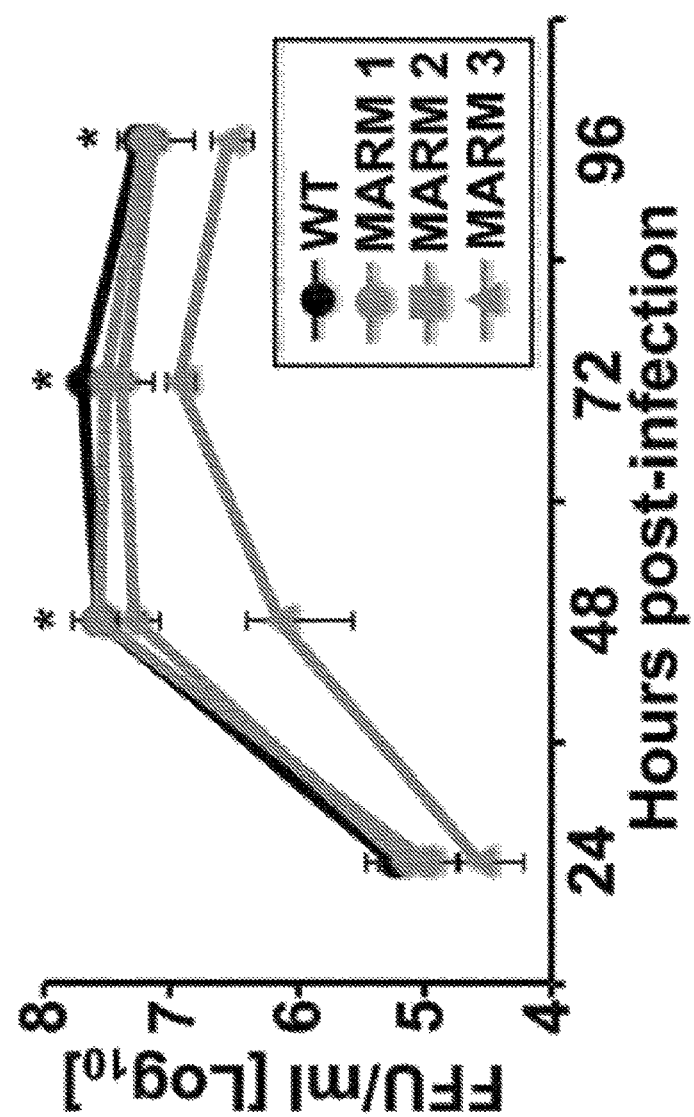

To identify amino acid residues that are critical for the formation of the KPF1 epitope, mAb-resistant mutants (MARMs) of pH1N1 were generated (FIG. 7). WT pH1N1 virus was passaged in triplicates for five rounds in the presence of increasing concentrations of KPF1 and the NA and HA ORFs were sequenced from three MARMs (MARM1, MARM2, MARM3) (FIG. 7A). No mutations were detected in NA and all three MARMs shared a point mutation (E129K) located between the Ca and Cb antigenic sites. MARM3 also had an additional mutation (K180N), which is located within the Sa antigenic site (FIGS. 7A and 7D). KPF1 did not bind to MARM1-3 as determined by immunofluorescence, although the binding to an NP-specific mAb and another pH1N1 head-specific HA mAb 29E3 was maintained (FIG. 7B). In vitro viral growth kinetics of MARM1 and MARM2 were comparable to that of pH1N1 WT, although the growth of MARM3 was significantly less (p<0.05) than pH1N1 WT, suggesting that K180N mutation impacts viral fitness (FIG. 7C). Although the amino acids in the position 129 and 180 are far away from each other in the linear sequence of the HA protein, the analysis of the tridimensional protein structure shows that both amino acids are close in the folded HA protein (FIG. 7D).

Interestingly, when TX H1N1 was propagated in the presence of KPF1, the same point mutation (E129K) identified for MARMs of pH1N1, was observed in all the MARMs of TX H1N1 (FIG. 7E). In addition, no mutations were identified in NA. These results confirm that E129 is important for the binding of KPF1 to HA. HAI assay was performed using pH1N1 or TX H1N1 viruses obtained from each round of virus selection. The HAI results indicate that MARMs are the majority viral population in passage 1 for pH1N1 or between passages 1 and 2 for TX H1N1 (data not shown). These results confirm that E129 is important for the binding of KPF1 to HA and suggest that KPF1 recognizes an epitope in the H1 HA globular head that dependent on residues near the Ca and Cb antigenic sites (E129) (FIG. 7d). Moreover, pCAGGS protein expression plasmids encoding the WT, single E129K, K180N, K180Q; or double E129K/ K180N HA mutants were generated. Next, the ability of KPF1 to recognize the different HAs was evaluated by immunofluorescence assay in transfected 293 T cells (FIG. 8a). As was expected, KPF1 was unable to recognize HA proteins containing the amino acid change E129K (E129K and E129K/K180N) but was able to recognize HA proteins containing the amino acid change at position 180 (K180N and K180Q). This suggests that position 180 is not part of the KPF1 hmAb footprint and the amino acid change observed in 1 of 3 MARMS at position 180 was probably a random event or a compensatory mutation. In addition, an in silico analysis was performed to evaluate the frequency of amino acid residues E129 and K180 in more than 17,000 strains deposited in the database of IAV H1N1 from 2000 to 2018 (FIG. 8B). Our findings indicate that amino acid E129 is highly conserved, since more than 99.5% of the analyzed IAV H1N1 sequences contain amino acid E at that position. Interestingly, the frequencies of other amino acids (including K, observed in our MARMs) represent less than 0.5% (FIG. 8B). This data suggests that this position is important for IAV H1N1 and therefore could be a suitable target for the development of antiviral therapies such as our described KPF1 hmAb. On the other hand, position 180 has higher variability, showing a shift from K to Q in the last decade (FIG. 8B). However, this variability does not affect the binding of KPF1 to HA.

Additionally, to aid in the resolution of the specific epitope of the HA protein that is recognized by the KPF-1 hmAb, PepScan-ELISA was conducted using overlapping linear peptides (listed below) covering the complete HA protein. It was found that KPF1 had the greatest reactivity to peptides covering positions 138-337. This region includes K180 which was identified in the MARM analysis, and this region is adjacent to E129 which was also identified in the MARM analysis. Overall these results suggest that KPF1 recognizes an epitope in the HA1 globular head that is dependent on residues within the Sa antigenic site and near the RDS.

| Name (aa positions) | Sequence | SEQ ID NO: |
|---|---|---|
| Peptide 1 (aa 18-97) | DTISIGYHANNSTDTVDTVLEKNVTVTHS VNLLEDSHNGKLSLLKGIAPLQLGNCSVA GWILGNPECELLISKESWSYIV | 24 |
| Peptide 2 (aa 78-157) | ILGNPESELLISKESWSYIVETPNPENGT CYPGYFADYEELREQLSSVSSFERFEIFP KESSWPNHTVTGVSASCSHNGK | 25 |
| Peptide 3 (aa 138-217) | SSWPNHTVTGVSASCSHNGKSSFYRNLLW LTGKNGLYPNLSKSYVNNKEKEVLVLWGV HHPPNIGNQRALYHTENAYVSV | 26 |
| Peptide 4 (198-277) | PPNIGNQRALYHTENAYVSVVSSHYSRRF TPEIAKRPKVRDQEGRINYYWTLLEPGDT IIFEANGNLIAPWYAFALSRGF | 27 |
| Peptide 5 (258-337) | FEANGNLIAPWYAFALSRGFGSGIITSNA PMDESDAKCQTPQGAINSSLPFQNVHPVT IGECPKYVRSAKLRMVTGLRNI | 28 |
| Peptide 6 (317-396) | GECPKYVRSAKLRMVTGLRNIPSIQSRGL FGAIAGFIEGGWTGMVDGWYGYHHQNEQG SGYAADQKSTQNAINGITNKVN | 29 |
| Peptide 7 (377-455) | YAADQKSTQNAINGITNKVNSVIEKMNTQ FTAVGKEENKLERRMENLNKKVDDGFLDI WTYNAELLVLLENERTLDFHD | 30 |
| Peptide 8 (436-515) | TYNAELLVLLENERTLDFHDSNVKNLYEK VKSQLKNNAKEIGNGSFEFYHKCNNECME SVKNGTYDYPKYSEESKLNREK | 31 |
| Peptide 9B (aa 496-535) | KNGTYDYPKYSEESKLNREKIDGVKLESM GVYQILAIYST | 32 |
| Peptide 9A (aa 520-565) | KLESMGVYQILAIYSTVASSLVLLVSLGA ISFWMSSNGSLQSRISI | 33 |

As mentioned above, although currently licensed influenza vaccines and antivirals significantly mitigate the morbidity and mortality of influenza infections, they are sub-optimal and consequently substantial public health vulnerabilities exist in our ability to prevent and treat influenza. Improving the breadth of activity of both vaccines and antivirals to confer protection from emerging seasonal isolates and those with pandemic potential is a fundamental area of emphasis. The KPF1 antibody has broad activity against H1 influenza isolates and potent prophylactic and therapeutic activity in vivo, which is mediated by recognition of conserved residues in the H1 hemagglutinin globular head. This antibody, as well as others disclosed herein, have greater clinical feasibility.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference in their entireties.

What is claimed is:

1. An isolated antibody or antigen-binding fragment thereof, that specifically binds to a hemagglutinin (HA) of influenza A virus (IAV) H1 subtype, comprising:

(i) a heavy chain variable region that comprises HCDR1, HCDR2, and HCDR3 comprising the amino acid sequences of SEQ ID NOs: 3-5, respectively, and (ii) a light chain variable region that comprises LCDR1, LCDR2 and LCDR3 comprising the amino acid sequences of SEQ ID NOs: 6-8, respectively.

2. The isolated antibody or the antigen-binding fragment thereof of claim 1, wherein the heavy chain variable region comprises the amino acid sequence of SEQ ID NO: 1 and the light chain variable region comprises the amino acid sequence of SEQ ID NO: 2.

3. The isolated antibody or the antigen-binding fragment thereof of claim 1, further comprising a variant Fc constant region.

4. The isolated antibody or the antigen-binding fragment thereof of claim 1, wherein the antibody is a chimeric antibody, a humanized antibody, or a human antibody.

5. The isolated antibody or the antigen-binding fragment thereof of claim 1, wherein the antibody or fragment is conjugated to a therapeutic agent, a polymer, a detectable label, or an enzyme.

6. The isolated antibody or the antigen-binding fragment thereof of claim 2, wherein the polymer is polyethylene glycol (PEG).

7. The isolated antibody or the antigen-binding fragment thereof of claim 2, wherein the therapeutic agent is cytotoxic agent.

8. A pharmaceutical composition comprising the antibody or the antigen-binding fragment thereof of claim 1 and a pharmaceutically acceptable carrier.

* * * * *

SEQUENCE LISTING

<160> NUMBER OF SEQ ID NOS: 36

<210> SEQ ID NO 1
<211> LENGTH: 123
<212> TYPE: PRT
<213> ORGANISM: Homo sapiens

<400> SEQUENCE: 1

Glu Val Gln Leu Leu Glu Ser Gly Gly Gly Leu Val Gln Pro Gly Gly
1               5                   10                  15

Ser Leu Arg Ile Ser Cys Ala Ala Ser Gly Ser Thr Phe Gly Asp Phe
            20                  25                  30

Ala Met Ser Trp Val Arg Gln Ser Pro Gly Arg Gly Leu Glu Trp Val
        35                  40                  45

Ser Val Thr Ser Ala Gly Gly Asp Arg Thr Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Gly Glu Asp Thr Ala Met Tyr Tyr Cys
                 85                  90                  95

Ala Arg Leu Asp Ser Ser Gly Phe His Tyr Gly Arg Pro Gly Arg Asn
            100                 105                 110

Trp Gly Gln Gly Thr Leu Val Thr Val Ser Ser
        115                 120
```

<210> SEQ ID NO 2
<211> LENGTH: 107
<212> TYPE: PRT
<213> ORGANISM: Homo sapiens

<400> SEQUENCE: 2

```
Asp Ile Gln Met Thr His Ser Pro Pro Ser Leu Ser Ala Ser Val Gly
  1               5                  10                  15

Asp Arg Ile Thr Ile Thr Cys Gln Ala Ser Gln Asp Ile Ser Tyr Tyr
             20                  25                  30

Leu Ile Trp Tyr Gln Gln Lys Pro Gly Lys Ala Pro Lys Pro Leu Ile
         35                  40                  45

Tyr Asp Ala Ser Asn Leu Glu Ala Gly Val Pro Ser Arg Phe Ser Ala
 50                  55                  60

Ser Gly Ser Gly Thr Asp Phe Thr Leu Thr Ile Ser Ser Leu Gln Pro
 65                  70                  75                  80

Glu Asp Leu Ala Thr Tyr Tyr Cys Gln Gln Tyr Lys Ser Leu Pro Tyr
                 85                  90                  95

Thr Phe Gly Gln Gly Thr Lys Leu Glu Ile Lys
            100                 105
```

<210> SEQ ID NO 3
<211> LENGTH: 8
<212> TYPE: PRT
<213> ORGANISM: Homo sapiens

<400> SEQUENCE: 3

```
Gly Ser Thr Phe Gly Asp Phe Ala
  1               5
```

<210> SEQ ID NO 4
<211> LENGTH: 8
<212> TYPE: PRT
<213> ORGANISM: Homo sapiens

<400> SEQUENCE: 4

```
Thr Ser Ala Gly Gly Asp Arg Thr
  1               5
```

<210> SEQ ID NO 5
<211> LENGTH: 16
<212> TYPE: PRT
<213> ORGANISM: Homo sapiens

<400> SEQUENCE: 5

```
Ala Arg Leu Asp Ser Ser Gly Phe His Tyr Gly Arg Pro Gly Arg Asn
  1               5                  10                  15
```

<210> SEQ ID NO 6
<211> LENGTH: 6
<212> TYPE: PRT

```
<213> ORGANISM: Homo sapiens

<400> SEQUENCE: 6

Gln Asp Ile Ser Tyr Tyr
1               5

<210> SEQ ID NO 7
<211> LENGTH: 3
<212> TYPE: PRT
<213> ORGANISM: Homo sapiens

<400> SEQUENCE: 7

Asp Ala Ser
1

<210> SEQ ID NO 8
<211> LENGTH: 9
<212> TYPE: PRT
<213> ORGANISM: Homo sapiens

<400> SEQUENCE: 8

Gln Gln Tyr Lys Ser Leu Pro Tyr Thr
1               5

<210> SEQ ID NO 9
<211> LENGTH: 97
<212> TYPE: PRT
<213> ORGANISM: Homo sapiens

<400> SEQUENCE: 9

Asp Ile Gln Met Thr His Ser Pro Pro Ser Leu Ser Ala Ser Val Gly
1               5                   10                  15

Asp Arg Ile Thr Ile Thr Cys Gln Ala Ser Gln Asp Ile Ser Tyr Tyr
            20                  25                  30

Leu Ile Trp Tyr Gln Gln Lys Pro Gly Lys Ala Pro Lys Pro Leu Ile
        35                  40                  45

Tyr Asp Ala Ser Asn Leu Glu Ala Gly Val Pro Ser Arg Phe Ser Ala
    50                  55                  60

Ser Gly Ser Gly Thr Asp Phe Thr Leu Thr Ile Ser Leu Gln Pro
65                  70                  75                  80

Glu Asp Leu Ala Thr Tyr Tyr Cys Gln Gln Tyr Lys Ser Leu Pro Tyr
                85                  90                  95

Thr

<210> SEQ ID NO 10
<211> LENGTH: 123
<212> TYPE: PRT
<213> ORGANISM: Homo sapiens

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
            85                  90                  95

Ala Arg Leu Asp Ser Ser Gly Tyr Tyr Tyr Gly Arg Pro Gly Arg Asn
            100                 105                 110

Trp Gly Gln Gly Thr Leu Val Thr Val Ser Ser
        115                 120

<210> SEQ ID NO 11
<211> LENGTH: 97
<212> TYPE: PRT
<213> ORGANISM: Homo sapiens

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Tyr
                85                  90                  95

Thr

<210> SEQ ID NO 12
<211> LENGTH: 1701
<212> TYPE: DNA
<213> ORGANISM: Influenza A virus

<400> SEQUENCE: 12
atgaaggcaa tactagtagt tctgctatat acatttgcaa ccgcaaatgc agacacatta 60
tgtataggtt atcatgcgaa caattcaaca gacactgtag acacagtact agaaaagaat 120
gtaacagtaa cacactctgt taaccttcta gaagacaagc ataacgggaa actatgcaaa 180
ctaagagggg tagccccatt gcatttgggt aaatgtaaca ttgctggctg gatcctggga 240
aatccagagt gtgaatcact ctccacagca agctcatggt cctacattgt ggaaacacct 300
agttcagaca atggaacgtg ttacccagga gatttcatcg attatgagga gctaagagag 360
caattgagct cagtgtcatc atttgaaagg tttgagatat tccccaagac aagttcatgg 420
cccaatcatg actcgaacaa aggtgtaacg gcagcatgtc ctcatgctgg agcaaaaagc 480
ttctacaaaa atttaatatg gctagttaaa aaaggaaatt catacccaaa gctcagcaaa 540
tcctacatta atgataaagg gaaagaagtc ctcgtgctat ggggcattca ccatccatct 600
actagtgctg accaacaaag tctctatcag aatgcagatg catatgtttt tgtggggtca 660
tcaagataca gcaagaagtt caagccggaa atagcaataa gacccaaagt gagggatcaa 720
gaagggagaa tgaactatta ctggacacta gtagagccgg gagacaaaat aacattcgaa 780
gcaactggaa atctagtggt accgagatat gcattcgcaa tggaaagaaa tgctggatct 840
ggtattatca tttcagatac accagtccac gattgcaata caacttgtca aacacccaag 900
ggtgctataa acaccagcct cccatttcag aatatacatc cgatcacaat tggaaaatgt 960
ccaaaatatg taaaaagcac aaaattgaga ctggccacag gattgaggaa tatcccgtct 1020

```
attcaatcta gaggcctatt tggggccatt gccggtttca ttgaaggggg gtggacaggg    1080
atggtagatg gatggtacgg ttatcaccat caaaatgagc aggggtcagg atatgcagcc    1140
gacctgaaga gcacacagaa tgccattgac gagattacta acaaagtaaa ttctgttatt    1200
gaaaagatga atacacagtt cacagcagta ggtaaagagt caaccacct ggaaaaaga     1260 atagagaatt taaataaaaa agttgatgat ggtttcctgg acatttggac ttacaatgcc    1320
gaactgttgg ttctattgga aaatgaaaga actttggact accacgattc aaatgtgaag    1380
aacttatatg aaaaggtaag aagccagcta aaaaacaatg ccaaggaaat tggaaacggc    1440
tgctttgaat tttaccacaa atgcgataac acgtgcatgg aaagtgtcaa aaatgggact    1500
tatgactacc caaaatactc agaggaagca aaattaaaca gagaagaaat agatggggta    1560
aagctggaat caacaaggat ttaccagatt ttggcgatct attcaactgt cgccagttca    1620
ttggtactgg tagtctccct ggggggcaatc agtttctgga tgtgctctaa tgggtctcta    1680
cagtgtagaa tatgtattta a                                             1701
```

<210> SEQ ID NO 13
<211> LENGTH: 566
<212> TYPE: PRT
<213> ORGANISM: Influenza A virus

<400> SEQUENCE: 13

```
Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Ala Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
```

-continued

```
                245                 250                 255
Ile Thr Phe Glu Ala Thr Gly Asn Leu Val Pro Arg Tyr Ala Phe
            260                 265                 270
Ala Met Glu Arg Asn Ala Gly Ser Gly Ile Ile Ile Ser Asp Thr Pro
            275                 280                 285
Val His Asp Cys Asn Thr Thr Cys Gln Thr Pro Lys Gly Ala Ile Asn
            290                 295                 300
Thr Ser Leu Pro Phe Gln Asn Ile His Pro Ile Thr Ile Gly Lys Cys
305                 310                 315                 320
Pro Lys Tyr Val Lys Ser Thr Lys Leu Arg Leu Ala Thr Gly Leu Arg
                325                 330                 335
Asn Ile Pro Ser Ile Gln Ser Arg Gly Leu Phe Gly Ala Ile Ala Gly
            340                 345                 350
Phe Ile Glu Gly Gly Trp Thr Gly Met Val Asp Gly Trp Tyr Gly Tyr
            355                 360                 365
His His Gln Asn Glu Gln Gly Ser Gly Tyr Ala Ala Asp Leu Lys Ser
            370                 375                 380
Thr Gln Asn Ala Ile Asp Glu Ile Thr Asn Lys Val Asn Ser Val Ile
385                 390                 395                 400
Glu Lys Met Asn Thr Gln Phe Thr Ala Val Gly Lys Glu Phe Asn His
                405                 410                 415
Leu Glu Lys Arg Ile Glu Asn Leu Asn Lys Lys Val Asp Asp Gly Phe
            420                 425                 430
Leu Asp Ile Trp Thr Tyr Asn Ala Glu Leu Leu Val Leu Leu Glu Asn
            435                 440                 445
Glu Arg Thr Leu Asp Tyr His Asp Ser Asn Val Lys Asn Leu Tyr Glu
            450                 455                 460
Lys Val Arg Ser Gln Leu Lys Asn Asn Ala Lys Glu Ile Gly Asn Gly
465                 470                 475                 480
Cys Phe Glu Phe Tyr His Lys Cys Asp Asn Thr Cys Met Glu Ser Val
                485                 490                 495
Lys Asn Gly Thr Tyr Asp Tyr Pro Lys Tyr Ser Glu Glu Ala Lys Leu
            500                 505                 510
Asn Arg Glu Glu Ile Asp Gly Val Lys Leu Glu Ser Thr Arg Ile Tyr
            515                 520                 525
Gln Ile Leu Ala Ile Tyr Ser Thr Val Ala Ser Ser Leu Val Leu Val
            530                 535                 540
Val Ser Leu Gly Ala Ile Ser Phe Trp Met Cys Ser Asn Gly Ser Leu
545                 550                 555                 560
Gln Cys Arg Ile Cys Ile
                565
```

<210> SEQ ID NO 14
<211> LENGTH: 1701
<212> TYPE: DNA
<213> ORGANISM: Influenza A virus

<400> SEQUENCE: 14

```
atgaagacta tcattgcttt gagctacatt ctatgtctgg ttttcgctca aaaacttcct      60
ggaaatgaca atagcacggc aacgctgtgc cttgggcacc atgcagtacc aaacggaacg     120
atagtgaaaa caatcacgaa tgaccgaatt gaagttacta atgctactga actggttcag     180
aattcctcaa taggtgaaat atgcgacagt cctcatcaga tccttgatgg agaaaactgc     240
acactaatag atgctctatt gggagaccct cagtgtgatg gcttccaaaa taagaaatgg     300
```

```
gaccttttttg ttgaacgaag caaagcctac agcaactgtt acccttatga tgtgccggat    360
tatgcctccc ttaggtcact agttgcctca tccggcacac tggagtttaa caatgaaagc    420
ttcaattgga atggagtcac tcaaaacgga acaagttctg cttgcataag gagatctaat    480 aatagttttct ttagtagatt aaattggttg acccacttaa acttcaaata cccagcattg    540
aacgtgacta tgccaaacaa tgaacaattt gacaaattgt acatttgggg ggttcaccac    600
ccggttacgg acaaggacca aatcttcctg tatgctcaac catcaggaag aatcacagta    660
tctaccaaaa gaagccaaca agctgtaatc ccgaatatcg gatttagacc cagaataagg    720
aataacccta gcagaataag catctattgg acaatagtaa aaccgggaga catacttttg    780
attaacagca cagggaatct aattgctcct agggggttact tcaaaatacg aagtgggaaa    840
agctcaataa tgagatcaga tgcacccatt ggcaaatgca agtctgaatg catcactcca    900
aatggaagca ttcccaatga caaaccattc caaaatgtaa acaggatcac atacggggcc    960
tgtcccagat atgttaagca agcactctg aaattggcaa caggaatgcg gaatgtacca   1020
gagaaacaaa ctagaggcat atttggcgca atagcgggtt tcatagaaaa tggttgggag   1080
ggaatggtgg atggttggta cggtttcagg catcaaaatt ctgagggaag aggacaagca   1140
gcagatctca aaagcactca agcagcaatc gatcaaatca tgggaagct gaatcgattg   1200 atcgggaaaa ccaacgagaa attccatcag attgaaaaag aattctcaga gtagaaggg   1260 agaattcagg accttgagaa atatgttgag gacactaaaa tagatctctg gtcatacaac   1320
gcggagcttc ttgttgccct ggagaaccaa catacaattg atctaactga ctcagaaatg   1380
aacaaactgt ttgaaaaaac aaagaagcaa ctgagggaaa atgctgagga tatgggcaat   1440
ggttgtttca aaatatacca caatgtgac aatgcctgca taggatcaat cagaaatgga   1500
acttatgacc acgatgtata cagagatgaa gcattaaaca accggttcca gatcaaggga   1560
gttgagctga gtcagggta caaagattgg atcctatgga tttccttttgc catatcatgt   1620 tttttgcttt gtgttgcttt gttggggttc atcatgtggg cctgccaaaa gggcaacatt   1680
aggtgcaaca tttgcatttg a                                                1701
```

<210> SEQ ID NO 15
<211> LENGTH: 566
<212> TYPE: PRT
<213> ORGANISM: Influenza A virus

<400> SEQUENCE: 15

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
                20                  25                  30

His His Ala Val Pro Asn Gly Thr Ile Val Lys Thr Ile Thr Asn Asp
            35                  40                  45

Arg Ile Glu Val Thr Asn Ala Thr Glu Leu Val Gln Asn Ser Ser Ile
        50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val

```
            115                 120                 125
Ala Ser Ser Gly Thr Leu Glu Phe Asn Asn Glu Ser Phe Asn Trp Asn
130                 135                 140

Gly Val Thr Gln Asn Gly Thr Ser Ser Ala Cys Ile Arg Arg Ser Asn
145                 150                 155                 160

Asn Ser Phe Phe Ser Arg Leu Asn Trp Leu Thr His Leu Asn Phe Lys
                165                 170                 175

Tyr Pro Ala Leu Asn Val Thr Met Pro Asn Asn Glu Gln Phe Asp Lys
            180                 185                 190

Leu Tyr Ile Trp Gly Val His His Pro Val Thr Asp Lys Asp Gln Ile
        195                 200                 205

Phe Leu Tyr Ala Gln Pro Ser Gly Arg Ile Thr Val Ser Thr Lys Arg
210                 215                 220

Ser Gln Gln Ala Val Ile Pro Asn Ile Gly Phe Arg Pro Arg Ile Arg
225                 230                 235                 240

Asn Asn Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Lys Ser Glu Cys Ile Thr Pro Asn Gly Ser Ile
290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Ser Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Arg Gly Gln Ala Ala Asp Leu Lys
370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
530                 535                 540
```

Val Ala Leu Leu Gly Phe Ile Met Trp Ala Cys Gln Lys Gly Asn Ile
545                 550                 555                 560

Arg Cys Asn Ile Cys Ile
            565

<210> SEQ ID NO 16
<211> LENGTH: 1755
<212> TYPE: DNA
<213> ORGANISM: Influenza B virus

<400> SEQUENCE: 16

```
atgaaggcaa taattgtact actaatggta gtaacatcca atgcagatcg aatctgcact     60
gggataacat cttcaaactc acctcatgtg gtcaaaacag ctactcaagg ggaggtcaat    120
gtgactggtg tgataccact aacaacaaca ccaacaaaat cttattttgc aaatctcaaa    180
ggaacaaaga ccagagggaa actatgccca gactgtctca actgtacaga tctggatgtg    240
gccctgggca ggccaatgtg tgtgggaact cacccttctg cgaaagcttc aatacttcac    300
gaagtcagac ctgttacatc cgggtgcttc cctataatgc acgacagaac aaaaatcagg    360
caactagcca atcttctcag aggatatgaa aatatcaggt tatcaaccca aaacgttatc    420
gatgcagaaa aggcaccagg aggaccctac agacttggaa cctcaggatc ttgccctaac    480
gctaccagta aaagcggatt tttcgcaaca atggcttggg ctgtcccaaa ggacaacaac    540
aaaaatgcaa cgaacccatt aacagtagaa gtaccataca tttgtgcaga aggggaagac    600
caaattactg tttggggggtt ccattcagat gacaaaaccc aaatgaagaa cctctatgga    660
gactcaaatc ctcaaaagtt cacctcatct gctaatggag taaccacaca ttatgtttct    720
cagattggcg gcttcccaga tcaaacagaa gacggaggac taccacaaag cggcagaatt    780
gtcgttgatt acatgatgca aaaacctggg aaaacaggaa caattgtcta tcaaagaggt    840
gttttgttgc ctcaaaaggt gtggtgcgcg agtggcagga gcaaagtaat aaaagggtcc    900
ttgccttaa ttggtgaagc agattgcctt catgaaaaat acggtggatt aaacaaaagc    960
aagccttact acacaggaga acatgcaaaa gccataggaa attgcccaat atgggtgaaa   1020
acacctttga agcttgccaa tggaaccaaa tatagacctc ctgcaaaact attaaaggaa   1080
aggggtttct tcggagctat tgctggtttc ctagaaggag gatgggaagg aatgattgca   1140
ggttggcacg gatacacatc tcacggagca catggagtgg cagttgctgc agaccttaag   1200
agcacacaag aagctataaa caagataaca aaaaatctca actctttgag tgagctagaa   1260
gtaaagaatc ttcaaaggct aagtggtgcc atggatgaac tccacaacga atactcgag   1320
ctggatgaga agtggatga cctcagagct gacactataa gttcacaaat gaacttgca   1380
gtcttgcttt ccaacgaagg aataataaac agtgaagacg agcatctatt ggcacttgag   1440
agaaaactaa agaaaatgct gggtccctct gctgtagaca taggaaatgg atgcttcgaa   1500
accaaacaca aatgcaacca gacctgctta gacaggatag ctgctggcac ctttaatgca   1560
ggagagtttt ctctccccac ttttgattca ttgaacatta ctgctgcatc tttaaatgat   1620
gatggattgg ataaccatac tatactgctc tattactcaa ctgctgcttc tagtttggct   1680
gtaacattga tgctagctat ttttattgtt tatatggtct ccagagacaa cgtttcatgc   1740
tccatctgtc tataa                                                    1755
```

<210> SEQ ID NO 17
<211> LENGTH: 584
<212> TYPE: PRT

<213> ORGANISM: Influenza B virus

<400> SEQUENCE: 17

Met Lys Ala Ile Ile Val Leu Leu Met Val Val Thr

```
Ser Thr Gln Glu Ala Ile Asn Lys Ile Thr Lys Asn Leu Asn Ser Leu
                405                 410                 415

Ser Glu Leu Glu Val Lys Asn Leu Gln Arg Leu Ser Gly Ala Met Asp
            420                 425                 430

Glu Leu His Asn Glu Ile Leu Glu Leu Asp Glu Lys Val Asp Asp Leu
        435                 440                 445

Arg Ala Asp Thr Ile Ser Ser Gln Ile Glu Leu Ala Val Leu Leu Ser
    450                 455                 460

Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Val Asp Ile Gly Asn
                485                 490                 495

Gly Cys Phe Glu Thr Lys His Lys Cys Asn Gln Thr Cys Leu Asp Arg
            500                 505                 510

Ile Ala Ala Gly Thr Phe Asn Ala Gly Glu Phe Ser Leu Pro Thr Phe
        515                 520                 525

Asp Ser Leu Asn Ile Thr Ala Ala Ser Leu Asn Asp Asp Gly Leu Asp
    530                 535                 540

Asn His Thr Ile Leu Leu Tyr Tyr Ser Thr Ala Ala Ser Ser Leu Ala
545                 550                 555                 560

Val Thr Leu Met Leu Ala Ile Phe Ile Val Tyr Met Val Ser Arg Asp
                565                 570                 575

Asn Val Ser Cys Ser Ile Cys Leu
            580
```

<210> SEQ ID NO 18
<211> LENGTH: 1677
<212> TYPE: DNA
<213> ORGANISM: Influenza B virus

<400> SEQUENCE: 18

```
atgaaggcaa taattgtact actcatggta gtaacatcca atgcagatcg aatctgcact        60
gggataacat cgtcaaactc accacatgtc gtcaaaactg ctactcaagg ggaggtcaat       120
gtgactggtg tataccact gacaacaaca cccaccaaat ctcattttgc aaatctcaaa       180
ggaacagaaa ccagggggaa actatgccca aaatgcctca actgcacaga tctggacgta       240
gccttgggca gaccaaaatg cacggggaaa tacctcgg caagagtttc aatactccat       300
gaagtcagac tgttacatc tgggtgcttt cctataatgc acgacagaac aaaaattaga       360
cagctgccta accttctccg aggatacgaa catatcaggt tatcaaccca taacgttatc       420
aatgcagaaa atgcaccagg aggaccctac aaaattggaa cctcagggtc ttgccctaac       480
attaccaatg gaaacggatt tttcgcaaca atggcttggg ccgtcccaaa aaacgacaaa       540
aacaaaacag caacaaatcc attaacaata gaagtaccat acatttgtac agaaggagaa       600
gaccaaatta ccgtttgggg gttccactct gacaacgaga cccaaatggc aaagctctat       660
ggggactcaa agccccagaa gttcacctca tctgccaacg gagtgaccac acattacgtt       720
tcacagattg gtggcttccc aaatcaaaca gaagacggag gactaccaca agtggtaga       780
attgttgttg attacatggt gcaaaaatct gggaaaacag gaacaattac ctatcaaagg       840
ggtatttttat tgcctcaaaa ggtgtggtgc gcaagtggca ggagcaaggt aataaaagga       900
tccttgcctt taattggaga agcagattgc ctccacgaaa atacggtgg attaaacaaa       960
agcaagcctt actacacagg ggaacatgca aaggccatag aaattgccc aatatgggtg      1020
aaaacaccct tgaagctggc caatggaacc aaatatagac ctcctgcaaa actattaaag     1080
```

```
gaaagggtt tcttcggagc tattgctggt ttcttagaag gaggatggga aggaatgatt    1140
gcaggttggc acggatacac atcccatggg gcacatggga tagcggtggc agcagacctt    1200
aagagcactc aagaggccat aaacaagata acaaaaaatc tcaactcttt gagtgagctg    1260
gaagtaaaga atcttcaaag actaagcggt gccatggatg aactccacaa cgaaatacta    1320
gaactagatg agaaagtgga tgatctcaga gctgatacaa taagctcaca aatagaactc    1380
gcagtcctgc tttccaatga aggaataata aacagtgaag atgaacatct cttggcgctt    1440
gaaagaaagc tgaagaaaat gctgggcccc tctgctgtag agatagggaa tggatgcttt    1500
gaaaccaaac acaagtgcaa ccagacctgt ctcgacagaa tagctgctgg tacctttgat    1560
gcaggagaat tttctctccc cacctttgat tcactgaata ttactgctgc atctttaaat    1620
gacgatggat tggataatca tactatactg ctttactact caactgctgc ctccagt     1677
```

<210> SEQ ID NO 19
<211> LENGTH: 559
<212> TYPE: PRT
<213> ORGANISM: Influenza B virus

<400> SEQUENCE: 19

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
        195                 200                 205

His Ser Asp Asn Glu Thr Gln Met Ala Lys Leu Tyr Gly Asp Ser Lys
    210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270
```

```
Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
        355                 360                 365

Ala Gly Phe Leu Glu Gly Gly Trp Glu Gly Met Ile Ala Gly Trp His
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
        435                 440                 445

Leu Arg Ala Asp Thr Ile Ser Ser Gln Ile Glu Leu Ala Val Leu Leu
    450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
        515                 520                 525

Phe Asp Ser Leu Asn Ile Thr Ala Ala Ser Leu Asn Asp Asp Gly Leu
    530                 535                 540

Asp Asn His Thr Ile Leu Leu Tyr Tyr Ser Thr Ala Ala Ser Ser
545                 550                 555

<210> SEQ ID NO 20
<211> LENGTH: 1777
<212> TYPE: DNA
<213> ORGANISM: Influenza A virus

<400> SEQUENCE: 20
agcaaaagca ggggaaaata aaagcaacaa aaatgaaggc aatactagta gttctgctat      60
atacatttgc aaccgcaaat gcagacacat tatgtatagg ttatcatgcg aacaattcaa     120
cagacactgt agacacagta ctagaaaaga atgtaacagt aacacactct gttaaccttc     180
tagaagacaa gcataacggg aaactatgca actaagaggg gtagccccca ttgcatttgg     240
gtaaatgtaa cattgctggc tggatcctgg gaaatccaga gtgtgaatca ctctccacag     300
caagctcatg gtcctacatt gtggaaacac ctagttcaga caatggaacg tgttacccag     360
gagatttcat cgattatgag gagctaagag agcaattgag ctcagtgtca tcatttgaaa     420
ggtttgagat attccccaat acaagttcat ggcccaatca tgactcgaac aaaggtgtaa     480
```

```
cggcagcatg tcctcatgct ggagcaaaaa gcttctacaa aaatttaata tggctagtta      540
aaaaaggaaa ttcataccca aagctcagca atcctacat taatgataaa gggaaagaag       600
tcctcgtgct atggggcatt caccatccac ctactagtgc tgaccaacaa agtctctatc      660
agaatgcaga tacatatgtt tttgtggggt catcaagata cagcaagaag ttcaagccgg      720
aaatagcaat aagacccaaa gtgagggtgc aagaaggag aatgaactat tactggacac       780
tagtagagcc gggagacaaa ataacattcg aagcaactgg aaatctagtg gtaccgagat      840
atgcattcgc aatggaaaga atgctggat ctggtattat catttcagat acaccagtcc       900
acgattgcaa tacaacttgt caaacaccca agggtgctat aaacaccagc ctcccatttc      960
agaatataca tccgatcaca attggaaaat gtccaaaata tgtaaaaagc acaaaattga     1020
gactggccac aggattgagg aatatcccgt ctattcaatc tagaggccta tttggggcca     1080
ttgccggttt cattgaaggg gggtggacag ggatggtaga tggatggtac ggttatcacc     1140
atcaaaatga gcaggggtca ggatatgcag ccgacctgaa gagcacacag aatgccattg     1200
acgagattac taacaaagta attctgtta ttgaaaagat gaatacacag ttcacagcag      1260
taggtaaaga gttcaaccac ctggaaaaaa gaatagagaa tttaaataaa aaagttgatg     1320
atggtttcct ggacatttgg acttacatg ccgaactgtt ggttctattg gaaaatgaaa      1380
gaactttgga ctaccacgat tcaaatgtga agaacttata tgaaaaggta agaagccagc     1440
taaaaaacaa tgccaaggaa attggaaacg gctgctttga attttaccac aaatgcgata     1500
acacgtgcat ggaaagtgtc aaaaatggga cttatgacta cccaaaatac tcagaggaag     1560
caaaattaaa cagagaagaa atagatgggg taaagctgga atcaacaagg atttaccaga     1620
ttttggcgat ctattcaact gtcgccagtt cattggtact ggtagtctcc ctgggggcaa     1680
tcagtttctg gatgtgctct aatgggtctc tacagtgtag aatatgtatt taacattagg     1740
atttcagaag catgagaaaa acaccttgt ttctact                               1777

<210> SEQ ID NO 21
<211> LENGTH: 566
<212> TYPE: PRT
<213> ORGANISM: Influenza A virus

<400> SEQUENCE: 21

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Lys His Asn Gly Lys Leu Cys Lys Leu Arg Gly Val
        50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Asn Thr Ser Ser Trp Pro Asn His Asp
    130                 135                 140
```

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
            165                 170                 175

Lys Leu Ser Lys Ser Tyr Ile Asn Asp Lys Gly Lys Glu Val Leu Val
        180                 185                 190

Leu Trp Gly Ile His His Pro Pro Thr Ser Ala Asp Gln Gln Ser Leu
    195                 200                 205

Tyr Gln Asn Ala Asp Thr Tyr Val Phe Val Gly Ser Ser Arg Tyr Ser
210                 215                 220

Lys Lys Phe Lys Pro Glu Ile Ala Ile Arg Pro Lys Val Arg Gly Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile

-continued

```
                565

<210> SEQ ID NO 22
<211> LENGTH: 207
<212> TYPE: DNA
<213> ORGANISM: Homo sapiens

<400> SEQUENCE: 22
gctggctgct cgtggtgtac aggtccccgg aggcatcctg gctgggtggg aagtttctgg      60
cggtcacgcc ctgtccgctt tcgctccagg tcacactgag tggctcctgg gggaagaagc     120
cctggaccag gcaggcgatg accacgttcc catctggctg ggtgctgcag aggctcagcg     180
ggaagacctt ggggctggtc ggggatg                                         207

<210> SEQ ID NO 23
<211> LENGTH: 207
<212> TYPE: DNA
<213> ORGANISM: Homo sapiens

<400> SEQUENCE: 23
gctggctgct cgtggtgtac aggtccccgg aggcatcctg gctgggtggg aagtttctgg      60
cggtcacgcc ctgtccgctt tcgctccagg tcacactgag tggctcctgg gggaagaagc     120
cctggaccag gcaggcgatg accacgttcc catctggctg ggtgctgcag aggctcagcg     180
ggaagacctt ggggctggtc ggggatg                                         207

<210> SEQ ID NO 24
<211> LENGTH: 80
<212> TYPE: PRT
<213> ORGANISM: Influenza A virus

<400> SEQUENCE: 24

Asp Thr Ile Ser Ile Gly Tyr His Ala Asn Asn Ser Thr Asp Thr Val
1               5                   10                  15

Asp Thr Val Leu Glu Lys Asn Val Thr Val Thr His Ser Val Asn Leu
                20                  25                  30

Leu Glu Asp Ser His Asn Gly Lys Leu Ser Leu Leu Lys Gly Ile Ala
            35                  40                  45

Pro Leu Gln Leu Gly Asn Cys Ser Val Ala Gly Trp Ile Leu Gly Asn
        50                  55                  60

Pro Glu Cys Glu Leu Leu Ile Ser Lys Glu Ser Trp Ser Tyr Ile Val
65                  70                  75                  80

<210> SEQ ID NO 25
<211> LENGTH: 80
<212> TYPE: PRT
<213> ORGANISM: Influenza A virus

<400> SEQUENCE: 25

Ile Leu Gly Asn Pro Glu Ser Glu Leu Leu Ile Ser Lys Glu Ser Trp
1               5                   10                  15

Ser Tyr Ile Val Glu Thr Pro Asn Pro Glu Asn Gly Thr Cys Tyr Pro
                20                  25                  30

Gly Tyr Phe Ala Asp Tyr Glu Glu Leu Arg Glu Gln Leu Ser Ser Val
            35                  40                  45

Ser Ser Phe Glu Arg Phe Glu Ile Phe Pro Lys Glu Ser Ser Trp Pro
        50                  55                  60

Asn His Thr Val Thr Gly Val Ser Ala Ser Cys Ser His Asn Gly Lys
65                  70                  75                  80
```

<210> SEQ ID NO 26
<211> LENGTH: 80
<212> TYPE: PRT
<213> ORGANISM: Influenza A virus

<400> SEQUENCE: 26

Ser Ser Trp Pro Asn His Thr Val Thr Gly Val Ser Ala Ser Cys Ser
1               5                   10                  15

His Asn Gly Lys Ser Ser Phe Tyr Arg Asn Leu Leu Trp Leu Thr Gly
            20                  25                  30

Lys Asn Gly Leu Tyr Pro Asn Leu Ser Lys Ser Tyr Val Asn Asn Lys
        35                  40                  45

Glu Lys Glu Val Leu Val Leu Trp Gly Val His His Pro Pro Asn Ile
50 55 60

Gly Asn Gln Arg Ala Leu Tyr His Thr Glu Asn Ala Tyr Val Ser Val
65 70 75 80

<210> SEQ ID NO 27
<211> LENGTH: 80
<212> TYPE: PRT
<213> ORGANISM: Influenza A virus

<400> SEQUENCE: 27

Pro Pro Asn Ile Gly Asn Gln Arg Ala Leu Tyr His Thr Glu Asn Ala
1 5 10 15

Tyr Val Ser Val Val Ser Ser His Tyr Ser Arg Arg Phe Thr Pro Glu
20 25 30

Ile Ala Lys Arg Pro Lys Val Arg Asp Gln Glu Gly Arg Ile Asn Tyr
35 40 45

Tyr Trp Thr Leu Leu Glu Pro Gly Asp Thr Ile Ile Phe Glu Ala Asn
50 55 60

Gly Asn Leu Ile Ala Pro Trp Tyr Ala Phe Ala Leu Ser Arg Gly Phe
65 70 75 80

<210> SEQ ID NO 28
<211> LENGTH: 80
<212> TYPE: PRT
<213> ORGANISM: Influenza A virus

<400> SEQUENCE: 28

Phe Glu Ala Asn Gly Asn Leu Ile Ala Pro Trp Tyr Ala Phe Ala Leu
1 5 10 15

Ser Arg Gly Phe Gly Ser Gly Ile Ile Thr Ser Asn Ala Pro Met Asp
20 25 30

Glu Ser Asp Ala Lys Cys Gln Thr Pro Gln Gly Ala Ile Asn Ser Ser
35 40 45

Leu Pro Phe Gln Asn Val His Pro Val Thr Ile Gly Glu Cys Pro Lys
50 55 60

Tyr Val Arg Ser Ala Lys Leu Arg Met Val Thr Gly Leu Arg Asn Ile
65 70 75 80

<210> SEQ ID NO 29
<211> LENGTH: 80
<212> TYPE: PRT
<213> ORGANISM: Influenza A virus

<400> SEQUENCE: 29

Gly Glu Cys Pro Lys Tyr Val Arg Ser Ala Lys Leu Arg Met Val Thr

```
1               5                   10                  15

Gly Leu Arg Asn Ile Pro Ser Ile Gln Ser Arg Gly Leu Phe Gly Ala
            20                  25                  30

Ile Ala Gly Phe Ile Glu Gly Gly Trp Thr Gly Met Val Asp Gly Trp
        35                  40                  45

Tyr Gly Tyr His His Gln Asn Glu Gln Gly Ser Gly Tyr Ala Ala Asp
    50                  55                  60

Gln Lys Ser Thr Gln Asn Ala Ile Asn Gly Ile Thr Asn Lys Val Asn
65                  70                  75                  80

<210> SEQ ID NO 30
<211> LENGTH: 79
<212> TYPE: PRT
<213> ORGANISM: Influenza A virus

<400> SEQUENCE: 30

Tyr Ala Ala Asp Gln Lys Ser Thr Gln Asn Ala Ile Asn Gly Ile Thr
1               5                   10                  15

Asn Lys Val Asn Ser Val Ile Glu Lys Met Asn Thr Gln Phe Thr Ala
            20                  25                  30

Val Gly Lys Glu Phe Asn Lys Leu Glu Arg Arg Met Glu Asn Leu Asn
        35                  40                  45

Lys Lys Val Asp Asp Gly Phe Leu Asp Ile Trp Thr Tyr Asn Ala Glu
    50                  55                  60

Leu Leu Val Leu Leu Glu Asn Glu Arg Thr Leu Asp Phe His Asp
65                  70                  75

<210> SEQ ID NO 31
<211> LENGTH: 80
<212> TYPE: PRT
<213> ORGANISM: Influenza A virus

<400> SEQUENCE: 31

Thr Tyr Asn Ala Glu Leu Leu Val Leu Leu Glu Asn Glu Arg Thr Leu
1               5                   10                  15

Asp Phe His Asp Ser Asn Val Lys Asn Leu Tyr Glu Lys Val Lys Ser
            20                  25                  30

Gln Leu Lys Asn Asn Ala Lys Glu Ile Gly Asn Gly Ser Phe Glu Phe
        35                  40                  45

Tyr His Lys Cys Asn Asn Glu Cys Met Glu Ser Val Lys Asn Gly Thr
    50                  55                  60

Tyr Asp Tyr Pro Lys Tyr Ser Glu Glu Ser Lys Leu Asn Arg Glu Lys
65                  70                  75                  80

<210> SEQ ID NO 32
<211> LENGTH: 40
<212> TYPE: PRT
<213> ORGANISM: Influenza A virus

<400> SEQUENCE: 32

Lys Asn Gly Thr Tyr Asp Tyr Pro Lys Tyr Ser Glu Glu Ser Lys Leu
1               5                   10                  15

Asn Arg Glu Lys Ile Asp Gly Val Lys Leu Glu Ser Met Gly Val Tyr
            20                  25                  30

Gln Ile Leu Ala Ile Tyr Ser Thr
        35                  40

<210> SEQ ID NO 33
```

-continued

```
<211> LENGTH: 46
<212> TYPE: PRT
<213> ORGANISM: Influenza A virus

<400> SEQUENCE: 33

Lys Leu Glu Ser Met Gly Val Tyr Gln Ile Leu Ala Ile Tyr Ser Thr
1               5                   10                  15

Val Ala Ser Ser Leu Val Leu Leu Val Ser Leu Gly Ala Ile Ser Phe
            20                  25                  30

Trp Met Ser Ser Asn Gly Ser Leu Gln Ser Arg Ile Ser Ile
        35                  40                  45

<210> SEQ ID NO 34
<211> LENGTH: 22
<212> TYPE: DNA
<213> ORGANISM: Artificial Sequence
<220> FEATURE:
<223> OTHER INFORMATION: Primer

<400> SEQUENCE: 34
gaggctcagc gggaagacct tg                                              22

<210> SEQ ID NO 35
<211> LENGTH: 58
<212> TYPE: DNA
<213> ORGANISM: Artificial Sequence
<220> FEATURE:
<223> OTHER INFORMATION: Illumina specific linker forward:

<400> SEQUENCE: 35
caagcagaag acggcatacg agatgtgact ggagttcaga cgtgtgctct tccgatct       58

<210> SEQ ID NO 36
<211> LENGTH: 58
<212> TYPE: DNA
<213> ORGANISM: Artificial Sequence
<220> FEATURE:
<223> OTHER INFORMATION: Illumina specific linker reverse

<400> SEQUENCE: 36
aatgatacgg cgaccaccga gatctacact ctttccctac acgacgctct tccgatct       58
```